(12) United States Patent
Audonnet et al.

(10) Patent No.: US 7,534,559 B2
(45) Date of Patent: May 19, 2009

(54) FELINE POLYNUCLEOTIDE VACCINE FORMULA

(75) Inventors: Jean-Christophe Audonnet, Lyons (FR); Annabelle Bouchardon, Lyons (FR); Philippe Baudu, Craponne (FR); Michel Riviere, Ecully (FR)

(73) Assignee: Merial, Lyons (FR)

( * ) Notice: Subject to any disclaimer, the term of this patent is extended or adjusted under 35 U.S.C. 154(b) by 289 days.

(21) Appl. No.: 09/943,443

(22) Filed: Aug. 30, 2001

(65) Prior Publication Data

US 2003/0017172 A1    Jan. 23, 2003

Related U.S. Application Data

(60) Division of application No. 09/232,278, filed on Jan. 15, 1999, now Pat. No. 6,348,196, which is a continuation-in-part of application No. PCT/FR97/01315, filed on Jul. 15, 1997.

(30) Foreign Application Priority Data

Jul. 19, 1996    (FR)    ................................ 96 09337

(51) Int. Cl.
A61K 39/21    (2006.01)
(52) U.S. Cl. ................ 435/6; 536/23.72; 424/208.1
(58) Field of Classification Search .............. 424/207.1, 424/208.1; 435/69.1
See application file for complete search history.

(56) References Cited

U.S. PATENT DOCUMENTS

| | | | |
|---|---|---|---|
| 5,529,780 A | 6/1996 | Paoletti et al. | |
| 5,665,362 A | 9/1997 | Inglis et al. | |
| 5,804,196 A * | 9/1998 | Mazzara et al. | ............ 424/208.1 |

FOREIGN PATENT DOCUMENTS

| | | |
|---|---|---|
| AU | 74116/94 | 6/1995 |
| EP | 0 411 684 | 2/1991 |
| WO | WO 91/01332 | 2/1991 |
| WO | WO 94/06921 | 3/1994 |
| WO | WO 95/07987 | 3/1995 |
| WO | WO 95/20660 | 8/1995 |
| WO | WO95/30019 A1 * | 11/1995 |
| WO | WO 96/06934 | 3/1996 |
| WO | WO 96/18390 | 6/1996 |

OTHER PUBLICATIONS

Choi et al., Anti-Feline Immunodeficiency Virus (FIV) Soluble Factor(s), J. Virology, 2000, vol. 74, No. 2, pp. 676-683.*
Cuisinier et al. DNA vaccination using expression vectors carrying FIV structural genes induces immune response against feline immunodeficiency virus, Vaccine (Jul. 1997), 15(10):1085-1094.*
Carlson et al., Journal of Virology, 55(3):574-582, 1985.
Elder et al., Journal of Virology, 67(4):1869-76, 1993.
Ertl et al., Annals New York Academy of Sciences, 772:77-87, 1996.
Franke et al., Tierarztl. Prax. 18:629-632, 1990.
Truyen et al., Tierarztl. Prax. 23:300-5, 1995.
Gonin et al , Vaccine Research, 4 4:217-227, 1995.
Vennema et al., Virology, 181:327-335, 1991.
Andre et al., pp. 41-54 in Modern Vaccinology, ed. Kurstak e., Plenum Medical Book Company, New York, 1994.
R.C. Wardley et al., The Use of Feline Herpesvirus and Baculovirus as Vaccine Vectors for the Gag and Env Genes of Feline Leukaemia Virus, J. General Virology, vol. 73, part 07 (1992) pp. 1811-1818, 1992.
Herbert et al., ed., The Dictionary of Immunology, 4th ed., Academic Press. London. p. 163, 1995.

* cited by examiner

*Primary Examiner*—Stacy B Chen
(74) *Attorney, Agent, or Firm*—Judy Jarecki-Black; Merial Limited; Thomas Kowalski, Esq.

(57) ABSTRACT

Disclosed are plasmids that contain and express in vivo in a feline host cell nucleic acid molecules. The plasmid can include nucleic molecule(s) having sequence(s) encoding infectious peritonitis virus M; feline immunodeficiency virus env, or gag, or pro, or gag and pro, or env and gag and pro; rabies G; or feline leukemia virus env and/or gag. Compositions containing such plasmids, methods of use employing such plasmids, and kits involving such plasmids, are also disclosed.

11 Claims, 19 Drawing Sheets

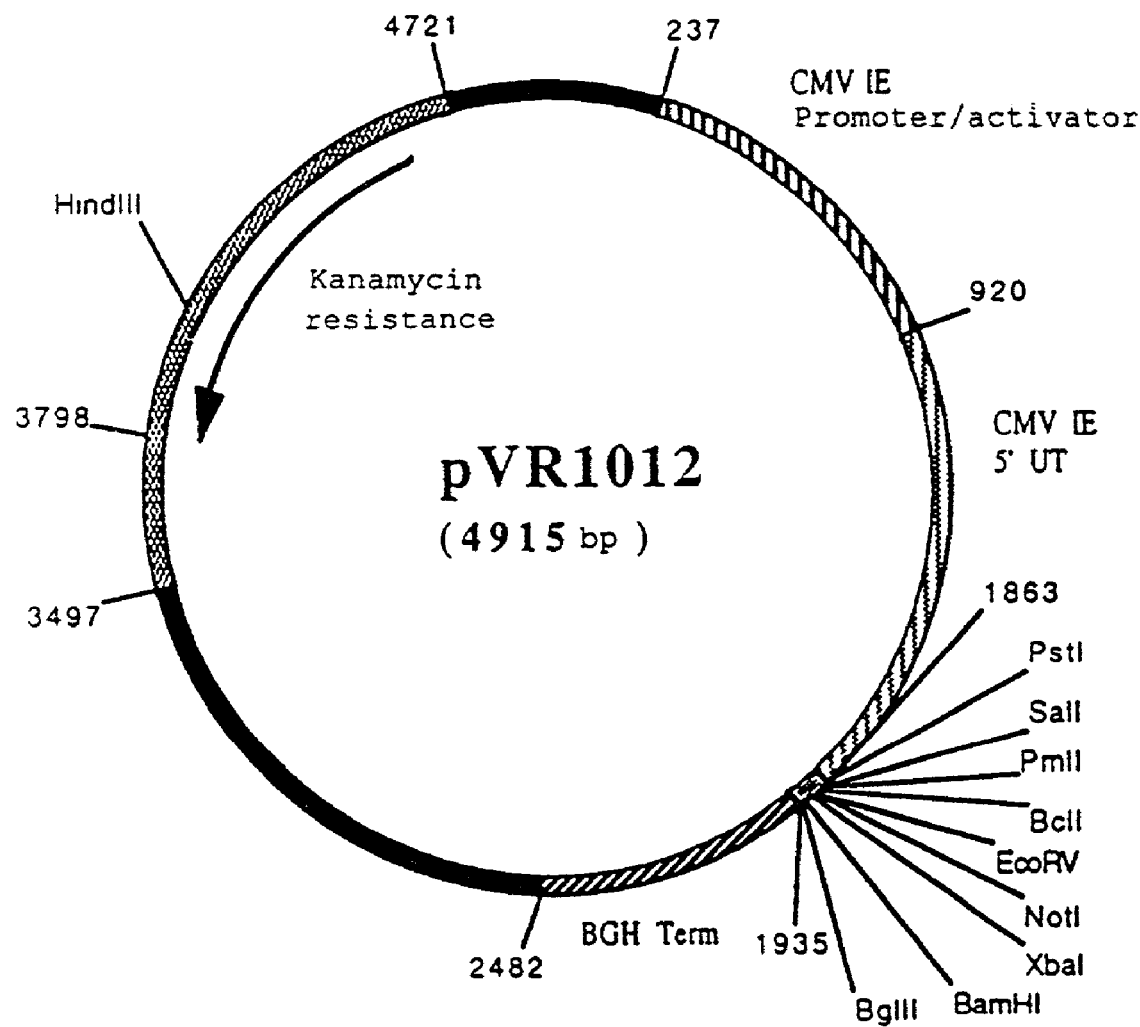
Figure No. 1

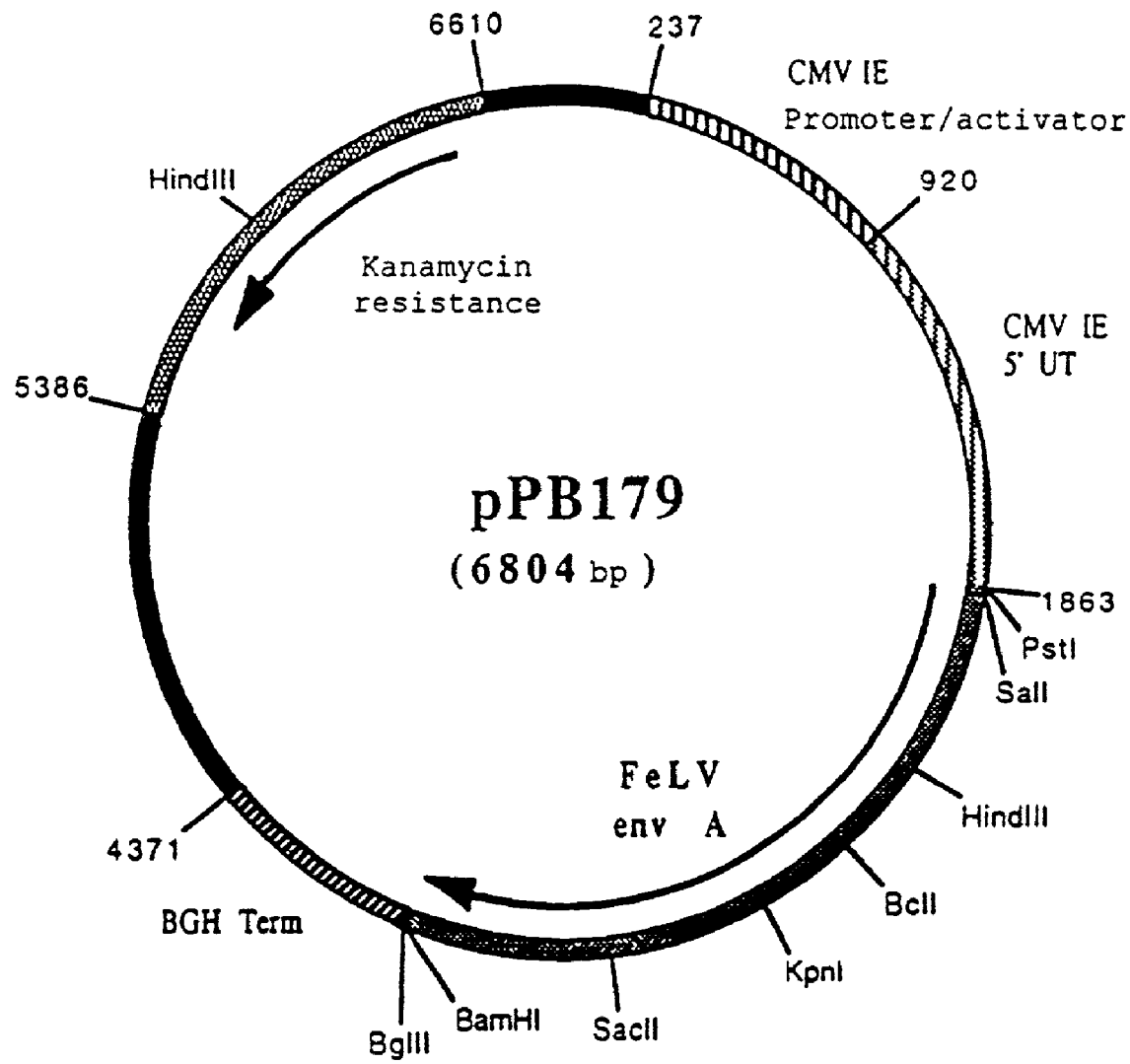
Figure No. 2

```
   1 ATGGAAGGTCCAACGCACCCAAAACCCTCTAAAGATAAGACTTTCTCGTGGGACCTAATGATT
   1▶MetGluGlyProThrHisProLysProSerLysAspLysThrPheSerTrpAspLeuMetIle

64 CTGGTGGGGGTCTTACTAAGACTGGACGTGGGAATGGCCAATCCTAGTCCGCACCAAATATAT
  22▶LeuValGlyValLeuLeuArgLeuAspValGlyMetAlaAsnProSerProHisGlnIleTyr

127 AATGTAACTTGGACAATAACCAACCTTGTAACTGGAACAAAGGCTAATGCCACCTCCATGTTG
  43▶AsnValThrTrpThrIleThrAsnLeuValThrGlyThrLysAlaAsnAlaThrSerMetLeu

190 GGAACCCTGACAGACGCCTTCCCTACCATGTATTTTGACTTATGTGATATAATAGGAAATACA
  64▶GlyThrLeuThrAspAlaPheProThrMetTyrPheAspLeuCysAspIleIleGlyAsnThr

253 TGGAACCCTTCAGATCAAGAACCATTCCCAGGGTATGGATGTGATCAGCCTATGAGGAGGTGG
  85▶TrpAsnProSerAspGlnGluProPheProGlyTyrGlyCysAspGlnProMetArgArgTrp

316 CGACAGAGAAACACACCCTTTTATGTCTGTCCAGGACATGCCAACCGGAAGCAATGTGGGGGG
 106▶ArgGlnArgAsnThrProPheTyrValCysProGlyHisAlaAsnArgLysGlnCysGlyGly

379 CCACAGGATGGGTTCTGCGCTGTATGGGGTTGCGAGACCACCGGGGAAACCTATTGGAGACCC
 127▶ProGlnAspGlyPheCysAlaValTrpGlyCysGluThrThrGlyGluThrTyrTrpArgPro

442 ACCTCCTCATGGGACTACATCACAGTAAAAAAAGGGGTTACTCAGGGAATATATCAATGTAGT
 148▶ThrSerSerTrpAspTyrIleThrValLysLysGlyValThrGlnGlyIleTyrGlnCysSer

505 GGAGGTGGTTGGTGTGGGCCCTGTTACGATAAAGCTGTTCACTCCTCGACAACGGGAGCTAGT
 169▶GlyGlyGlyTrpCysGlyProCysTyrAspLysAlaValHisSerSerThrThrGlyAlaSer

568 GAAGGGGGCCGGTGCAACCCCTTGATCTTGCAATTTACCCAAAAGGGAAGACAAACATCTTGG
 190▶GluGlyGlyArgCysAsnProLeuIleLeuGlnPheThrGlnLysGlyArgGlnThrSerTrp

631 GATGGACCTAAGTCATGGGGGCTACGACTATACCGTTCAGGATATGACCCTATAGCCCTGTTC
 211▶AspGlyProLysSerTrpGlyLeuArgLeuTyrArgSerGlyTyrAspProIleAlaLeuPhe

694 TCGGTATCCCGGCAAGTAATGACCATTACGCCGCCTCAGGCCATGGGACCAAATCTAGTCCTG
 232▶SerValSerArgGlnValMetThrIleThrProProGlnAlaMetGlyProAsnLeuValLeu

757 CCTGATCAAAAACCCCCATCCAGGCAATCTCAAATAGAGTCCCGAGTAACACCTCACCATTCC
 253▶ProAspGlnLysProProSerArgGlnSerGlnIleGluSerArgValThrProHisHisSer

820 CAAGGCAACGGAGGCACCCCAGGTGTAACTCTTGTTAATGCCTCCATTGCCCCTCTACGTACC
 274▶GlnGlyAsnGlyGlyThrProGlyValThrLeuValAsnAlaSerIleAlaProLeuArgThr

883 CCTGTCACCCCCGCAAGTCCCAAACGTATAGGGACCGGAAATAGGTTAATAAATTTAGTGCAA
 295▶ProValThrProAlaSerProLysArgIleGlyThrGlyAsnArgLeuIleAsnLeuValGln

946 GGGACATACCTAGCCTTAAATGCCACCGACCCCAACAAAACTAAAGACTGTTGGCTCTGCCTG
 316▶GlyThrTyrLeuAlaLeuAsnAlaThrAspProAsnLysThrLysAspCysTrpLeuCysLeu

1009 GTTTCTCGACCACCTTATTACGAAGGGATTGCAATCTTAGGTAACTACAGCAACCAAACAAAC
 337▶ValSerArgProProTyrTyrGluGlyIleAlaIleLeuGlyAsnTyrSerAsnGlnThrAsn

1072 CCCTCCCCATCCTGCCTATCTACTCCGCAACATAAGCTAACTATATCTGAGGTGTCAGGGCAA
 358▶ProSerProSerCysLeuSerThrProGlnHisLysLeuThrIleSerGluValSerGlyGln

1135 GGACTGTGCATAGGGACTGTTCCTAAGACCCACCAGGCTTTGTGCAATAAGACACAACAGGGA
 379▶GlyLeuCysIleGlyThrValProLysThrHisGlnAlaLeuCysAsnLysThrGlnGlnGly

1198 CATACAGGGGCTCACTATCTAGCCGCCCCAATGGCACCTATTGGGCCTGTAACACTGGACTC
 400▶HisThrGlyAlaHisTyrLeuAlaAlaProAsnGlyThrTyrTrpAlaCysAsnThrGlyLeu
```

Figure No. 3

```
1261 ACCCCATGCATTTCCATGGCAGTGCTCAATTGGACCTCTGATTTTTGTGTCTTAATCGAATTA
 421▶ThrProCysIleSerMetAlaValLeuAsnTrpThrSerAspPheCysValLeuIleGluLeu

1324 TGGCCCAGAGTGACCTACCATCAACCCGAATACATTTACACACATTTCGACAAAGCTGTCAGG
 442▶TrpProArgValThrTyrHisGlnProGluTyrIleTyrThrHisPheAspLysAlaValArg

1387 TTCCGAAGAGAACCAATATCACTAACCGTTGCCCTTATAATGGGAGGACTCACTGTAGGGGGC
 463▶PheArgArgGluProIleSerLeuThrValAlaLeuIleMetGlyGlyLeuThrValGlyGly

1450 ATAGCCGCGGGGGTCGGAACAGGGACTAAAGCCCTCCTTGAAACAGCCCAGTTCAGACAACTA
 484▶IleAlaAlaGlyValGlyThrGlyThrLysAlaLeuLeuGluThrAlaGlnPheArgGlnLeu

1513 CAAATGGCTATGCACGCAGACATCCAGGCCCTAGAAGAGTCAATTAGTGCCTTAGAAAAATCC
 505▶GlnMetAlaMetHisAlaAspIleGlnAlaLeuGluGluSerIleSerAlaLeuGluLysSer

1576 CTGACCTCCCTCTCCGAGGTAGTCTTACAAAATAGACGGGGCCTAGATATTCTGTTCTTACAA
 526▶LeuThrSerLeuSerGluValValLeuGlnAsnArgArgGlyLeuAspIleLeuPheLeuGln

1639 AAGGGAGGGCTCTGTGCCGCCTTAAAGGAAGAATGCTGCTTCTATGCAGATCACACCGGACTC
 547▶LysGlyGlyLeuCysAlaAlaLeuLysGluGluCysCysPheTyrAlaAspHisThrGlyLeu

1702 GTCAGAGACAATATGGCTAAATTAAGAGAAAGACTGAAACAGCGACAACAACTGTTTGACTCC
 568▶ValArgAspAsnMetAlaLysLeuArgGluArgLeuLysGlnArgGlnGlnLeuPheAspSer

1765 CAACAGGGATGGTTTGAAGGATGGTTCAACAAGTCCCCCTGGTTTACAACCCTAATTTCCTCC
 589▶GlnGlnGlyTrpPheGluGlyTrpPheAsnLysSerProTrpPheThrThrLeuIleSerSer

1828 ATTATAGGCCCCTTACTAATCCTACTCCTAATTCTCCTCTTCGGCCCATGCATCCTTAACCGA
 610▶IleIleGlyProLeuLeuIleLeuLeuIleLeuLeuPheGlyProCysIleLeuAsnArg

1891 TTAGTGCAATTCGTAAAAGACAGAATATCTGTGGTACAAGCCTTAATTTTAACCCAACAGTAC
 631▶LeuValGlnPheValLysAspArgIleSerValValGlnAlaLeuIleLeuThrGlnGlnTyr

1954 CAACAGATACAGCAATATGATCCGGACCGACCATGA
 652▶GlnGlnIleGlnGlnTyrAspProAspArgPro•••
```

Figure No. 3 (continuation and end)

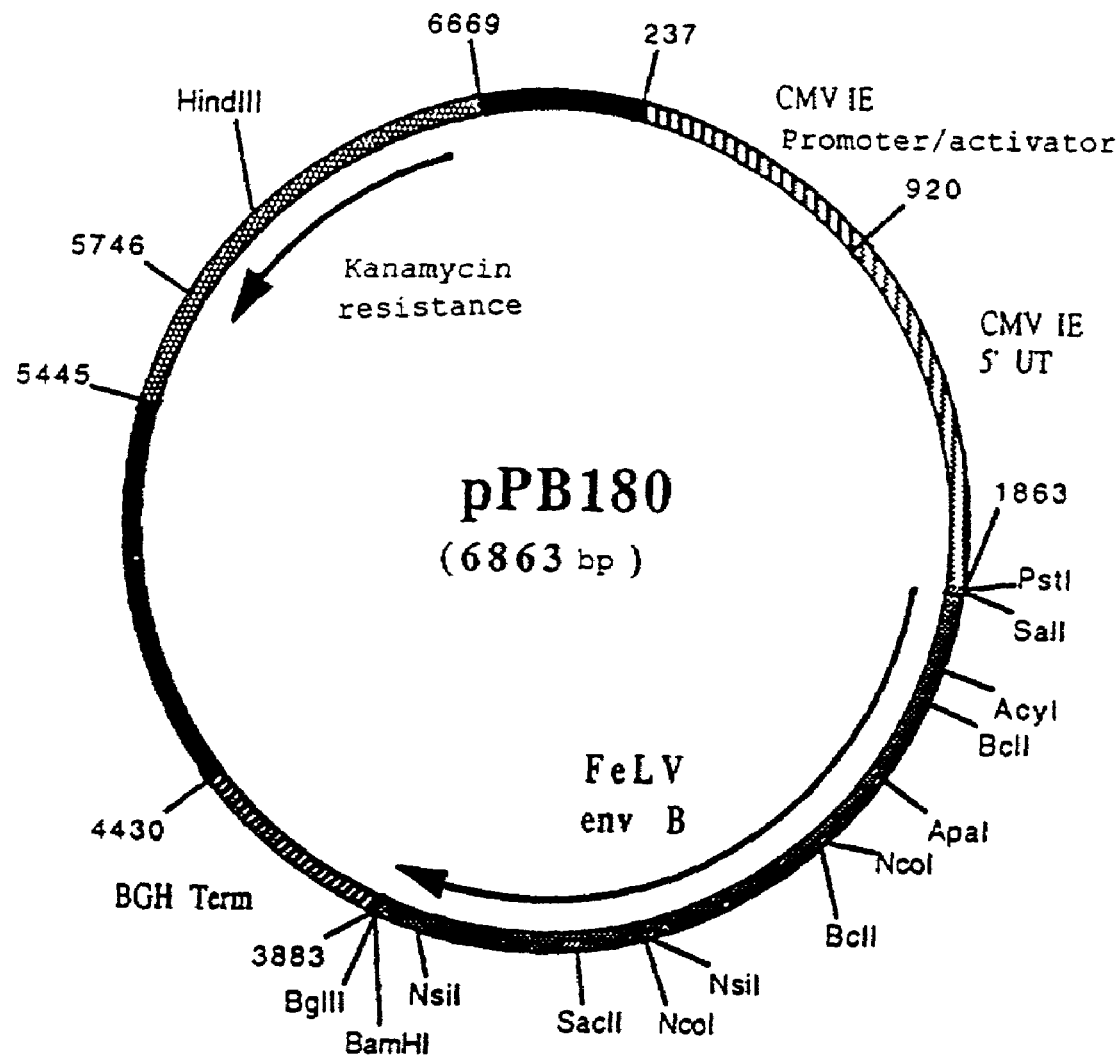
Figure No. 4

```
  1 ATGTCTGGAGCCTCTAGTGGGACAGCCATTGGGGCTCATCTGTTTGGGGTCTCACCTGAATAC
  1▶MetSerGlyAlaSerSerGlyThrAlaIleGlyAlaHisLeuPheGlyValSerProGluTyr

64 AGGGTGTTGATCGGAGACGAGGGAGCCGGACCCTCAAGGTCTCTTTCTGAGTTTCATTTTCG
 22▶ArgValLeuIleGlyAspGluGlyAlaGlyProSerArgSerLeuSerGluValSerPheSer

127 GTTTGGTACCAAAGACGCGCGGCACGTCTTGTCATTTTTTGTCTGGTTGCGTCTTTTCTTGTC
 43▶ValTrpTyrGlnArgArgAlaAlaArgLeuValIlePheCysLeuValAlaSerPheLeuVal

190 CCTTGTCTAACCTTTTTAATTGCAGAAACCGTCATGGGCCAAACTATAACTACCCCCTTAAGC
 64▶ProCysLeuThrPheLeuIleAlaGluThrValMetGlyGlnThrIleThrThrProLeuSer

253 CTCACCCTTGATCACTGGTCTGAAGTCCGGGCACGAGCCCATAATCAAGGTGTCGAGGTCCGG
 85▶LeuThrLeuAspHisTrpSerGluValArgAlaArgAlaHisAsnGlnGlyValGluValArg

316 AAAAAGAAATGGATTACCTTATGTGAGGCCGAATGGGTGATGATGAATGTGGGCTGGCCCCGA
106▶LysLysLysTrpIleThrLeuCysGluAlaGluTrpValMetMetAsnValGlyTrpProArg

379 GAAGGAACTTTTTCTCTTGATAGCATTTCCCAGGTTGAAAAGAAGATCTTCGCCCCGGGACCA
127▶GluGlyThrPheSerLeuAspSerIleSerGlnValGluLysLysIlePheAlaProGlyPro

442 TATGGACACCCCGACCAAGTTCCTTACATTACTACATGGAGATCCTTAGCCACAGACCCCCCT
148▶TyrGlyHisProAspGlnValProTyrIleThrThrTrpArgSerLeuAlaThrAspProPro

505 TCGTGGGTTCGTCCGTTCCTACCCCCTCCCAAACCTCCCACACCCCTCCCTCAACCTCTTTCG
169▶SerTrpValArgProPheLeuProProProLysProProThrProLeuProGlnProLeuSer

568 CCGCAGCCCTCCGCCCTCTTACCTCTTCCCTCTACCCCGTTCTCCCCAAGCCAGACCCCCCC
190▶ProGlnProSerAlaProLeuThrSerSerLeuTyrProValLeuProLysProAspProPro

631 AAACCGCCTGTGTTACCGCCTGATCCTTCTTCCCCTTTAATTGATCTCTTAACAGAAGAGCCA
211▶LysProProValLeuProProAspProSerSerProLeuIleAspLeuLeuThrGluGluPro

694 CCTCCCTATCCGGGGGGTCACGGGCCACCGCCATCAGGTCCTAGGACCCCAACCGCTTCCCCG
232▶ProProTyrProGlyGlyHisGlyProProProSerGlyProArgThrProThrAlaSerPro

757 ATTGCAAGCCGGCTAAGGGAACGACGAGAAAACCCTGCTGAAGAATCGCAAGCCCTCCCCTTG
253▶IleAlaSerArgLeuArgGluArgArgGluAsnProAlaGluGluSerGlnAlaLeuProLeu

820 AGGGAAGGCCCCAACAACCGACCCCAGTATTGGCCATTCTCAGCTTCAGACTTGTATAACTGG
274▶ArgGluGlyProAsnAsnArgProGlnTyrTrpProPheSerAlaSerAspLeuTyrAsnTrp

883 AAGTCGCATAACCCCCCTTTCTCCCAAGATCCAGTGGCCCTAACTAACCTAATTGAGTCCATT
295▶LysSerHisAsnProProPheSerGlnAspProValAlaLeuThrAsnLeuIleGluSerIle

946 TTAGTGACGCATCAACCAACCTGGGACGACTGCCAGCAGCTCTTGCAGGCACTCCTGACAGGC
316▶LeuValThrHisGlnProThrTrpAspAspCysGlnGlnLeuLeuGlnAlaLeuLeuThrGly

1009 GAAGAAAGGCAAAGGGTCCTTCTTGAGGCCCGAAAGCAGGTTCCAGGCGAGGACGGACGGCCA
337▶GluGluArgGlnArgValLeuLeuGluAlaArgLysGlnValProGlyGluAspGlyArgPro

1072 ACCCAACTACCCAATGTCATTGACGAGACTTTCCCCTTGACCCGTCCCAACTGGGATTTTGCT
358▶ThrGlnLeuProAsnValIleAspGluThrPheProLeuThrArgProAsnTrpAspPheAla

1135 ACGCCGGCAGGTAGGGAGCACCTACGCCTTTATCGCCAGTTGCTATTAGCGGGTCTCCGCGGG
379▶ThrProAlaGlyArgGluHisLeuArgLeuTyrArgGlnLeuLeuLeuAlaGlyLeuArgGly
```

Figure No. 5

```
1198 GCTGCAAGACGCCCCACTAATTTGGCACAGGTAAAGCAGGTTGTACAAGGGAAAGAGGAAACG
 400▶AlaAlaArgArgProThrAsnLeuAlaGlnValLysGlnValValGlnGlyLysGluGluThr

1261 CCAGCAGCATTTTTAGAAAGATTAAAAGAGGCTTATAGAATGTACACTCCCTATGACCCTGAG
 421▶ProAlaAlaPheLeuGluArgLeuLysGluAlaTyrArgMetTyrThrProTyrAspProGlu

1324 GACCCAGGGCAAGCGGCTAGTGTTATCCTATCCTTTATATACCAGTCTAGCCCAGATATAAGA
 442▶AspProGlyGlnAlaAlaSerValIleLeuSerPheIleTyrGlnSerSerProAspIleArg

1387 AATAAGTTACAAAGGCTAGAAGGCCTACAAGGGTTCACCCTATCTGATCTGCTAAAAGAGGCA
 463▶AsnLysLeuGlnArgLeuGluGlyLeuGlnGlyPheThrLeuSerAspLeuLeuLysGluAla

1450 GAAAAGATATACAACAAAAGGGAGACCCCAGAGGAAAGGGAAGAAAGATTATGGCAGCGACAG
 484▶GluLysIleTyrAsnLysArgGluThrProGluGluArgGluGluArgLeuTrpGlnArgGln

1513 GAAGAAAGAGATAAAAAGCGCCACAAGGAGATGACTAAAGTTCTGGCCACAGTAGTTGCTCAG
 505▶GluGluArgAspLysLysArgHisLysGluMetThrLysValLeuAlaThrValValAlaGln

1576 AATAGAGATAAGGATAGAGAAGAAAGTAAACTGGGGGATCAAAGGAAAATACCTCTGGGGAAA
 526▶AsnArgAspLysAspArgGluGluSerLysLeuGlyAspGlnArgLysIleProLeuGlyLys

1639 GACCAGTGTGCCTATTGCAAGGAAAAGGGGCATTGGGTTCGCGATTGCCCCAAACGACCCAGG
 547▶AspGlnCysAlaTyrCysLysGluLysGlyHisTrpValArgAspCysProLysArgProArg

1702 AAGAAACCCGCCAACTCCACTCTCCTCAACTTAGGAGATTAGGAGAGTCAGGGCCAGGACCCC
 568▶LysLysProAlaAsnSerThrLeuLeuAsnLeuGlyAsp•••
                                         1▶GluIleArgArgValArgAlaArgThrPr

1765 CCCCCCTGAGCCCAGGATAACCTTAAAAATAGGGGGGCAACCGGTGACTTTTCTGGTGGACAC
  10▶oProProGluProArgIleThrLeuLysIleGlyGlyGlnProValThrPheLeuValAspTh

1828 GGGAGCCCAGCACTCAGTACTGACTCGACCAGATGGACCTCTCAGTGACCGCACAGCCCTGGT
  31▶rGlyAlaGlnHisSerValLeuThrArgProAspGlyProLeuSerAspArgThrAlaLeuVa

1891 GCAAGGAGCCACGGGAAGCAAAAACTACCGGTGGACCACCGACAGGAGGGTACAACTGGCAAC
  52▶lGlnGlyAlaThrGlySerLysAsnTyrArgTrpThrThrAspArgArgValGlnLeuAlaTh

1954 CGGTAAGGTGACTCATTCTTTTTTATATGTACCTGAATGTCCCTACCCGTTATTAGGGAGAGA
  73▶rGlyLysValThrHisSerPheLeuTyrValProGluCysProTyrProLeuLeuGlyArgAs

2017 CCTATTAACTAAACTTAAGGCCCAAATCCATTTTACCGGAGAAGGGGCTAATGTTGTTGGGCC
  94▶pLeuLeuThrLysLeuLysAlaGlnIleHisPheThrGlyGluGlyAlaAsnValValGlyPr

2080 CAGGGGTTTACCCCTACAAGTCCTTACTTTACAATTAGAAGAGGAGTATCGGCTATTTGAGCC
 115▶oArgGlyLeuProLeuGlnValLeuThrLeuGlnLeuGluGluGluTyrArgLeuPheGluPr

2143 AGAAAGTACACAAAAACAGGAGATGGACACTTGGCTTAAAAACTTTCCCCAGGCGTGGGCAGA
 136▶oGluSerThrGlnLysGlnGluMetAspThrTrpLeuLysAsnPheProGlnAlaTrpAlaGl
```

Figure No. 5 (continuation)

```
2206 AACAGGAGGTATGGGAATGGCTCATTGTCAAGCCCCGTTCTCATTCAACTTAAGGCTACTGC
157▶ uThrGlyGlyMetGlyMetAlaHisCysGlnAlaProValLeuIleGlnLeuLysAlaThrAl

2269 CACTCCAATCTCCATCCGACAGTATCCTATGCCCCATGAAGCGTACCAGGGAATTAAGCCTCA
178▶ aThrProIleSerIleArgGlnTyrProMetProHisGluAlaTyrGlnGlyIleLysProHi

2332 TATAAGAAGAATGCTAGATCAAGGCATCCTCAAGCCCTGCCAGTCCCCATGGAATACACCCTT
199▶ sIleArgArgMetLeuAspGlnGlyIleLeuLysProCysGlnSerProTrpAsnThrProLe

2395 ATTACCTGTTAAGAAGCCAGGGACCGAGGATTACAGACCAGTGCAGGACTTAAGAGAAGTAAA
220▶ uLeuProValLysLysProGlyThrGluAspTyrArgProValGlnAspLeuArgGluValAs

2458 CAAAAGAGTAGAAGACATCCATCCTACTGTGCCAAATCCATATAACCTCCTTAGCACCCTCCC
241▶ nLysArgValGluAspIleHisProThrValProAsnProTyrAsnLeuLeuSerThrLeuPr

2521 GCCGTCTCACCCTTGGTACACTGTCCTAGATTTAAAGGACGCTTTTTTCTGCCTGCGACTACA
262▶ oProSerHisProTrpTyrThrValLeuAspLeuLysAspAlaPhePheCysLeuArgLeuHi

2584 CTCTGAGAGTCAGTTACTTTTTGCATTTGAATGGAGAGATCCAGAAATAGGACTGTCAGGGCA
283▶ sSerGluSerGlnLeuLeuPheAlaPheGluTrpArgAspProGluIleGlyLeuSerGlyGl

2647 ACTAACCTGGACACGCCTTCCTCAGGGGTTCAAGAATAGCCCCACCCTATTTGATGAGGCCCT
304▶ nLeuThrTrpThrArgLeuProGlnGlyPheLysAsnSerProThrLeuPheAspGluAlaLe

2710 GCACTCAGACCTGGCCGATTTCAGGGTAAGGTACCCGGCTCTAGTCCTCCTACAATATGTAGA
325▶ uHisSerAspLeuAlaAspPheArgValArgTyrProAlaLeuValLeuLeuGlnTyrValAs

2773 TGACCTCTTGCTGGCTGCGGCAACCAGGACTGAATGCCTGGAAGGGACTAAGGCACTCCTTGA
346▶ pAspLeuLeuLeuAlaAlaAlaThrArgThrGluCysLeuGluGlyThrLysAlaLeuLeuGl

2836 GACTTTGGGCAATAAGGGGTACCGAGCCTCTGGAAAGAAGGCCCAAATTTGCCTGCAAGAAGT
367▶ uThrLeuGlyAsnLysGlyTyrArgAlaSerGlyLysLysAlaGlnIleCysLeuGlnGluVa

2899 CACATACCTGGGGTACTCTTTAAAAGATGGCCAAAGCTGGCTTACCAAAGCTCGGAAAGAAGC
388▶ lThrTyrLeuGlyTyrSerLeuLysAspGlyGlnArgTrpLeuThrLysAlaArgLysGluAl

2962 CATCCTATCCATCCCTGTGCCTAAAAACCCACGACAAGTGAGAGAGTTCCTTGGAACTGCAG
409▶ aIleLeuSerIleProValProLysAsnProArgGlnValArgGluPheLeuGlyThrAla
```

Figure No. 5 (continuation and end)

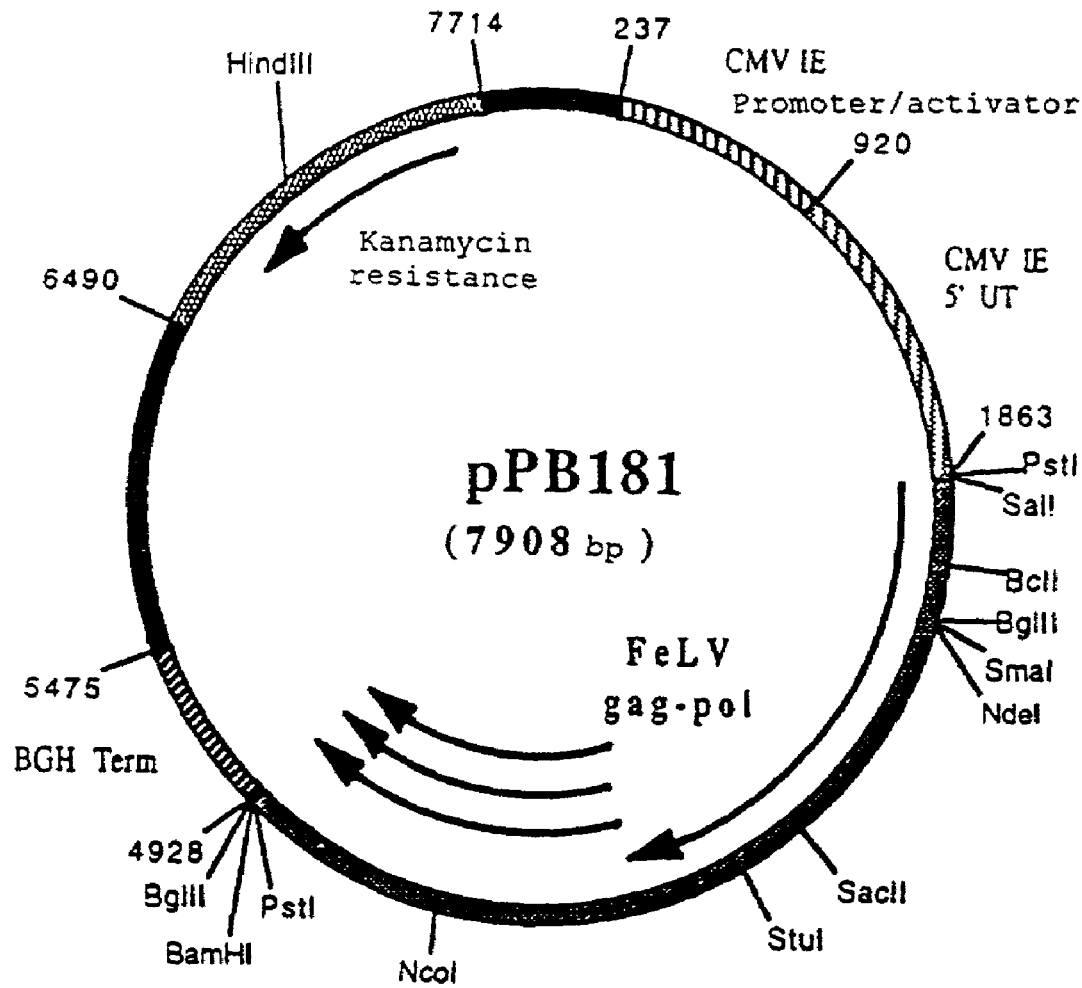
Figure No. 6

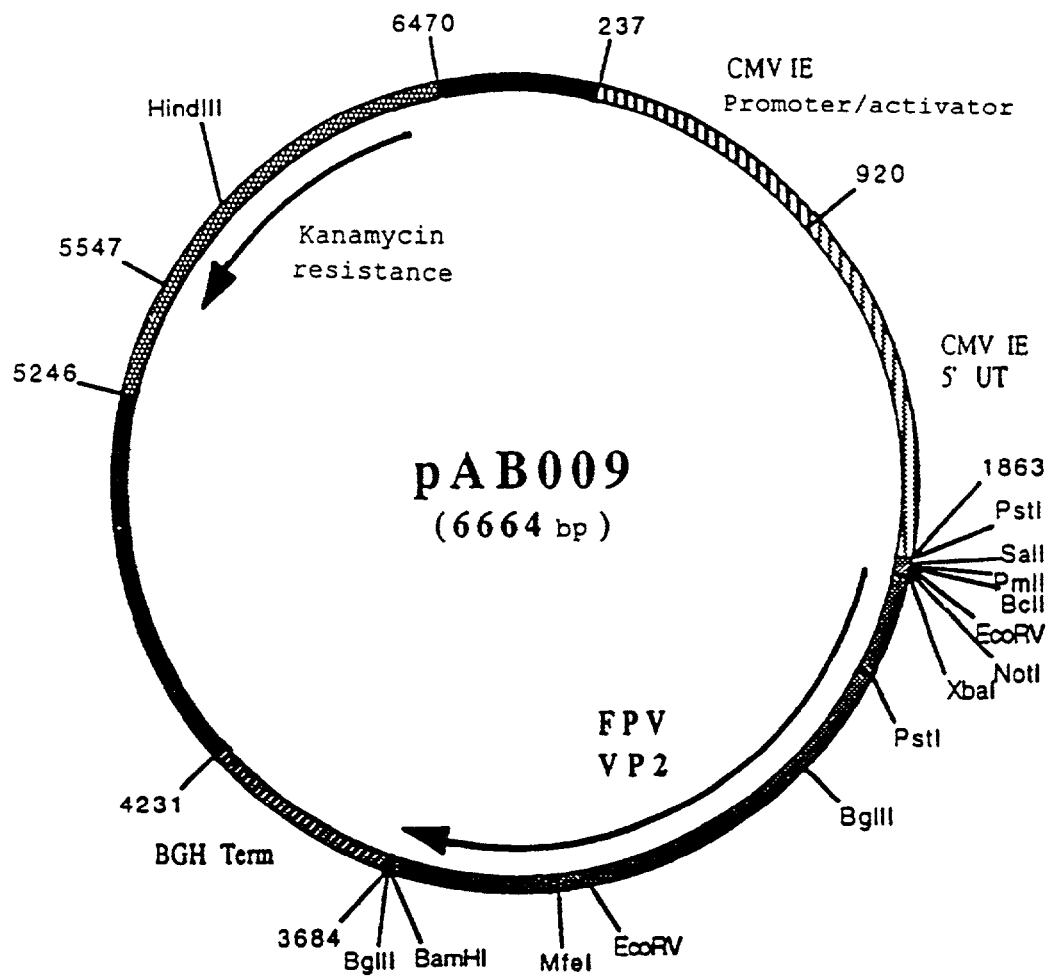
Figure No. 7

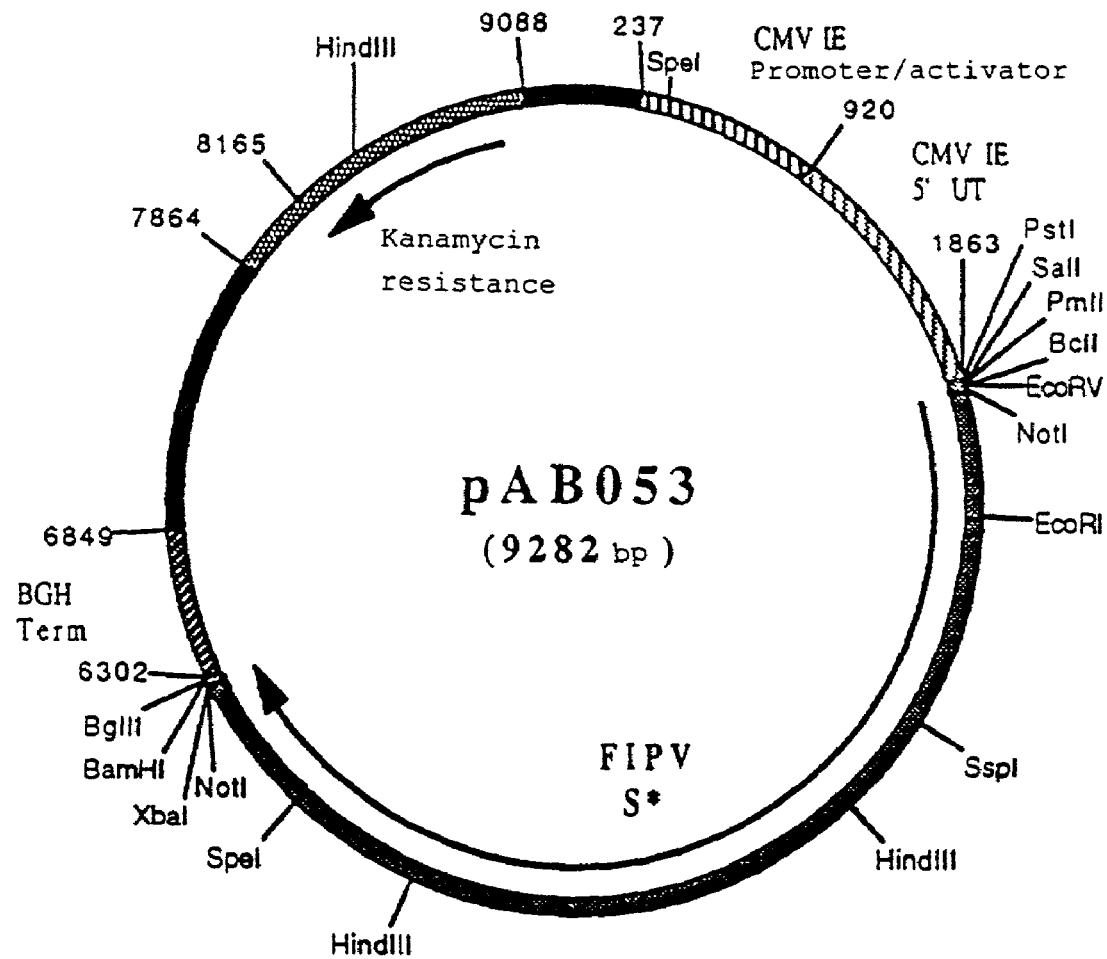
Figure No. 8

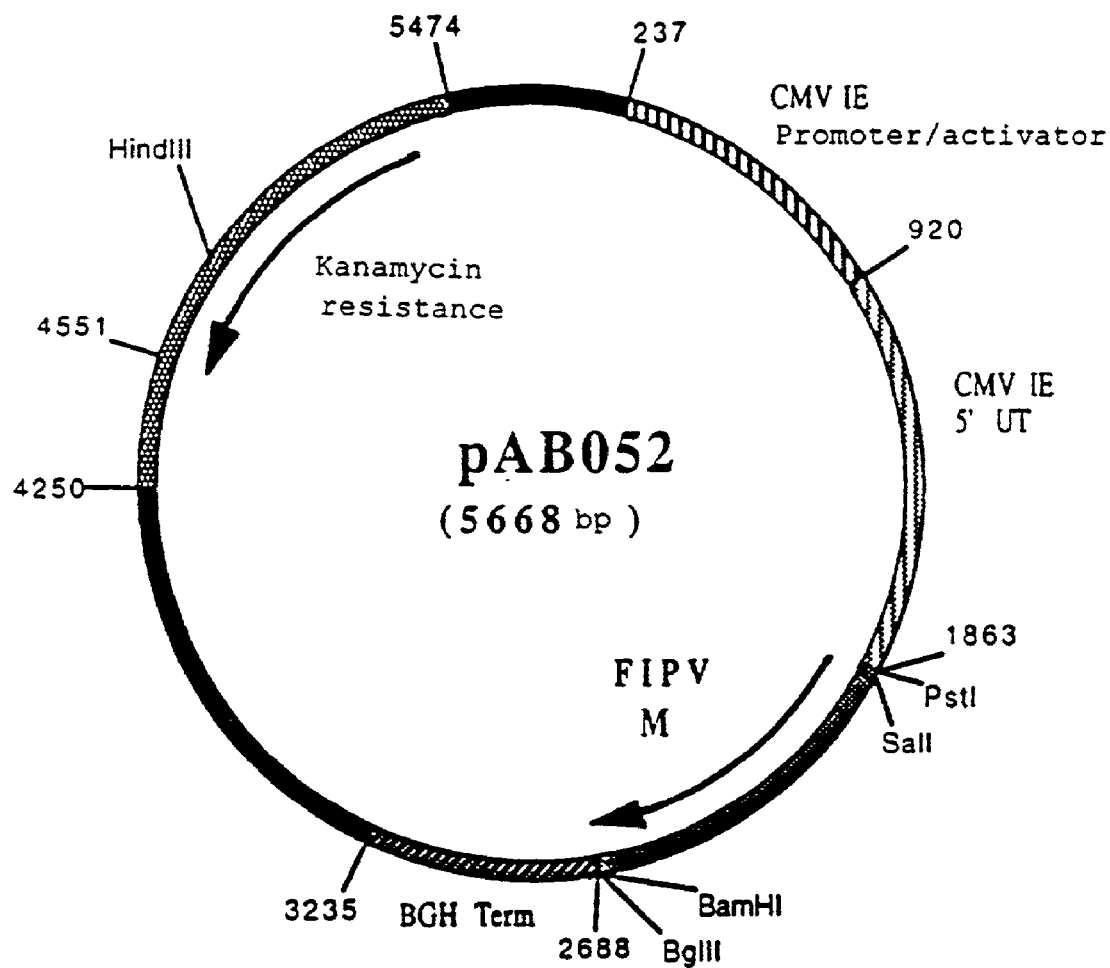
Figure No. 9

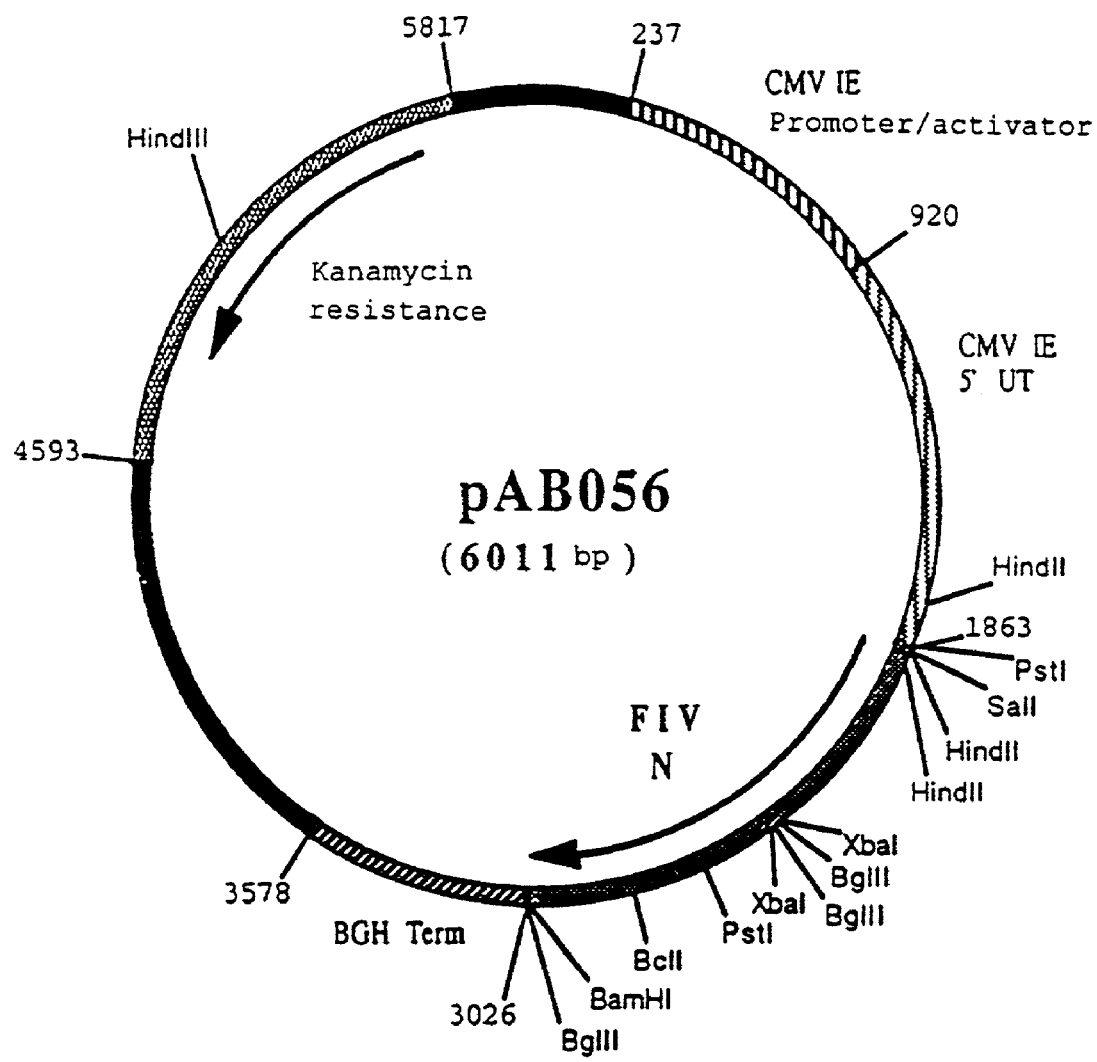
Figure No. 10

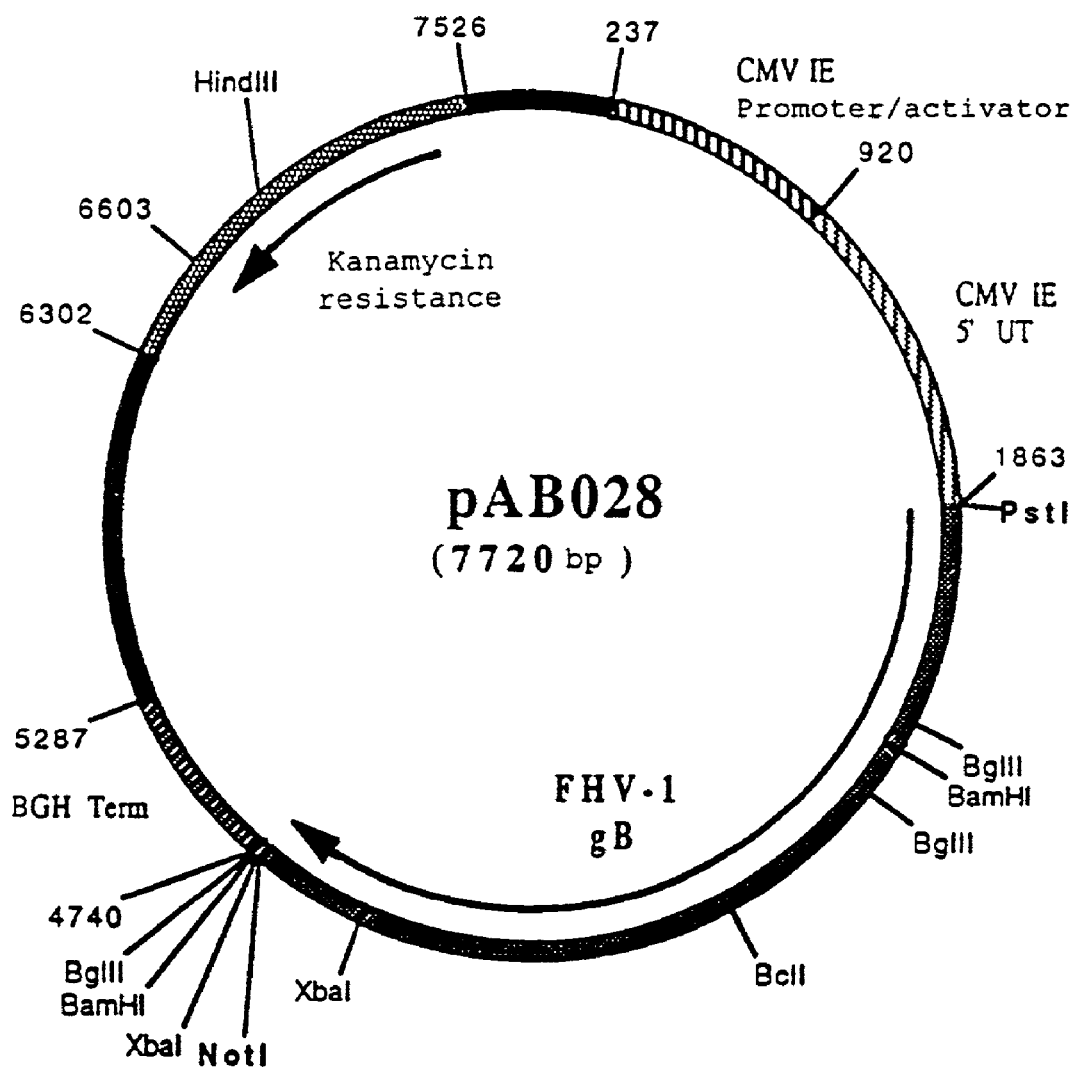
Figure No. 11

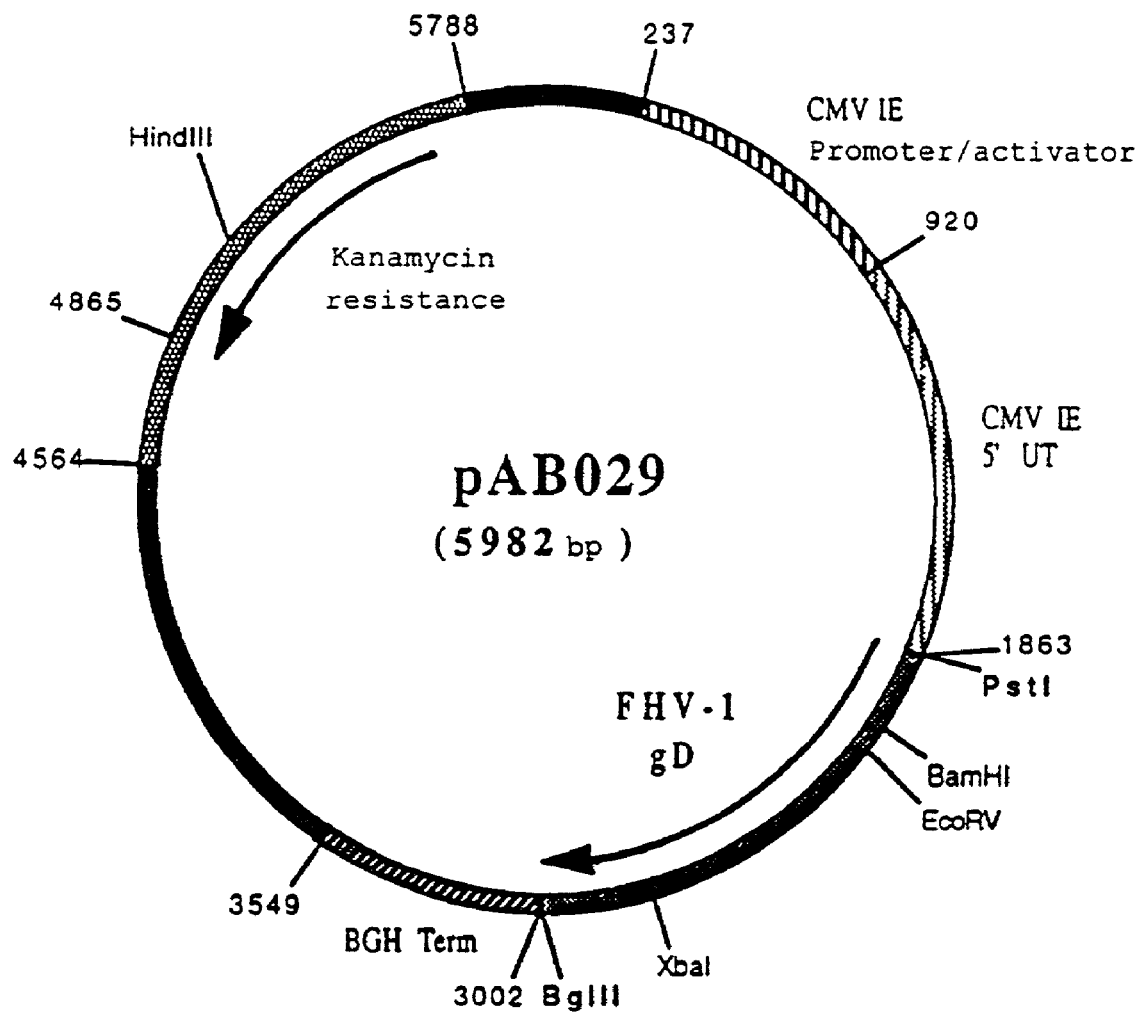
Figure No. 12

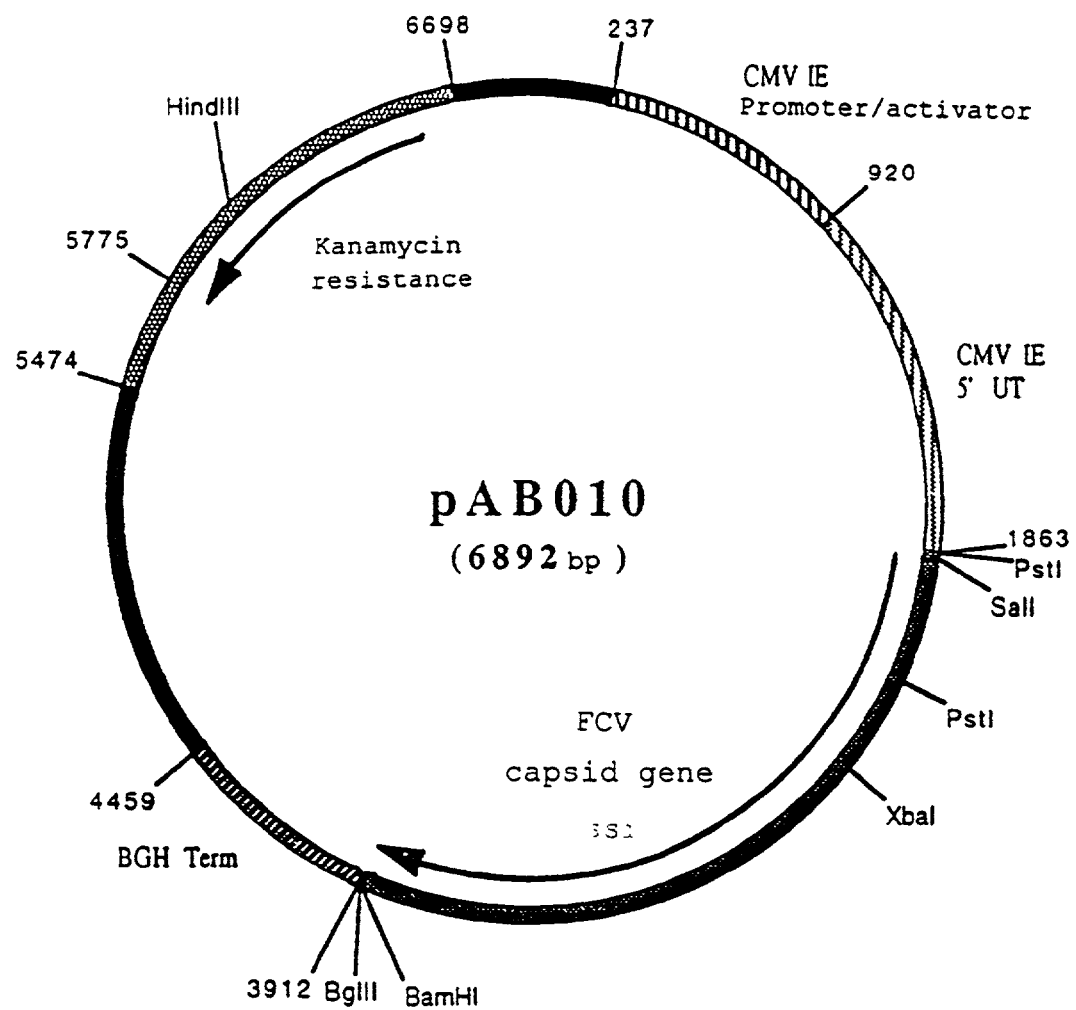
Figure No. 13

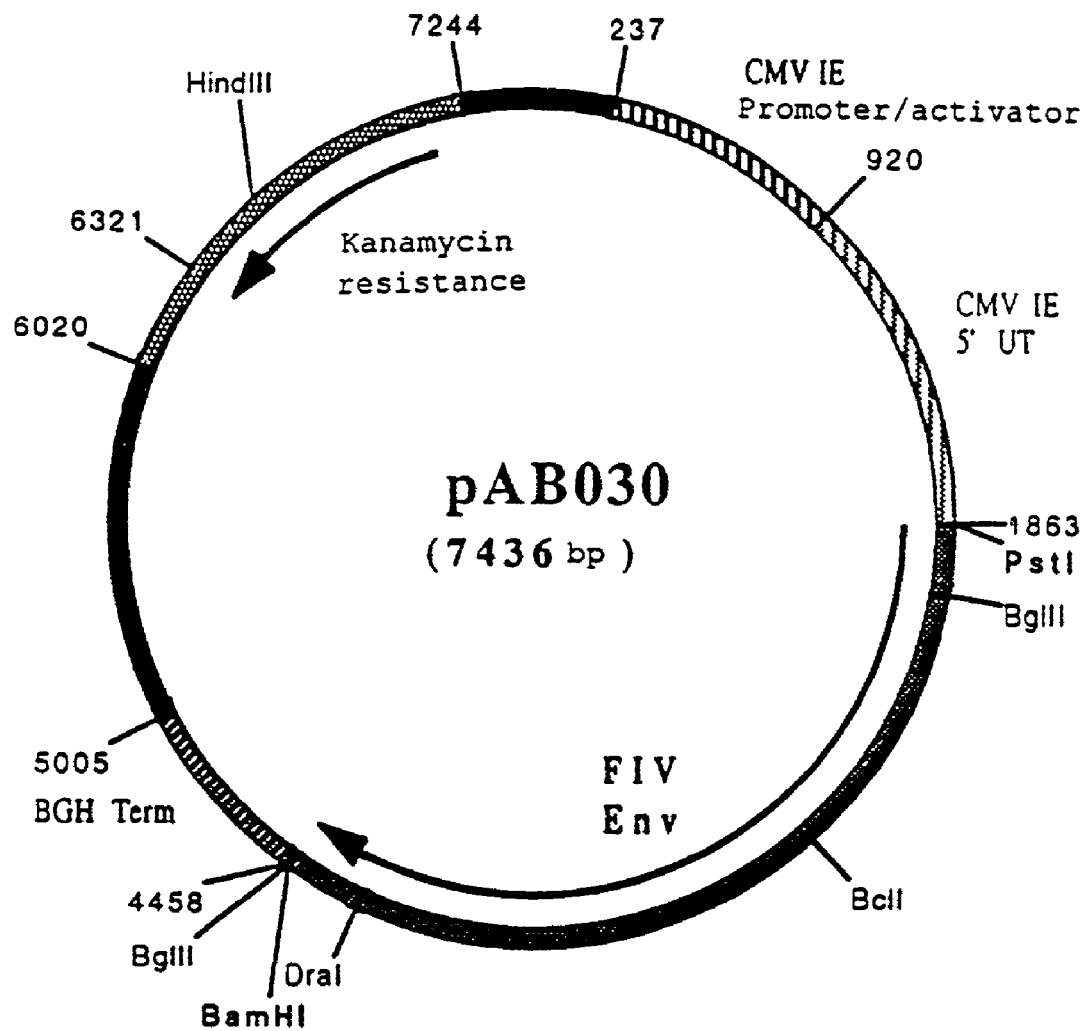
Figure No. 14

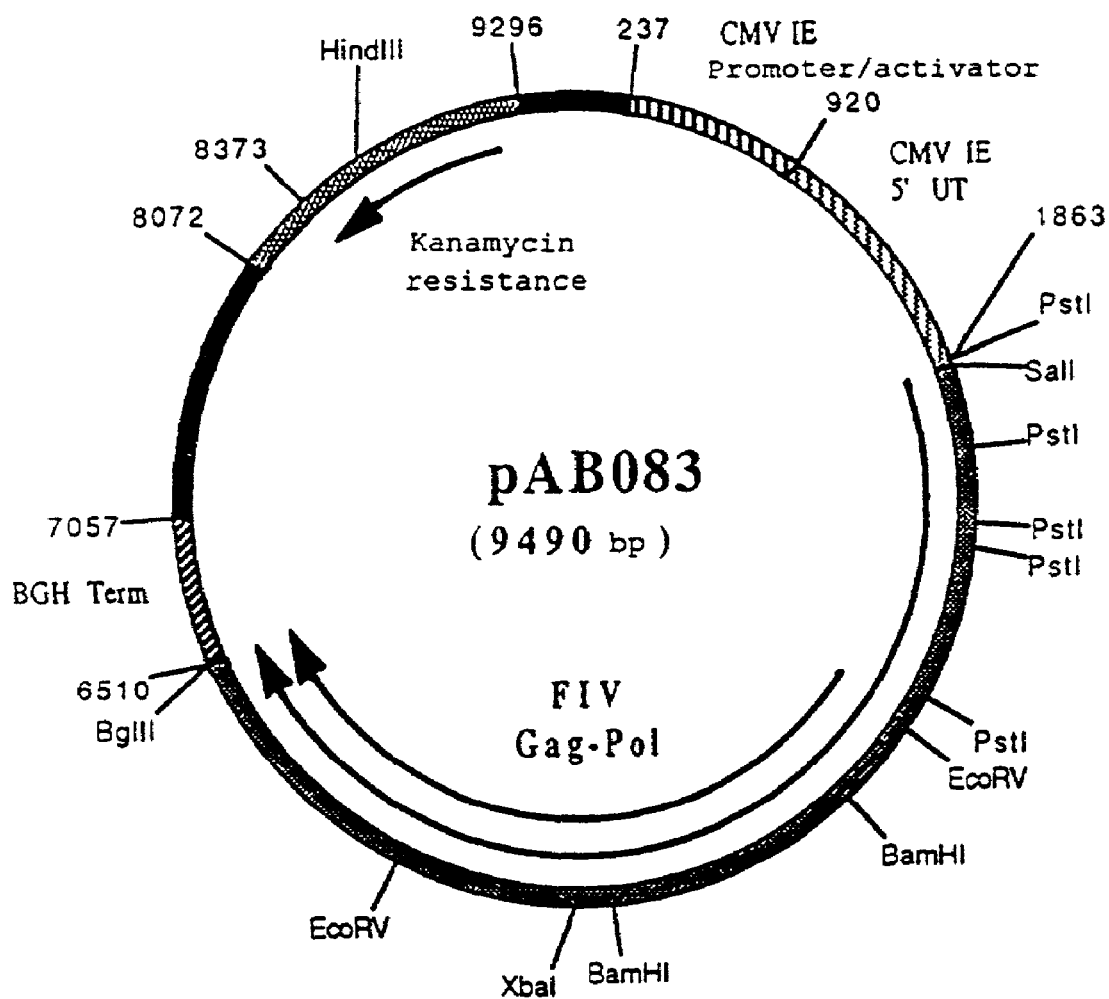
Figure No. 15

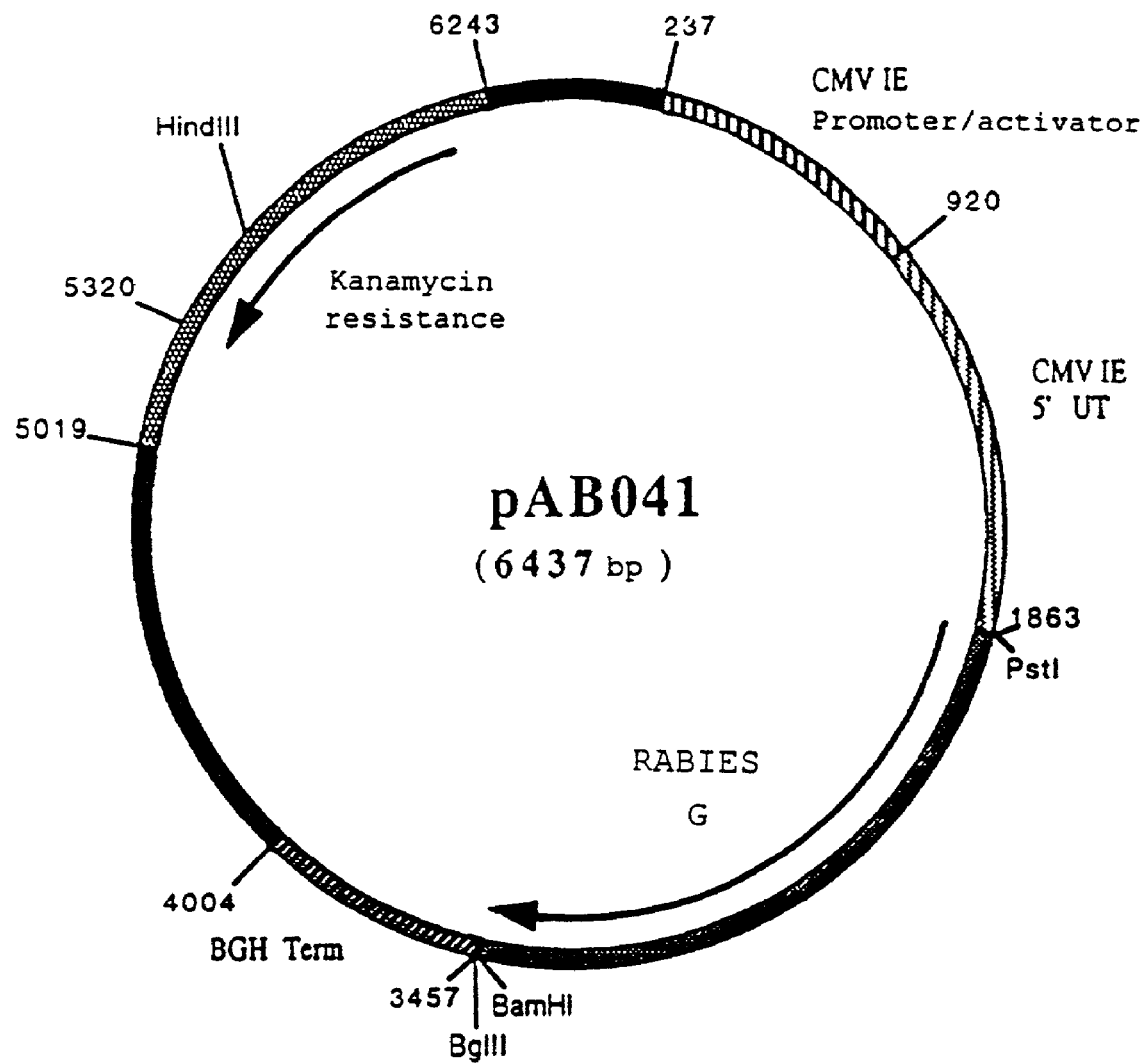
Figure No. 16

FELINE POLYNUCLEOTIDE VACCINE FORMULA

This application is a divisional of prior application Ser. No. 09/232,278, filed Jan. 15, 1999 now U.S. Pat. No. 6,348,196 which is a continuation-in-part of copending International Application PCT/FR97/01315 having an international filing date of 15 Jul. 1997, and designating the U.S. and claiming priority from French Application No. 96/09337, filed 19 Jul. 1996.

Reference is also made to the applications of Audonnet et al., Ser. Nos 09/232,468, 09/232,477, 09/232,279, 09/232,479, and 09/232,478 and to the application of Rijsewijk et al. Ser. No. 09/232,469, all filed Jul. 19, 1996. All of the above-mentioned applications, as well as all documents cited herein and documents referenced or cited in documents cited herein, are hereby incorporated herein by reference. Vectors of vaccines or immunological compositions of the aforementioned applications, as well as of documents cited herein or documents referenced or cited in documents cited herein or portions of such vectors (e.g., one or more or all of regulatory sequences such as DNA for promoter, leader for secretion, terminator), may to the extent practicable with respect to the preferred host of this application, also be employed in the practice of this invention; and, DNA for vectors of vaccines or immunological compositions herein can be obtained from available sources and knowledge in the art, e.g., GeneBank, such that from this disclosure, no undue experimentation is required to make or use such vectors.

The present invention relates to a vaccine formula allowing the vaccination of cats against a number of pathologies. It also relates to a corresponding method of vaccination.

Associations of vaccines against certain feline viruses have already been proposed in the past.

The associations developed so far were prepared from inactivated vaccines or live vaccines and, optionally, mixtures of such vaccines. Their development poses problems of compatibility between valencies and of stability. It is indeed necessary to ensure both the compatibility between the different vaccine valencies, whether from the point of view of the different antigens used or from the point of view of the formulations themselves, especially in the case where both inactivated vaccines and live vaccines are combined. The problem of the conservation of such combined vaccines and of their safety especially in the presence of an adjuvant also exists. These vaccines are in general quite expensive.

Patent Applications WO-A-90 11092, WO-A-93 19183, WO-A-94 21797 and WO-A-95 20660 have made use of the recently developed technique of polynucleotide vaccines. It is known that these vaccines use a plasmid capable of expressing, in the host cells, the antigen inserted into the plasmid. All the routes of administration have been proposed (intraperitoneal, intravenous, intramuscular, transcutaneous, intradermal, mucosal and the like). Various vaccination means can also be used, such as DNA deposited at the surface of gold particles and projected so as to penetrate into the animal' skin (Tang et al., Nature 356, 152-154, 1992) and liquid jet injectors which make it possible to transfect at the same time the skin, the muscle, the fatty tissues and the mammary tissues (Furth et al., Analytical Biochemistry, 205, 365-368, 1992).

(See also U.S. Pat. Nos. 5,846,946, 5,620,896, 5,643,578, 5,580,589, 5,589,466, 5,693,622, and 5,703,055; Science, 259:1745-49, 1993; Robinson et al., seminars in IMMUNOLOGY, 9:271-83, 1997; Luke et al., J. Infect. Dis. 175(1): 91-97, 1997; Norman et al., Vaccine, 15(8):801-803, 1997; Bourne et al., The Journal of Infectious Disease, 173:800-7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.)

The polynucleotide vaccines may also use both naked DNAs and DNAs formulated, for example, inside cationic lipids or liposomes.

The invention therefore proposes to provide a multivalent vaccine formula which makes it possible to ensure vaccination against a number of feline pathogenic viruses.

Another objective of the invention is to provide such a vaccine formula combining different valencies while exhibiting all the criteria required for mutual compatibility and stability of the valencies.

Another objective of the invention is to provide such a vaccine formula which makes it possible to combine different valencies in the same vehicle.

Another objective of the invention is to provide such a vaccine which is easy and inexpensive to use.

Yet another objective of the invention is to provide a method for vaccinating cats which makes it possible to obtain protection, including multivalent protection, with a high level of efficiency and of long duration, as well as good safety.

The subject of the present invention is therefore a vaccine formula intended for cats, comprising at least three polynucleotide vaccine valencies each comprising a plasmid integrating, so as to express it in vivo in the host cells, a gene with one feline pathogen valency, these valencies being selected from those of the group consisting of feline leukaemia virus (FeLV) panleukopenia virus (FPV), infectious peritonitis virus (FIPV), coryza virus (FHV), calicivirosis virus (FCV), feline immunodeficiency virus (FIV) and possibly rabies virus (rhabdovirus), the plasmids comprising, for each valency, one or more of the genes selected from the group consisting of env and gag/pol for the feline leukaemia, VP2 for the panleukopenia, modified S (or S*) and M for the infectious peritonitis, gB and gD for the coryza, capsid for the calicivirosis, env and gag/pro for the feline immunodeficiency and G for the rabies.

Valency in the present invention is understood to mean at least one antigen providing protection against the virus for the pathogen considered, it being possible for the valency to contain, as subvalency, one or more modified or natural genes from one or more strains of the pathogen considered.

Pathogenic agent gene is understood to mean not only the complete gene but also the various nucleotide sequences, including fragments which retain the capacity to induce a protective response. The notion of a gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but encoding the same protein.

Preferably, the vaccine formula according to the invention comprises the panleukopenia, coryza and calicivirosis valencies.

It will be possible to add the feline leukaemia, feline immunodeficiency and/or infectious peritonitis valencies.

As regards the coryza valency, it is preferable to use the two genes coding for gB and gD, in different plasmids or in one and the same plasmid, or to use either of these genes.

For the feline leukaemia valency, use is preferably made of the two env and gag/pol genes integrated into two different plasmids or into one and the same plasmid, or the env gene alone.

For the feline immunodeficiency valency, use will preferably be made of the two env and gag/pro genes in different plasmids or in one and the same plasmid, or only one of these genes. Still more preferably, the FeLV-A env gene and the FeLV-A and FeLV-B env genes are used.

For the infectious peritonitis valency, use is preferably made of the two M and modified S genes together in two different plasmids or in one and the same plasmid, or either of these genes. S will be modified in order to make the major facilitating epitopes inactive, preferably according to the teaching of Patent PCT/FR95/01128.

The vaccine formula according to the invention can be presented in a dose volume of between 0.1 and 3 ml and in particular between 0.5 and 1 ml.

The dose will be generally between 10 ng and 1 mg, preferably between 100 ng and 500 μg and still more preferably between 1 μg and 250 μg per plasmid type.

Use will preferably be made of naked plasmids simply placed in the vaccination vehicle which will be in general physiological saline (0.9% NaCl), ultrapure water, TE buffer and the like. All the polynucleotide vaccine forms described in the prior art can of course be used.

Each plasmid comprises a promoter capable of ensuring the expression of the gene inserted, under its control, into the host cells. This will be in general a strong eukaryotic promoter and in particular a cytomegalovirus early CMV-IE promoter of human or murine origin, or optionally of another origin such as rats, pigs and guinea pigs.

More generally, the promoter may be either of viral origin or of cellular origin. As viral promoter, there may be mentioned the SV40 virus early or late promoter or the Rous sarcoma virus LTR promoter. It may also be a promoter from the virus from which the gene is derived, for example the gene's own promoter.

As cellular promoter, there may be mentioned the promoter of a cytoskeleton gene, such as for example the desmin promoter (Bolmont et al., Journal of Submicroscopic Cytology and Pathology, 1990, 22, 117-122; and Zhenlin et al., Gene, 1989, 78, 243-254), or alternatively the actin promoter.

When several genes are present in the same plasmid, these may be presented in the same transcription unit or in two different units.

The combination of the different vaccine valencies according to the invention may be preferably achieved by mixing the polynucleotide plasmids expressing the antigen(s) of each valency, but it is also possible to envisage causing antigens of several valencies to be expressed by the same plasmid.

The subject of the invention is also monovalent vaccine formulae comprising one or more plasmids encoding one or more genes from one of the viruses above, the genes being those described above. Besides their monovalent character, these formulae may possess the characteristics stated above as regards the choice of the genes, their combinations, the composition of the plasmids, the dose volumes, the doses and the like.

The monovalent vaccine formulae may also be used (i) for the preparation of a polyvalent vaccine formula as described above, (ii) individually against the actual pathology, (iii) combined with a vaccine of another type (live or inactivated whole, recombinant, subunit) against another pathology, or (iv) as booster for a vaccine as described below.

The subject of the present invention is in fact also the use of one or more plasmids according to the invention for the manufacture of a vaccine intended to vaccinate cats first vaccinated by means of a first conventional vaccine (monovalent or multivalent) of the type in the prior art, in particular, selected from the group consisting of a live whole vaccine, an inactivated whole vaccine, a subunit vaccine, a recombinant vaccine, this first vaccine having (that is to say containing or capable of expressing) the antigen(s) encoded by the plasmid(s) or antigen(s) providing cross-protection.

Remarkably, the polynucleotide vaccine has a potent booster effect which results in an amplification of the immune response and the acquisition of a long-lasting immunity.

In general, the first-vaccination vaccines can be selected from commercial vaccines available from various veterinary vaccine producers.

The subject of the invention is also a vaccination kit grouping together a first-vaccination vaccine as described above and a vaccine formula according to the invention for the booster. It also relates to a vaccine formula according to the invention accompanied by a leaflet indicating the use of this formula as a booster for a first vaccination as described above.

The subject of the present invention is also a method for vaccinating cats, comprising the administration of an effective vaccine formula as described above. This vaccination method comprises the administration of one or more doses of the vaccine formula, it being possible for these doses to be administered in succession over a short period of time and/or in succession at widely spaced intervals.

The vaccine formulae according to the invention can be administered in the context of this method of vaccination, by the different routes of administration proposed in the prior art for polynucleotide vaccination and by means of known techniques of administration.

The subject of the invention is also the method of vaccination consisting in making a first vaccination as described above and a booster with a vaccine formula according to the invention.

In a preferred embodiment of the process according to the invention, there is administered in a first instance, to the animal, an effective dose of the vaccine of the conventional, especially inactivated, live, attenuated or recombinant, type, or alternatively a subunit vaccine, so as to provide a first vaccination, and, after a period preferably of 2 to 6 weeks, the polyvalent or monovalent vaccine according to the invention is administered.

The efficiency of presentation of the antigens to the immune system varies according to the tissues. In particular, the mucous membranes of the respiratory tree serve as barrier to the entry of pathogens and are associated with lymphoid tissues which support local immunity. The administration of a vaccine by contact with the mucous membranes, in particular the buccal mucous membrane, the pharyngeal mucous membrane and the mucous membrane of the bronchial region is certainly of interest for vaccination against respiratory and digestive pathologies.

Consequently, the mucosal routes of administration form part of a preferred mode of administration for the invention, using in particular nebulization or spray or drinking water. It will be possible to apply the vaccine formulae and the vaccination methods according to the invention in this context.

The invention also relates to the method of preparing the vaccine formulae, namely the preparation of the valencies and mixtures thereof, as evident from this description.

The invention will now be described in greater detail with the aid of the embodiments of the invention taken with reference to the accompanying drawings.

BRIEF DESCRIPTION OF THE DRAWINGS

FIG. 1: Plasmid pVR1012
FIG. 2: Plasmid pPB179
FIG. 3: Sequence of the FeLV-B env gene (SEQ ID NO: 5)
FIG. 4: Plasmid pPB180
FIG. 5: Sequence of the FeLV-A virus gag/pol gene (Glasgow-1 strain) (SEQ ID NO: 8)
FIG. 6: Plasmid pPB181
FIG. 7: Plasmid pAB009
FIG. 8: Plasmid pAB053
FIG. 9: Plasmid pAB052
FIG. 10: Plasmid pAB056
FIG. 11: Plasmid pAB028
FIG. 12: Plasmid pAB029
FIG. 13: Plasmid pAB010
FIG. 14: Plasmid pAB030
FIG. 15: Plasmid pAB083
FIG. 16: Plasmid pAB041

Sequence Listing SEQ ID No.
SEQ ID No. 1: Oligonucleotide PB247
SEQ ID No. 2: Oligonucleotide PB249
SEQ ID No. 3: Oligonucleotide PB281
SEQ ID No. 4: Oligonucleotide PB282
SEQ ID No. 5: Sequence of the FeLV-B virus env gene
SEQ ID No. 6: Oligonucleotide PB283
SEQ ID No. 7: Oligonucleotide PB284
SEQ ID No. 8: Sequence of the FeLV-A virus gag/pol gene (Glasgow-1 strain)
SEQ ID No. 9: Oligonucleotide AB021
SEQ ID No. 10: Oligonucleotide AB024
SEQ ID No. 11: Oligonucleotide AB103
SEQ ID No. 12: Oligonucleotide AB112
SEQ ID No. 13: Oligonucleotide AB113
SEQ ID No. 14: Oligonucleotide AB104
SEQ ID No. 15: Oligonucleotide AB101
SEQ ID No. 16: Oligonucleotide AB102
SEQ ID No. 17: Oligonucleotide AB106
SEQ ID No. 18: Oligonucleotide AB107
SEQ ID No. 19: Oligonucleotide AB061
SEQ ID No. 20: Oligonucleotide AB064
SEQ ID No. 21: Oligonucleotide AB065
SEQ ID No. 22: Oligonucleotide AB066
SEQ ID No. 23: Oligonucleotide AB025
SEQ ID No. 24: Oligonucleotide AB026
SEQ ID No. 25: Oligonucleotide AB067
SEQ ID No. 26: Oligonucleotide AB070
SEQ ID No. 27: Oligonucleotide AB154
SEQ ID No. 28: Oligonucleotide AB155
SEQ ID No. 29: Oligonucleotide AB011
SEQ ID No. 30: Oligonucleotide AB012

EXAMPLES

Example 1

Culture of the Viruses

The viruses are cultured on the appropriate cellular system until a cytopathic effect is obtained. The cellular systems to be used for each virus are well known to persons skilled in the art. Briefly, the cells sensitive to the virus used, which are cultured in Eagle's minimum essential medium (MEM medium) or another appropriate medium, are inoculated with the viral strain studied using a multiplicity of infection of 1. The infected cells are then incubated at 37° C. for the time necessary for the appearance of a complete cytopathic effect (on average 36 hours).

Example 2

Extraction of the Viral Genomic DNAs

After culturing, the supernatant and the lysed cells are harvested and the entire viral suspension is centrifuged at 1000 g for 10 minutes at +4° C. so as to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 µg/ml final) in the presence of sodium dodecyl sulphate (SDS) (0.5% final) for 2 hours at 37° C. The viral DNA is then extracted with a phenol/chloroform mixture and then precipitated with 2 volumes of absolute ethanol. After leaving overnight at −20° C., the DNA is centrifuged at 10,000 g for 15 minutes at +4° C. The DNA pellet is dried and then taken up in a minimum volume of sterile ultrapure water. It can then be digested with restriction enzymes.

Example 3

Isolation of the Viral Genomic RNAs

The RNA viruses were purified according to techniques well known to persons skilled in the art. The genomic viral RNA of each virus was then isolated using the "guanidium thiocyanate/phenol-chloroform" extraction technique described by P. Chomczynski and N. Sacchi (Anal. Biochem., 1987, 162, 156-159).

Example 4

Molecular Biology Techniques

All the constructions of plasmids were carried out using the standard molecular biology techniques described by J. Sambrook et al. (*Molecular Cloning: A Laboratory Manual*, 2nd Edition, Cold Spring Harbor Laboratory, Cold Spring Harbor, N.Y., 1989). All the restriction fragments used for the present invention were isolated using the "Geneclean" kit (BIO 101 Inc. La Jolla, Calif.).

Example 5

RT-PCR Technique

Specific oligonucleotides (comprising restriction sites at their 5' ends to facilitate the cloning of the amplified fragments) were synthesized such that they completely cover the coding regions of the genes which are to be amplified (see specific examples). The reverse transcription (RT) reaction and the polymerase chain reaction (PCR) were carried out according to standard techniques (Sambrook J. et al., 1989). Each RT-PCR reaction was performed with a pair of specific amplimers and taking, as template, the viral genomic RNA extracted. The complementary DNA amplified was extracted with phenol/chloroform/isoamyl alcohol (25:24:1) before being digested with restriction enzymes.

Example 6

Plasmid pVR1012

The plasmid pVR1012 (FIG. 1) was obtained from Vical Inc., San Diego, Calif., USA. Its construction has been described in J. Hartikka et al. (Human Gene Therapy, 1996, 7, 1205-1217).

Example 7

Construction of the Plasmid pPB179 (FeLV-A Virus Env Gene)

An RT-PCR reaction according to the technique of Example 5 was carried out with feline leukaemia virus (FeLV-A) (Glasgow-1 strain) genomic RNA (M. Stewart et al. J. Virol. 1986. 58. 825-834), prepared according to the technique of Example 3, and with the following oligonucleotides:

```
PB247 (29 mer) (SEQ ID No. 1)
5'TTTGTCGACCATGGAAAGTCCAACGCACC3'

PB249 (28 mer) (SEQ ID No. 2)
5'TTTGGATCCTCATGGTCGGTCCGGATCG3'
``` so as to amplify a 1947 bp fragment containing the gene encoding the Env glycoprotein from the FeLV-A virus (Glasgow-1 strain) in the form of a SalI-BamHI fragment. After purification, the RT-PCR product was digested with SalI and BamHI in order to give a 1935 bp SalI-BamHI fragment.

This fragment was ligated with the vector pVR1012 (Example 6), previously digested with SalI and BamHI, to give the plasmid pPB179 (6804 bp) (FIG. 2).

Example 8

Construction of the Plasmid pPB180 (FeLV-B Virus Env Gene)

An RT-PCR reaction according to the technique of Example 5 was carried out with feline leukaemia virus (FeLV-B subtype) genomic RNA, prepared according to the technique of Example 3, and with the following oligonucleotides:

```
PB281 (29 mer) (SEQ ID No. 3)
5'TTTGTCGACATGGAAGGTCCAACGCACCC3'

PB282 (32 mer) (SEQ ID No. 4)
5'TTGGATCCTCATGGTCGGTCCGGATCATATTG3'
``` so as to amplify a 2005 bp fragment containing the gene encoding the Env glycoprotein from the FeLV-B virus (FIG. 3 and SEQ ID No. 5) in the form of a SalI-BamHI fragment. After purification, the RT-PCR product was digested with SalI and BamHI in order to give a 1995 bp SalI-BamHI fragment.

This fragment was ligated with the vector pVR1012 (Example 6), previously digested with SalI and BamHI, to give the plasmid pPB180 (6863 bp) (FIG. 4).

Example 9

Construction of the Plasmid pPB181 (FeLV Gag/Pol Gene)

An RT-PCR reaction according to the technique of Example 5 was carried out with the feline leukaemia virus (FeLV-A subtype) (Glasgow-1 strain) genomic RNA, prepared according to the technique of Example 3, and with the following oligonucleotides:

```
PB283 (33 mer) (SEQ ID No. 6)
5'TTGTCGACATGTCTGGAGCCTCTAGTGGGACAG3'

PB284 (42 mer) (SEQ ID No. 7)
5'TTGGATCCTTATTTAATTACTGCAGTTCCAAGGAACTCTC3'
``` so as to amplify a 3049 bp fragment containing the sequence encoding the Gag protein and the 5' part of the sequence encoding the Pol protein from the FeLV-A virus (Glasgow-1 strain) (FIG. 5 and SEQ ID No. 8) in the form of a SalI-BamHI fragment. After purification, the RT-PCR product was digested with SalI and BamHI to give a 3039 bp SalI-BamHI fragment.

This fragment was ligated with the vector pVR1012 (Example 6), previously digested with SalI and BamHI, to give the plasmid pPB181 (7908 bp) (FIG. 6).

Example 10

Construction of the Plasmid pAB009 (FPV VP2 Gene)

A PCR reaction was carried out with the feline panleukopaenia virus (193 strain) genomic DNA (J. Martyn et al., J. Gen. Virol. 1990, 71. 2747-2753), prepared according to the technique of Example 2, and with the following oligonucleotides:

```
AB021 (34 mer) (SEQ ID No. 9)
5'TGCTCTAGAGCAATGAGTGATGGAAGCAGTTCAAC3'

AB024 (33 mer) (SEQ ID No. 10)
5'CGCGGATCCATTAATATAATTTTCTAGGTGCTA3'
``` so as to amplify a 1776 bp fragment containing the gene encoding the FPV VP2 capsid protein. After purification, the PCR product was digested with XbaI and BamHI in order to give a 1764 bp XbaI-BamHI fragment.

This fragment was ligated with the vector pVR1012 (Example 6), previously digested with XbaI and BamHI, to give the plasmid pAB009 (6664 bp) (FIG. 7).

Example 11

Construction of the Plasmid pAB053 (FIPV S* Gene)

An RT-PCR reaction according to the technique of Example 5 was carried out with the feline infectious peritonitis (FIP) virus (79-1146 strain) genomic RNA (R. de Groot et al., J. Gen. Virol. 1987. 68. 2639-2646), prepared according to the technique of Example 3, and with the following oligonucleotides:

```
AB103 (38 mer) (SEQ ID No. 11)
5'ATAAGAATGCGGCCGCATGATTGTGCTCGTAACTTGCC3'

AB112 (25 mer) (SEQ ID No. 12)
5'CGTACATGTGGAATTCCACTGGTTG3'
``` so as to amplify the sequence of the 5' part of the gene encoding the virus S glycoprotein in the form of an NotI-EcoRI fragment. After purification, the 492 bp RT-PCR product was digested with NotI and EcoRI in order to liberate a 467 bp NotI-EcoRI fragment (fragment A).

The plasmid pJCA089 (Patent Application PCT/FR95/01128) was digested with EcoRI and SpeI in order to liberate a 3378 bp fragment containing the central part of the gene encoding the FIP virus modified S glycoprotein (fragment B).

An RT-PCR reaction according to the technique of Example 5 was carried out with the FIP virus (79-1146 strain) genomic RNA, prepared according to the technique of Example 3, and with the following oligonucleotides:

```
oligonucleotides:
AB113 (25 mer) (SEQ ID No. 13)
5'AGAGTTGCAACTAGTTCTGATTTTG3'

AB104 (37 mer) (SEQ ID No. 14)
5'ATAAGAATGCGGCCGCTTAGTGGACATGCACTTTTTC3'
``` so as to amplify the sequence of the 3' part of the gene encoding the FIP virus S glycoprotein in the form of an SpeI-NotI fragment. After purification, the 543 bp RT-PCR product was digested with SpeI and NotI in order to liberate a 519 bp SpeI-NotI fragment (fragment C).

The fragments A, B and C were then ligated together into the vector pVR1012 (Example 6), previously digested with NotI, to give the plasmid pAB053 (9282 bp), which contains the modified S gene in the correct orientation relative to the promoter (FIG. 8).

Example 12

Construction of the Plasmid pAB052 (FIPV M Gene)

An RT-PCR reaction according to the technique of Example 5 was carried out with the feline infectious peritonitis (FIP) virus (79-1146 strain) genomic RNA (H. Vennema et al., Virology. 1991, 181. 327-335), prepared according to the technique of Example 3, and with the following oligonucleotides:

```
AB101 (37 mer) (SEQ ID No. 15)
5'ACGCGTCGACCCACCATGAAGTACATTTTGCTAATAC3'

AB102 (36 mer) (SEQ ID No. 16)
5'CGCGGATCCTTACACCATATGTAATAATTTTTCATG3'
``` so as to precisely isolate the gene encoding the FIP virus M glycoprotein in the form of a SalI-BamHI fragment. After purification, the 812 bp RT-PCR product was digested with SalI and BamHI in order to liberate a 799 bp SalI-BamHI fragment. This fragment was then ligated into the vector pVR1012 (Example 6), previously digested with SalI and BamHI, to give the plasmid pAB052 (5668 bp) (FIG. 9).

Example 13

Construction of the Plasmid pAB056 (FIPV N Gene)

An RT-PCR reaction according to the technique of Example 5 was carried out with the feline infectious peritonitis (FIP) virus (79-1146 strain) genomic RNA (H. Vennema et al., Virology. 1991, 181. 327-335), prepared according to the technique of Example 3, and with the following oligonucleotides:

```
AB106 (35 mer) (SEQ ID No. 17)
5'ACGCGTCGACGCCATGGCCACACAGGGACAACGCG3'

AB107 (36 mer) (SEQ ID No. 18)
5'CGCGGATCCTTAGTTCGTAACCTCATCAATCATCTC3'
``` so as to precisely isolate the gene encoding the FIP virus N protein in the form of a SalI-BamHI fragment. After purification, the 1156 bp RT-PCR product was digested with SalI and BamHI in order to liberate a 1143 bp SalI-BamHI fragment. This fragment was then ligated into the vector pVR1012 (Example 6), previously digested with SalI and BamHI, to give the plasmid pAB056 (6011 bp) (FIG. 10).

Example 14

Construction of the Plasmid pAB028 (FHV gB Gene)

A PCR reaction was carried out with the feline herpesvirus (FHV-1) (C27 strain) genomic DNA (S. Spatz et al. Virology. 1993. 197. 125-36) prepared according to the technique of Example 2, and with the following oligonucleotides:

```
AB061 (36 mer) (SEQ ID No. 19)
5'AAAACTGCAGAATCATGTCCACTCGTGGCGATCTTG3'

AB064 (40 mer) (SEQ ID No. 20)
5'ATAAGAATGCGGCCGCTTAGACAAGATTTGTTTCAGTATC3'
``` so as to amplify a 2856 bp fragment containing the gene encoding the FHV-1 virus gB glycoprotein in the form of a PstI-NotI fragment. After purification, the PCR product was digested with PstI and NotI to give a 2823 bp PstI-NotI fragment.

This fragment was ligated with the vector pVR1012 (Example 6), previously digested with PstI and NotI, to give the plasmid pAB028 (7720 bp) (FIG. 11).

Example 15

Construction of the Plasmid pAB029 (FEV gD Gene)

A PCR reaction was carried out with the feline herpesvirus (FHV-1) (C-27 strain) genomic DNA (S. Spatz et al. J. Gen. Virol. 1994. 75. 1235-1244), prepared according to the technique of Example 2 and with the following oligonucleotides:

```
AB065 (36 mer) (SEQ ID No. 21)
5'AAAACTGCAGCCAATGATGACACGTCTACATTTTTG3'

AB066 (33 mer) (SEQ ID No. 22)
5'GGAAGATCTTTAAGGATGGTGAGTTGTATGTAT3'
``` so as to amplify the gene encoding the FHV-1 virus gD glycoprotein in the form of a PstI-BglII fragment. After purification, the 1147 bp PCR product was digested with PstI and BglII in order to isolate a 1129 bp PstI-BglII fragment. This fragment was ligated with the vector pVR1012 (Example 6), previously digested with PstI and BglII, to give the plasmid pAB029 (5982 bp) (FIG. 12).

Example 16

Construction of the Plasmid pAB010 (FCV C Gene)

An RT-PCR reaction according to the technique of Example 5 was carried out with the feline calicivirus (FCV) (F9 strain) genomic RNA (M. Carter et al. Virology. 1992. 190. 443-448), prepared according to the technique of Example 3, and with the following oligonucleotides:

```
AB025 (33 mer) (SEQ ID No.23)
5'ACGCGTCGACGCATGTGCTCAACCTGCGCTAAC3'

AB026 (31 mer) (SEQ ID No.24)
5'CGCGGATCCTCATAACTTAGTCATGGGACTC3'
``` so as to isolate the gene encoding the FCV virus capsid protein in the form of a SalI-BamHI fragment. After purification, the 2042 bp RT-PCR product was digested with SalI and BamHI in order to isolate a 2029 bp SalI-BamHI fragment. This fragment was ligated with the vector PVR1012 (Example 6), previously digested with SalI and BamHI, to give the plasmid pAB010 (6892 bp) (FIG. 13).

Example 17

Construction of the Plasmid pAB030 (FIV Env Gene)

An RT-PCR reaction according to the technique of Example 5 was carried out with the feline immunodeficiency virus (FIV) (Petaluma strain) genomic RNA (R. Olmsted et al. Proc. Natl. Acad. Sci. USA. 1989. 86. 8088-8096), prepared according to the technique of Example 3, and with the following oligonucleotides:

```
AB067 (36 mer) (SEQ ID No.25)
5'AAAACTGCAGAAGGAATGGCAGAAGGATTTGCAGCC3'

AB070 (36 mer) (SEQ ID No.26)
5'CGCGGATCCTCATTCCTCCTCTTTTTCAGACATGCC3'
``` so as to amplify a 2592 bp fragment containing the gene encoding the Env glycoprotein from the FIV virus (Petaluma strain) in the form of a PstI-BamHI fragment. After purification, the RT-PCR product was digested with PstI and BamHI to give a 2575 bp PstI-BamHI fragment.

This fragment was ligated with the vector pVR1012 (Example 6), previously digested with PstI and BamHI, to give the plasmid pAB030 (7436 bp) (FIG. 14).

Example 18

Construction of the Plasmid pAB083 (FIV Gag/Pro Gene)

An RT-PCR reaction according to the technique of Example 5 was carried out with the feline immunodeficiency virus (FIV) (Petaluma strain) genomic RNA (R. Olmsted et al. Proc. Natl. Acad. Sci. USA. 1989. 86. 8088-8096), prepared according to the technique of Example 3, and with the following oligonucleotides:

```
AB154 (32 mer) (SEQ ID No.27)
5'ACGCGTCGACATGGGGAATGGACAGGGGCGAG3'

AB155 (33 mer) (SEQ ID No.28)
5'TGAAGATCTTCACTCATCCCCTTCAGGAAGAGC3'
``` so as to amplify a 4635 bp fragment containing the gene encoding the Gag and Pro proteins from the FIV virus (Petaluma strain) in the form of a SalI-BglII fragment. After purification, the RT-PCR product was digested with SalI and BglII to give a 4622 bp SalI-BglII fragment.

This fragment was ligated with the vector pVR1012 (Example 6), previously digested with SalI and BglII, to give the plasmid pAB083 (7436 bp) (FIG. 15).

Example 19

Construction of the Plasmid pAB041 (Rabies Virus G Gene)

An RT-PCR reaction according to the technique of Example 5 was carried out with the rabies virus (ERA strain) genomic RNA (A. Anilionis et al. Nature. 1981. 294. 275-278), prepared according to the technique of Example 3, and with the following oligonucleotides:

```
AB011 (33 mer) (SEQ ID No.29)
5'AAAACTGCAGAGATGGTTCCTCAGGCTCTCCTG3'

AB012 (34 mer) (SEQ ID No.30)
5'CGCGGATCCTCACAGTCTGGTCTCACCCCCACTC3'
``` so as to amplify a 1589 bp fragment containing the gene encoding the rabies virus G glycoprotein. After purification, the RT-PCR product was digested with PstI and BamHI to give a 1578 bp PstI-BamHI fragment. This fragment was ligated with the vector pVR1012 (Example 6), previously digested with PstI and BamHI, to give the plasmid pAB041 (6437 bp) (FIG. 16).

Example 20

Production and Purification of the Plasmids

For the preparation of the plasmids intended for the vaccination of animals, any technique may be used which makes it possible to obtain a suspension of purified plasmids predominantly in the supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (*Molecular Cloning: A Laboratory Manual*, 2nd edition, Cold Spring Harbor Laboratory, Cold Spring Harbor, N.Y., 1989). Reference may also be made to Patent Applications PCT WO 95/21250 and PCT WO 96/02658 which describe methods for producing, on an industrial scale, plasmids which can be used for vaccination. For the purposes of the manufacture of vaccines (see Example 17), the purified plasmids are resuspended so as to obtain solutions at a high concentration (>2 mg/ml) which are compatible with storage. To do this the plasmids are resuspended either in ultrapure water or in TE buffer (10 mM Tris-HCl; 1 mM EDTA, pH 8.0).

Example 21

Manufacture of the Associated Vaccines

The various plasmids necessary for the manufacture of an associated vaccine are mixed starting with their concentrated solutions (Example 16). The mixtures are prepared such that the final concentration of each plasmid corresponds to the effective dose of each plasmid. The solutions which can be used to adjust the final concentration of the vaccine may be either a 0.9% NaCl solution, or PBS buffer.

Specific formulations such as liposomes, cationic lipids, may also be used for the manufacture of the vaccines.

Example 22

Vaccination of Cats

The cats are vaccinated with doses of 10 μg, 50 μg or 250 μg per plasmid.

The injections are performed with a needle by the intramuscular route. In this case, the vaccinal doses are administered in a volume of 1 ml.

The injections can also be performed with a needle by the intradermal route. In this case, the vaccinal doses are administered in a total volume of 1 ml administered at 10 points of 0.1 ml or at 20 points of 0.05 ml. The intradermal administrations are performed after shaving the skin (thoracic flank in general) or at the level of a relatively glabrous anatomical region, for example the inner surface of the thigh.

A liquid jet injection apparatus (with no needle) can also be used for the intradermal injections.

The invention claimed is:

1. A method for inducing in a feline host an immunological response against feline immunodeficiency virus comprising administering to the feline host at least one naked plasmid wherein the plasmid contains and expresses in vivo in a feline host cell nucleic acid molecule(s) having sequence(s) encoding feline immunodeficiency virus env protein, or gag protein, or pro protein, or gag and pro proteins, or env and gag and pro proteins.

2. The method according to claim 1 which comprises administering to the feline host a naked plasmid wherein the plasmid contains and expresses in vivo in a feline host cell nucleic acid molecule(s) having sequence(s) encoding feline immunodeficiency virus env and gag and pro proteins.

3. The method according to claim 1 which comprises administering to the feline host a first naked plasmid wherein the first plasmid contains and expresses in vivo in a feline host cell a nucleic acid molecule having a sequence encoding feline immunodeficiency virus env protein; and a second naked plasmid wherein the second plasmid contains and expresses in vivo in a feline host cell nucleic acid molecule(s) having sequence(s) encoding feline immunodeficiency virus gag and pro proteins.

4. The method of claim 1 wherein the naked plasmid further comprises a cytomegalovirus early (CMV-IE) promoter operatively linked to at least one of the nucleic acid molecule(s).

5. The method of claim 1 further comprising administering to the feline host a live whole vaccine against a feline pathogen, or an inactivated whole vaccine against a feline pathogen, or recombinant vaccine against a feline pathogen, or a subunit vaccine against a feline pathogen.

6. A method for inducing in a feline host an immunological response against feline immunodeficiency virus comprising administering to the feline host at least one naked plasmid wherein the plasmid contains and expresses in vivo in a feline host cell nucleic acid molecule(s) having sequence(s) encoding feline immunodeficiency virus env protein, or env and gag and pro proteins.

7. The method according to claim 6 which comprises administering to the feline host a naked plasmid wherein the plasmid contains and expresses in vivo in a feline host cell nucleic acid molecule(s) having sequence(s) encoding feline immunodeficiency virus env and gag and pro proteins.

8. The method according to claim 6 which comprises administering to the feline host a first naked plasmid wherein the first plasmid contains and expresses in vivo in a feline host cell a nucleic acid molecule having a sequence encoding feline immunodeficiency virus env protein; and a second naked plasmid wherein the second plasmid contains and expresses in vivo in a feline host cell nucleic acid molecule(s) having sequence(s) encoding feline immunodeficiency virus gag and pro proteins.

9. The method of claim 6 wherein the naked plasmid further comprises a cytomegalovirus early (CMV-IE) promoter operatively linked to at least one of the nucleic acid molecule(s).

10. The method of claim 6 further comprising administering to the feline host a live whole vaccine against a feline pathogen, or an inactivated whole vaccine against a feline pathogen, or recombinant vaccine against a feline pathogen, or a subunit vaccine against a feline pathogen.

11. The method of claim 1 or 6 wherein the immunological response is humoral.

* * * * *

SEQUENCE LISTING

<160> NUMBER OF SEQ ID NOS: 173

<210> SEQ ID NO 1
<211> LENGTH: 381
<212> TYPE: DNA
<213> ORGANISM: Mycobacterium tuberculosis

<400> SEQUENCE: 1

```
ggccgccggt acctatgtgg ccgccgatgc tgcggacgcg tcgacctata ccgggttctg      60
atcgaaccct gctgaccgag aggacttgtg atgtcgcaaa tcatgtacaa ctaccccgcg     120
atgttgggtc acgccgggga tatggccgga tatgccggca cgctgcagag cttgggtgcc     180
gagatcgccg tggagcaggc cgcgttgcag agtgcgtggc agggcgatac cgggatcacg     240
tatcaggcgt ggcaggcaca gtggaaccag gccatggaag atttggtgcg ggcctatcat     300
gcgatgtcca gcacccatga agccaacacc atggcgatga tggcccgcga caccgccgaa     360
gccgccaaat ggggcggcta g                                               381
```

<210> SEQ ID NO 2
<211> LENGTH: 96
<212> TYPE: PRT
<213> ORGANISM: Mycobacterium tuberculosis

<400> SEQUENCE: 2

```
Met Ser Gln Ile Met Tyr Asn Tyr Pro Ala Met Leu Gly His Ala Gly
  1               5                  10                  15
Asp Met Ala Gly Tyr Ala Gly Thr Leu Gln Ser Leu Gly Ala Glu Ile
             20                  25                  30
Ala Val Glu Gln Ala Ala Leu Gln Ser Ala Trp Gln Gly Asp Thr Gly
         35                  40                  45
Ile Thr Tyr Gln Ala Trp Gln Ala Gln Trp Asn Gln Ala Met Glu Asp
     50                  55                  60
Leu Val Arg Ala Tyr His Ala Met Ser Ser Thr His Glu Ala Asn Thr
 65                  70                  75                  80
Met Ala Met Met Ala Arg Asp Thr Ala Glu Ala Ala Lys Trp Gly Gly
                 85                  90                  95
```

<210> SEQ ID NO 3
<211> LENGTH: 467
<212> TYPE: DNA
<213> ORGANISM: Mycobacterium tuberculosis

<400> SEQUENCE: 3

```
gggtagccgg accacggctg ggcaaagatg tgcaggccgc catcaaggcg gtcaaggccg      60
gcgacggcgt cataaacccg gacggcacct tgttggcggg ccccgcggtg ctgacgcccg     120
acgagtacaa ctcccggctg gtggccgccg accggagtc accgcggcg ttgcccgacg      180
gcgccgggct ggtcgttctg gatggcaccg tcactgccga actcgaagcc gagggctggg     240
ccaaagatcg catccgcgaa ctgcaagagc tgcgtaagtc gaccgggctg gacgtttccg     300
accgcatccg ggtggtgatg tcggtgcctg cggaacgcga agactgggcg cgcacccatc     360
gcgacctcat tgccggagaa atcttggcta ccgacttcga attcgccgac ctcgccgatg     420
gtgtggccat cggcgacggc gtgcgggtaa gcatcgaaaa gacctga                   467
```
<210> SEQ ID NO 4
<211> LENGTH: 108
<212> TYPE: PRT
<213> ORGANISM: Mycobacterium tuberculosis

<400> SEQUENCE: 4

```
Met Ala Ala Asp Pro Glu Ser Thr Ala Ala Leu Pro Asp Gly Ala Gly
  1               5                  10                  15

Leu Val Val Leu Asp Gly Thr Val Thr Ala Glu Leu Glu Ala Glu Gly
                 20                  25                  30

Trp Ala Lys Asp Arg Ile Arg Glu Leu Gln Glu Leu Arg Lys Ser Thr
             35                  40                  45

Gly Leu Asp Val Ser Asp Arg Ile Arg Val Val Met Ser Val Pro Ala
 50                  55                  60

Glu Arg Glu Asp Trp Ala Arg Thr His Arg Asp Leu Ile Ala Gly Glu
 65                  70                  75                  80

Ile Leu Ala Thr Asp Phe Glu Phe Ala Asp Leu Ala Asp Gly Val Ala
                 85                  90                  95

Ile Gly Asp Gly Val Arg Val Ser Ile Glu Lys Thr
            100                 105
```

<210> SEQ ID NO 5
<211> LENGTH: 889
<212> TYPE: DNA
<213> ORGANISM: Mycobacterium tuberculosis

<400> SEQUENCE: 5

```
cgggtctgca cggatccggg ccgggcaggg caatcgagcc tgggatccgc tggggtgcgc      60
acatcgcgga cccgtgcgcg gtacggtcga cagcggca cgagaaagta gtaagggcga      120
taataggcgg taaagagtag cgggaagccg gccgaacgac tcggtcagac aacgccacag     180
cggccagtga ggagcagcgg gtgacggaca tgaaccccgga tattgagaag gaccagacct     240
ccgatgaagt cacggtagag acgacctccg tcttccgcgc agacttcctc agcgagctgg     300
acgctcctgc gcaagcgggt acggagagcg cggtctccgg ggtggaaggg ctcccgccgg     360
gctcggcgtt gctggtagtc aaacgaggcc ccaacgccgg gtcccggttc ctactcgacc     420
aagccatcac gtcggctggt cggcatcccg acagcgacat atttctcgac gacgtgaccg     480
tgagccgtcg ccatgctgaa ttccggttgg aaaacaacga attcaatgtc gtcgatgtcg     540
ggagtctcaa cggcacctac gtcaaccgcg agcccgtgga ttcggcggtg ctggcgaacg     600
gcgacgaggt ccagatcggc aagttccggt tggtgttctt gaccggaccc aagcaaggcg     660
aggatgacgg gagtaccggg ggcccgtgag cgcacccgat agccccgcgc tggccgggat     720
gtcgatcggg gcggtcctcg acctgctacg accggatttt cctgatgtca ccatctccaa     780
gattcgattc ttggaggctg agggtctggt gacgccccgg cgggcctcat cggggtatcg     840
gcggttcacc gcatacgact gcgcacggct gcgattcatt ctcactgcc                  889
```

<210> SEQ ID NO 6
<211> LENGTH: 162
<212> TYPE: PRT
<213> ORGANISM: Mycobacterium tuberculosis

<400> SEQUENCE: 6

```
Met Thr Asp Met Asn Pro Asp Ile Glu Lys Asp Gln Thr Ser Asp Glu
  1               5                  10                  15

Val Thr Val Glu Thr Thr Ser Val Phe Arg Ala Asp Phe Leu Ser Glu
                 20                  25                  30

Leu Asp Ala Pro Ala Gln Ala Gly Thr Glu Ser Ala Val Ser Gly Val
             35                  40                  45
```

```
Glu Gly Leu Pro Pro Gly Ser Ala Leu Leu Val Val Lys Arg Gly Pro
     50                  55                  60

Asn Ala Gly Ser Arg Phe Leu Leu Asp Gln Ala Ile Thr Ser Ala Gly
 65                  70                  75                  80

Arg His Pro Asp Ser Asp Ile Phe Leu Asp Val Thr Val Ser Arg
                 85                  90                  95

Arg His Ala Glu Phe Arg Leu Glu Asn Asn Glu Phe Asn Val Val Asp
                100                 105                 110

Val Gly Ser Leu Asn Gly Thr Tyr Val Asn Arg Glu Pro Val Asp Ser
            115                 120                 125

Ala Val Leu Ala Asn Gly Asp Glu Val Gln Ile Gly Lys Phe Arg Leu
        130                 135                 140

Val Phe Leu Thr Gly Pro Lys Gln Gly Glu Asp Asp Gly Ser Thr Gly
145                 150                 155                 160

Gly Pro
```

```
<210> SEQ ID NO 7
<211> LENGTH: 898
<212> TYPE: DNA
<213> ORGANISM: Mycobacterium tuberculosis

<400> SEQUENCE: 7
tcgactccgg cgccaccggg caggatcacg gtgtcgacgg ggtcgccggg gaatcccacg      60
ataaccactc ttcgcgccat gaatgccagt gttggccagg cgctggcctg cgtccacgc     120
cacacaccgc acagattagg acacgccggc ggcgcagccc tgcccgaaag accgtgcacc    180
ggtcttggca gactgtgccc atggcacaga taaccctgcg aggaaacgcg atcaataccg    240
tcggtgagct acctgctgtc ggatccccgg ccccggcctt caccctgacc gggggcgatc    300
tgggggtgat cagcagcgac cagttccggg gtaagtccgt gttgctgaac atctttccat    360
ccgtggacac accggtgtgc gcgacgagtg tgcgaacctt cgacgagcgt gcggcggcaa    420
gtggcgctac cgtgctgtgt gtctcgaagg atctgccgtt cgcccagaag cgcttctgcg    480
gcgccgaggg caccgaaaac gtcatgcccg cgtcggcatt ccgggacagc ttcggcgagg    540
attacggcgt gaccatcgcc gacgggccga tggccgggct gctcgcccgc gcaatcgtgg    600
tgatcggcgc ggacgcaaac gtcgcctaca cggaattggt gccggaaatc gcgcaagaac    660
ccaactacga agcggcgctg gccgcgctgg gcgcctaggc tttcacaagc ccgcgcgtt     720
cggcgagcag cgcacgattt cgagcgctgc tcccgaaaag cgcctcggtg gtcttggccc    780
ggcggtaata caggtgcagg tcgtgctccc acgtgaaggc gatggcaccg tggatctgaa    840
gagcggagcc ggcgcataac acaaaggttt ccgcggtctg cgccttcgcc agcggcgc     898
```

```
<210> SEQ ID NO 8
<211> LENGTH: 165
<212> TYPE: PRT
<213> ORGANISM: Mycobacterium tuberculosis

<400> SEQUENCE: 8

Met Ala Gln Ile Thr Leu Arg Gly Asn Ala Ile Asn Thr Val Gly Glu
 1                5                  10                  15

Leu Pro Ala Val Gly Ser Pro Ala Pro Ala Phe Thr Leu Thr Gly Gly
                 20                  25                  30

Asp Leu Gly Val Ile Ser Ser Asp Gln Phe Arg Gly Lys Ser Val Leu
             35                  40                  45

Leu Asn Ile Phe Pro Ser Val Asp Thr Pro Val Cys Ala Thr Ser Val
         50                  55                  60
```

```
Arg Thr Phe Asp Glu Arg Ala Ala Ser Gly Ala Thr Val Leu Cys
 65                  70                  75                  80

Val Ser Lys Asp Leu Pro Phe Ala Gln Lys Arg Phe Cys Gly Ala Glu
                 85                  90                  95

Gly Thr Glu Asn Val Met Pro Ala Ser Ala Phe Arg Asp Ser Phe Gly
            100                 105                 110

Glu Asp Tyr Gly Val Thr Ile Ala Asp Gly Pro Met Ala Gly Leu Leu
        115                 120                 125

Ala Arg Ala Ile Val Ile Gly Ala Asp Gly Asn Val Ala Tyr Thr
    130                 135                 140

Glu Leu Val Pro Glu Ile Ala Gln Glu Pro Asn Tyr Glu Ala Ala Leu
145                 150                 155                 160

Ala Ala Leu Gly Ala
            165

<210> SEQ ID NO 9
<211> LENGTH: 1054
<212> TYPE: DNA
<213> ORGANISM: Mycobacterium tuberculosis

<400> SEQUENCE: 9
ataatcagct caccgttggg accgacctcg accaggggtc ctttgtgact gccgggcttg     60
acgcggacga ccacagagtc ggtcatcgcc taaggctacc gttctgacct ggggctgcgt    120
gggcgccgac gacgtgaggc acgtcatgtc tcagcggccc accgccacct cggtcgccgg    180
cagtatgtca gcatgtgcag atgactccac gcagccttgt tcgcatcgtt ggtgtcgtgg    240
ttgcgacgac cttggcgctg gtgagcgcac ccgccggcgg tcgtgccgcg catgcggatc    300
cgtgttcgga catcgcggtc gttttcgctc gcggcacgca tcaggcttct ggtcttggcg    360
acgtcggtga ggcgttcgtc gactcgctta cctcgcaagt tggcgggcgg tcgattgggg    420
tctacgcggt gaactaccca gcaagcgacg actaccgcgc gagcgcgtca acggttccg     480 atgatgcgag cgcccacatc cagcgcaccg tcgccagctg cccgaacacc aggattgtgc    540
ttggtggcta ttcgcagggt gcgacggtca tcgatttgtc cacctcggcg atgccgcccg    600
cggtggcaga tcatgtcgcc gctgtcgccc ttttcggcga gccatccagt ggtttctcca    660
gcatgttgtg gggcggcggg tcgttgccga caatcggtcc gctgtatagc tctaagacca    720
taaacttgtg tgctcccgac gatccaatat gcaccggagg cggcaatatt atggcgcatg    780
tttcgtatgt tcagtcgggg atgacaagcc aggcggcgac attcgcggcg aacaggctcg    840
atcacgccgg atgatcaaag actgttgtcc ctataccgct ggggctgtag tcgatgtaca    900
ccggctggaa tctgaagggc aagaacccgg tattcatcag gccggatgaa atgacggtcg    960
ggcggtaatc gtttgtgttg aacgcgtaga gccgatcacc gccggggctg gtgtagacct   1020
caatgtttgt gttcgccggc agggttccgg atcc                               1054

<210> SEQ ID NO 10
<211> LENGTH: 217
<212> TYPE: PRT
<213> ORGANISM: Mycobacterium tuberculosis

<400> SEQUENCE: 10

Met Thr Pro Arg Ser Leu Val Arg Ile Val Gly Val Val Ala Thr
  1               5                  10                  15

Thr Leu Ala Leu Val Ser Ala Pro Ala Gly Gly Arg Ala Ala His Ala
             20                  25                  30
```

```
Asp Pro Cys Ser Asp Ile Ala Val Val Phe Ala Arg Gly Thr His Gln
            35                  40                  45

Ala Ser Gly Leu Gly Asp Val Gly Glu Ala Phe Val Asp Ser Leu Thr
 50                  55                  60

Ser Gln Val Gly Gly Arg Ser Ile Gly Val Tyr Ala Val Asn Tyr Pro
 65                  70                  75                  80

Ala Ser Asp Asp Tyr Arg Ala Ser Ala Ser Asn Gly Ser Asp Asp Ala
                 85                  90                  95

Ser Ala His Ile Gln Arg Thr Val Ala Ser Cys Pro Asn Thr Arg Ile
            100                 105                 110

Val Leu Gly Gly Tyr Ser Gln Gly Ala Thr Val Ile Asp Leu Ser Thr
            115                 120                 125

Ser Ala Met Pro Pro Ala Val Ala Asp His Val Ala Ala Val Ala Leu
130                 135                 140

Phe Gly Glu Pro Ser Ser Gly Phe Ser Ser Met Leu Trp Gly Gly Gly
145                 150                 155                 160

Ser Leu Pro Thr Ile Gly Pro Leu Tyr Ser Ser Lys Thr Ile Asn Leu
                165                 170                 175

Cys Ala Pro Asp Asp Pro Ile Cys Thr Gly Gly Asn Ile Met Ala
            180                 185                 190

His Val Ser Tyr Val Gln Ser Gly Met Thr Ser Gln Ala Ala Thr Phe
            195                 200                 205

Ala Ala Asn Arg Leu Asp His Ala Gly
210                 215

<210> SEQ ID NO 11
<211> LENGTH: 949
<212> TYPE: DNA
<213> ORGANISM: Mycobacterium tuberculosis

<400> SEQUENCE: 11
agccgctcgc gtggggtcaa ccgggttttcc acctgctcac tcattttgcc gcctttctgt      60
gtccgggccg aggcttgcgc tcaataactc ggtcaagttc cttcacagac tgccatcact     120
ggcccgtcgg cgggctcgtt gcgggtgcgc cgcgtgcggg tttgtgttcc gggcaccggg     180
tgggggcccg cccgggcgta atggcagact gtgattccgt gactaacagc cccttgcga     240
ccgctaccgc cacgctgcac actaaccgcg gcgacatcaa gatcgccctg ttcggaaacc     300
atgcgcccaa gaccgtcgcc aatttttgtgg gccttgcgca gggcaccaag gactattcga     360
cccaaaacgc atcaggtggc ccgtccgccc cgttctacga cggcgcggtc tttcaccggg     420
tgatccaggg cttcatgatc cagggtggcg atccaaccgg gacgggtcgc ggcggacccg     480
gctacaagtt cgccgacgag ttccaccccg agctgcaatt cgacaagccc tatctgctcg     540
cgatggccaa cgccggtccg ggcaccaacg gctcacagtt tttcatcacc gtcggcaaga     600
ctccgcacct gaaccggcgc acaccatttt cggtgaagt gatcgacgcg gagtcacagc     660
gggttgtgga ggcgatctcc aagacggcca ccgacggcaa cgatcggccg acggacccgg     720
tggtgatcga gtcgatcacc atctcctgac ccgaagctac gtcggctcgt cgctcgaata     780
caccttgtgg accgccagg cacgtggcg gtacaccgac acgccgttgg ggccgttcaa     840
ccggacgccc tcacgccaag tccgctcacc tttggccgcg accggcgtaa ccggcagcgg     900
taagcgcatc gagcacctcc actgggtcgg tgccgagatc ccagcggga               949
```

<210> SEQ ID NO 12
<211> LENGTH: 182
<212> TYPE: PRT
<213> ORGANISM: Mycobacterium tuberculosis

<400> SEQUENCE: 12

```
Met Ala Asp Cys Asp Ser Val Thr Asn Ser Pro Leu Ala Thr Ala Thr
1               5                  10                  15

Ala Thr Leu His Thr Asn Arg Gly Asp Ile Lys Ile Ala Leu Phe Gly
            20                  25                  30

Asn His Ala Pro Lys Thr Val Ala Asn Phe Val Gly Leu Ala Gln Gly
        35                  40                  45

Thr Lys Asp Tyr Ser Thr Gln Asn Ala Ser Gly Gly Pro Ser Gly Pro
    50                  55                  60

Phe Tyr Asp Gly Ala Val Phe His Arg Val Ile Gln Gly Phe Met Ile
65                  70                  75                  80

Gln Gly Gly Asp Pro Thr Gly Thr Gly Arg Gly Gly Pro Gly Tyr Lys
                85                  90                  95

Phe Ala Asp Glu Phe His Pro Glu Leu Gln Phe Asp Lys Pro Tyr Leu
            100                 105                 110

Leu Ala Met Ala Asn Ala Gly Pro Gly Thr Asn Gly Ser Gln Phe Phe
        115                 120                 125

Ile Thr Val Gly Lys Thr Pro His Leu Asn Arg Arg His Thr Ile Phe
    130                 135                 140

Gly Glu Val Ile Asp Ala Glu Ser Gln Arg Val Val Glu Ala Ile Ser
145                 150                 155                 160

Lys Thr Ala Thr Asp Gly Asn Asp Arg Pro Thr Asp Pro Val Val Ile
                165                 170                 175

Glu Ser Ile Thr Ile Ser
            180
```

<210> SEQ ID NO 13
<211> LENGTH: 1060
<212> TYPE: DNA
<213> ORGANISM: Mycobacterium tuberculosis

<400> SEQUENCE: 13

```
tggaccttca ccggcggtcc cttcgcttcg ggggcgacac ctaacatact ggtcgtcaac    60
ctaccgcgac accgctggga cttttgtgcca ttgccggcca ctcggggccg ctgcggcctg   120
gaaaaattgg tcgggcacgg gcggccgcgg gtcgctacca tcccactgtg aatgatttac   180
tgacccgccg actgctcacc atgggcgcgg ccgccgcaat gctggccgcg gtgcttctgc   240
ttactcccat caccgttccc gccggctacc cggtgccgt tgcaccggcc actgcagcct   300
gccccgacgc cgaagtggtg ttcgcccgcg gccgcttcga accgcccggg attggcacgg   360
tcggcaacgc attcgtcagc gcgctgcgct cgaaggtcaa caagaatgtc ggggtctacg   420
cggtgaaata ccccgccgac aatcagatcg atgtgggcgc caacgacatg agcgcccaca   480
ttcagagcat ggccaacagc tgtccgaata cccgcctggt gcccggcggt tactcgctgg   540
gcgcggccgt caccgacgtg gtactcgcgg tgcccaccca gatgtgggc ttcaccaatc   600
ccctgcctcc cggcagtgat gagcacatcg ccgcggtcgc gctgttcggc aatggcagtc   660
agtgggtcgg cccatcacc aacttcagcc ccgcctacaa cgatcggacc atcgagttgt   720
gtcacggcga cgacccgtc tgccaccctg ccgaccccaa cacctgggag gccaactggc   780
cccagcacct cgccggggcc tatgtctcgt cgggcatggt caaccaggcg ctgacttcg   840
```

```
ttgccggaaa gctgcaatag ccacctagcc cgtgcgcgag tctttgcttc acgctttcgc      900
taaccgacca acgcgcgcac gatggagggg tccgtggtca tatcaagaca agaagggagt      960
aggcgatgca cgcaaaagtc ggcgactacc tcgtggtgaa gggcacaacc acggaacggc     1020
atgatcaaca tgctgagatc atcgaggtgc gctccgcaga                           1060
```

<210> SEQ ID NO 14
<211> LENGTH: 219
<212> TYPE: PRT
<213> ORGANISM: Mycobacterium tuberculosis

<400> SEQUENCE: 14

```
Met Gly Ala Ala Ala Met Leu Ala Ala Val Leu Leu Leu Thr Pro
  1               5                  10                  15

Ile Thr Val Pro Ala Gly Tyr Pro Gly Ala Val Ala Pro Ala Thr Ala
             20                  25                  30

Ala Cys Pro Asp Ala Glu Val Val Phe Ala Arg Gly Arg Phe Glu Pro
         35                  40                  45

Pro Gly Ile Gly Thr Val Gly Asn Ala Phe Val Ser Ala Leu Arg Ser
     50                  55                  60

Lys Val Asn Lys Asn Val Gly Val Tyr Ala Val Lys Tyr Pro Ala Asp
 65                  70                  75                  80

Asn Gln Ile Asp Val Gly Ala Asn Asp Met Ser Ala His Ile Gln Ser
                 85                  90                  95

Met Ala Asn Ser Cys Pro Asn Thr Arg Leu Val Pro Gly Gly Tyr Ser
            100                 105                 110

Leu Gly Ala Ala Val Thr Asp Val Val Leu Ala Val Pro Thr Gln Met
        115                 120                 125

Trp Gly Phe Thr Asn Pro Leu Pro Pro Gly Ser Asp Glu His Ile Ala
    130                 135                 140

Ala Val Ala Leu Phe Gly Asn Gly Ser Gln Trp Val Gly Pro Ile Thr
145                 150                 155                 160

Asn Phe Ser Pro Ala Tyr Asn Asp Arg Thr Ile Glu Leu Cys His Gly
                165                 170                 175

Asp Asp Pro Val Cys His Pro Ala Asp Pro Asn Thr Trp Glu Ala Asn
            180                 185                 190

Trp Pro Gln His Leu Ala Gly Ala Tyr Val Ser Ser Gly Met Val Asn
        195                 200                 205

Gln Ala Ala Asp Phe Val Ala Gly Lys Leu Gln
    210                 215
```

<210> SEQ ID NO 15
<211> LENGTH: 1198
<212> TYPE: DNA
<213> ORGANISM: Mycobacterium tuberculosis

<400> SEQUENCE: 15

```
cagatgctgc gcaacatgtt tctcggcgat ccggcaggca acaccgatcg agtgcttgac       60
ttttccaccg cggtgaccgg cggactgttc ttctcaccca ccatcgactt tctcgaccat      120
ccaccgcccc taccgcaggc ggcgacgcca actctggcag ccgggtcgct atcgatcggc      180
agcttgaaag gaagccccg atgaacaatc tctaccgcga tttggcaccg gtcaccgaag       240
ccgcttgggc ggaaatcgaa ttggaggcgg cgcggacgtt caagcgacac atcgccgggc      300
gccgggtggt cgatgtcagt gatcccgggg ggccgtcac cgcggcggtc agcaccggcc       360
ggctgatcga tgttaaggca ccaaccaacg gcgtgatcgc ccacctgcgg gccagcaaac      420
```

-continued

```
cccttgtccg gctacgggtt ccgtttaccc tgtcgcgcaa cgagatcgac gacgtggaac    480
gtggctctaa ggactccgat tgggaaccgg taaaggaggc ggccaagaag ctggccttcg    540
tcgaggaccg cacaatattc gaaggctaca gcgccgcatc aatcgaaggg atccgcagcg    600
cgagttcgaa cccggcgctg acgttgcccg aggatccccg tgaaatccct gatgtcatct    660
cccaggcatt gtccgaactg cggttggccg gtgtggacgg accgtattcg gtgttgctct    720
ctgctgacgt ctacaccaag gttagcgaga cttccgatca cggctatccc atccgtgagc    780
atctgaaccg gctggtggac ggggacatca tttgggcccc ggccatcgac ggcgcgttcg    840
tgctgaccac tcgaggcggc gacttcgacc tacagctggg caccgacgtt gcaatcgggt    900
acgccagcca cgacacggac accgagcgcc tctacctgca ggagacgctg acgttccttt    960
gctacaccgc cgaggcgtcg gtcgcgctca gccactaagg cacgagcgcg agcaatagct   1020
cctatggcaa gcggccgcgg gttgggtgtg ttcggagctg ggctggtgga cggtgcgcag   1080
ggcctggaag acggtgcggg ctaggcggcg tttgaggcag cgtagtgctg cgcgtttggt   1140
tttcccggcg tcttgcagcc tttggtagta ggcctggccc cggctgtcgg tcatccgg     1198
```

<210> SEQ ID NO 16
<211> LENGTH: 265
<212> TYPE: PRT
<213> ORGANISM: Mycobacterium tuberculosis

<400> SEQUENCE: 16

```
Met Asn Asn Leu Tyr Arg Asp Leu Ala Pro Val Thr Glu Ala Ala Trp
  1               5                  10                  15

Ala Glu Ile Glu Leu Glu Ala Ala Arg Thr Phe Lys Arg His Ile Ala
             20                  25                  30

Gly Arg Arg Val Val Asp Val Ser Asp Pro Gly Gly Pro Val Thr Ala
         35                  40                  45

Ala Val Ser Thr Gly Arg Leu Ile Asp Val Lys Ala Pro Thr Asn Gly
     50                  55                  60

Val Ile Ala His Leu Arg Ala Ser Lys Pro Leu Val Arg Leu Arg Val
 65                  70                  75                  80

Pro Phe Thr Leu Ser Arg Asn Glu Ile Asp Asp Val Glu Arg Gly Ser
                 85                  90                  95

Lys Asp Ser Asp Trp Glu Pro Val Lys Glu Ala Lys Lys Leu Ala
            100                 105                 110

Phe Val Glu Asp Arg Thr Ile Phe Glu Gly Tyr Ser Ala Ala Ser Ile
        115                 120                 125

Glu Gly Ile Arg Ser Ala Ser Ser Asn Pro Ala Leu Thr Leu Pro Glu
    130                 135                 140

Asp Pro Arg Glu Ile Pro Asp Val Ile Ser Gln Ala Leu Ser Glu Leu
145                 150                 155                 160

Arg Leu Ala Gly Val Asp Gly Pro Tyr Ser Val Leu Leu Ser Ala Asp
                165                 170                 175

Val Tyr Thr Lys Val Ser Glu Thr Ser Asp His Gly Tyr Pro Ile Arg
            180                 185                 190

Glu His Leu Asn Arg Leu Val Asp Gly Asp Ile Ile Trp Ala Pro Ala
        195                 200                 205

Ile Asp Gly Ala Phe Val Leu Thr Thr Arg Gly Gly Asp Phe Asp Leu
    210                 215                 220

Gln Leu Gly Thr Asp Val Ala Ile Gly Tyr Ala Ser His Asp Thr Asp
225                 230                 235                 240
```

```
Thr Glu Arg Leu Tyr Leu Gln Glu Thr Leu Thr Phe Leu Cys Tyr Thr
            245                 250                 255

Ala Glu Ala Ser Val Ala Leu Ser His
            260                 265

<210> SEQ ID NO 17
<211> LENGTH: 15
<212> TYPE: PRT
<213> ORGANISM: Mycobacterium tuberculosis
<220> FEATURE:
<221> NAME/KEY: VARIANT
<222> LOCATION: (1)
<223> OTHER INFORMATION: Ala is Ala or Ser
<221> NAME/KEY: UNSURE
<222> LOCATION: (13)
<223> OTHER INFORMATION: Xaa is unknown

<400> SEQUENCE: 17

Ala Glu Leu Asp Ala Pro Ala Gln Ala Gly Thr Glu Xaa Ala Val
  1               5                  10                  15

<210> SEQ ID NO 18
<211> LENGTH: 15
<212> TYPE: PRT
<213> ORGANISM: Mycobacterium tuberculosis

<400> SEQUENCE: 18

Ala Gln Ile Thr Leu Arg Gly Asn Ala Ile Asn Thr Val Gly Glu
  1               5                  10                  15

<210> SEQ ID NO 19
<211> LENGTH: 15
<212> TYPE: PRT
<213> ORGANISM: Mycobacterium tuberculosis
<220> FEATURE:
<221> NAME/KEY: UNSURE
<222> LOCATION: (3)
<223> OTHER INFORMATION: Xaa is unknown

<400> SEQUENCE: 19

Asp Pro Xaa Ser Asp Ile Ala Val Val Phe Ala Arg Gly Thr His
  1               5                  10                  15

<210> SEQ ID NO 20
<211> LENGTH: 15
<212> TYPE: PRT
<213> ORGANISM: Mycobacterium tuberculosis

<400> SEQUENCE: 20

Thr Asn Ser Pro Leu Ala Thr Ala Thr Ala Thr Leu His Thr Asn
  1               5                  10                  15

<210> SEQ ID NO 21
<211> LENGTH: 15
<212> TYPE: PRT
<213> ORGANISM: Mycobacterium tuberculosis
<220> FEATURE:
<221> NAME/KEY: UNSURE
<222> LOCATION: (2)
<223> OTHER INFORMATION: Xaa is unknown

<400> SEQUENCE: 21

Ala Xaa Pro Asp Ala Glu Val Val Phe Ala Arg Gly Arg Phe Glu
  1               5                  10                  15
```

```
<210> SEQ ID NO 22
<211> LENGTH: 15
<212> TYPE: PRT
<213> ORGANISM: Mycobacterium tuberculosis
<220> FEATURE:
<221> NAME/KEY: UNSURE
<222> LOCATION: (1)
<223> OTHER INFORMATION: Xaa is unknown
<221> NAME/KEY: VARIANT
<222> LOCATION: (2)
<223> OTHER INFORMATION: Ile is Ile or Val
<221> NAME/KEY: VARIANT
<222> LOCATION: (10)
<223> OTHER INFORMATION: Val is Val or Thr
<221> NAME/KEY: VARIANT
<222> LOCATION: (11)
<223> OTHER INFORMATION: Val is Val or Phe
<221> NAME/KEY: VARIANT
<222> LOCATION: (14)
<223> OTHER INFORMATION: Asp is Asp or Gln

<400> SEQUENCE: 22

Xaa Ile Gln Lys Ser Leu Glu Leu Ile Val Val Thr Ala Asp Glu
 1               5                  10                  15

<210> SEQ ID NO 23
<211> LENGTH: 19
<212> TYPE: PRT
<213> ORGANISM: Mycobacterium tuberculosis

<400> SEQUENCE: 23

Met Asn Asn Leu Tyr Arg Asp Leu Ala Pro Val Thr Glu Ala Ala Trp
 1               5                  10                  15
Ala Glu Ile

<210> SEQ ID NO 24
<211> LENGTH: 34
<212> TYPE: DNA
<213> ORGANISM: Mycobacterium tuberculosis

<400> SEQUENCE: 24
cccggctcga gaacctstac cgcgacctsg cscc                          34

<210> SEQ ID NO 25
<211> LENGTH: 37
<212> TYPE: DNA
<213> ORGANISM: Mycobacterium tuberculosis

<400> SEQUENCE: 25
gggccggatc cgasgcsgcg tccttsacsg gytgcca                       37

<210> SEQ ID NO 26
<211> LENGTH: 28
<212> TYPE: DNA
<213> ORGANISM: Mycobacterium tuberculosis

<400> SEQUENCE: 26
ggaagcccca tatgaacaat ctctaccg                                 28

<210> SEQ ID NO 27
<211> LENGTH: 32
<212> TYPE: DNA
<213> ORGANISM: Mycobacterium tuberculosis

<400> SEQUENCE: 27
cgcgctcagc ccttagtgac tgagcgcgac cg                            32
```

```
<210> SEQ ID NO 28
<211> LENGTH: 24
<212> TYPE: DNA
<213> ORGANISM: Mycobacterium tuberculosis

<400> SEQUENCE: 28
ctcgaattcg ccgggtgcac acag                                          24

<210> SEQ ID NO 29
<211> LENGTH: 25
<212> TYPE: DNA
<213> ORGANISM: Mycobacterium tuberculosis

<400> SEQUENCE: 29
ctcgaattcg cccccatacg agaac                                         25

<210> SEQ ID NO 30
<211> LENGTH: 15
<212> TYPE: DNA
<213> ORGANISM: Mycobacterium tuberculosis

<400> SEQUENCE: 30
gtgtatctgc tggac                                                    15

<210> SEQ ID NO 31
<211> LENGTH: 15
<212> TYPE: DNA
<213> ORGANISM: Mycobacterium tuberculosis

<400> SEQUENCE: 31
ccgactggct ggccg                                                    15

<210> SEQ ID NO 32
<211> LENGTH: 24
<212> TYPE: DNA
<213> ORGANISM: Mycobacterium tuberculosis

<400> SEQUENCE: 32
gaggaattcg cttagcggat cgca                                          24

<210> SEQ ID NO 33
<211> LENGTH: 15
<212> TYPE: DNA
<213> ORGANISM: Mycobacterium tuberculosis

<400> SEQUENCE: 33
cccacattcc gttgg                                                    15

<210> SEQ ID NO 34
<211> LENGTH: 15
<212> TYPE: DNA
<213> ORGANISM: Mycobacterium tuberculosis

<400> SEQUENCE: 34
gtccagcaga tacac                                                    15

<210> SEQ ID NO 35
<211> LENGTH: 27
<212> TYPE: DNA
<213> ORGANISM: Mycobacterium tuberculosis

<400> SEQUENCE: 35
gtacgagaat tcatgtcgca aatcatg                                       27
```

-continued

<210> SEQ ID NO 36
<211> LENGTH: 27
<212> TYPE: DNA
<213> ORGANISM: Mycobacterium tuberculosis

<400> SEQUENCE: 36
gtacgagaat tcgagcttgg ggtgccg 27

<210> SEQ ID NO 37
<211> LENGTH: 28
<212> TYPE: DNA
<213> ORGANISM: Mycobacterium tuberculosis

<400> SEQUENCE: 37
cgattccaag cttgtggccg ccgacccg 28

<210> SEQ ID NO 38
<211> LENGTH: 30
<212> TYPE: DNA
<213> ORGANISM: Mycobacterium tuberculosis

<400> SEQUENCE: 38
cgttagggat cctcatcgcc atggtgttgg 30

<210> SEQ ID NO 39
<211> LENGTH: 26
<212> TYPE: DNA
<213> ORGANISM: Mycobacterium tuberculosis

<400> SEQUENCE: 39
cgttagggat ccggttccac tgtgcc 26

<210> SEQ ID NO 40
<211> LENGTH: 28
<212> TYPE: DNA
<213> ORGANISM: Mycobacterium tuberculosis

<400> SEQUENCE: 40
cgttagggat cctcaggtct tttcgatg 28

<210> SEQ ID NO 41
<211> LENGTH: 952
<212> TYPE: DNA
<213> ORGANISM: Mycobacterium tuberculosis

<400> SEQUENCE: 41
gaattcgccg ggtgcacaca gccttacacg acggaggtgg acacatgaag ggtcggtcgg 60
cgctgctgcg ggcgctctgg attgccgcac tgtcattcgg gttgggcggt gtcgcggtag 120
ccgcggaacc caccgccaag gccgccccat acgagaacct gatggtgccg tcgccctcga 180
tgggccggga catcccggtg gccttcctag ccggtgggcc gcacgcggtg tatctgctgg 240
acgccttcaa cgccggcccg gatgtcagta actgggtcac cgcgggtaac gcgatgaaca 300
cgttggcggg caaggggatt tcggtggtgg caccggccgg tggtgcgtac agcatgtaca 360
ccaactggga gcaggatggc agcaagcagt gggacacctt cttgtccgct gagctgcccg 420
actggctggc cgctaaccgg ggcttggccc ccggtggcca tgcggccgtt ggcgccgctc 480
agggcggtta cggggcgatg gcgctggcgg ccttccaccc cgaccgcttc ggcttcgctg 540
gctcgatgtc gggctttttg tacccgtcga acaccaccac caacggtgcg atcgcggcgg 600
gcatgcagca attcggcggt gtggacacca acggaatgtg gggagcacca cagctgggtc 660

```
ggtggaagtg gcacgacccg tgggtgcatg ccagcctgct ggcgcaaaac aacacccggg    720
tgtgggtgtg gagcccgacc aacccgggag ccagcgatcc cgccgccatg atcggccaaa    780
ccgccgaggc gatgggtaac agccgcatgt tctacaacca gtatcgcagc gtcggcgggc    840
acaacggaca cttcgacttc ccagccagcg tgacaacgg ctggggctcg tgggcgcccc     900
agctgggcgc tatgtcgggc gatatcgtcg gtgcgatccc taagcgaatt tc            952
```

<210> SEQ ID NO 42
<211> LENGTH: 299
<212> TYPE: PRT
<213> ORGANISM: Mycobacterium tuberculosis

<400> SEQUENCE: 42

```
Met Lys Gly Arg Ser Ala Leu Leu Arg Ala Leu Trp Ile Ala Ala Leu
  1               5                  10                  15

Ser Phe Gly Leu Gly Gly Val Ala Val Ala Ala Glu Pro Thr Ala Lys
                 20                  25                  30

Ala Ala Pro Tyr Glu Asn Leu Met Val Pro Ser Pro Ser Met Gly Arg
             35                  40                  45

Asp Ile Pro Val Ala Phe Leu Ala Gly Gly Pro His Ala Val Tyr Leu
         50                  55                  60

Leu Asp Ala Phe Asn Ala Gly Pro Asp Val Ser Asn Trp Val Thr Ala
 65                  70                  75                  80

Gly Asn Ala Met Asn Thr Leu Ala Gly Lys Gly Ile Ser Val Val Ala
                 85                  90                  95

Pro Ala Gly Gly Ala Tyr Ser Met Tyr Thr Asn Trp Glu Gln Asp Gly
            100                 105                 110

Ser Lys Gln Trp Asp Thr Phe Leu Ser Ala Glu Leu Pro Asp Trp Leu
        115                 120                 125

Ala Ala Asn Arg Gly Leu Ala Pro Gly Gly His Ala Ala Val Gly Ala
    130                 135                 140

Ala Gln Gly Gly Tyr Gly Ala Met Ala Leu Ala Ala Phe His Pro Asp
145                 150                 155                 160

Arg Phe Gly Phe Ala Gly Ser Met Ser Gly Phe Leu Tyr Pro Ser Asn
                165                 170                 175

Thr Thr Thr Asn Gly Ala Ile Ala Ala Gly Met Gln Gln Phe Gly Gly
            180                 185                 190

Val Asp Thr Asn Gly Met Trp Gly Ala Pro Gln Leu Gly Arg Trp Lys
        195                 200                 205

Trp His Asp Pro Trp Val His Ala Ser Leu Leu Ala Gln Asn Asn Thr
    210                 215                 220

Arg Val Trp Val Trp Ser Pro Thr Asn Pro Gly Ala Ser Asp Pro Ala
225                 230                 235                 240

Ala Met Ile Gly Gln Thr Ala Glu Ala Met Gly Asn Ser Arg Met Phe
                245                 250                 255

Tyr Asn Gln Tyr Arg Ser Val Gly Gly His Asn Gly His Phe Asp Phe
            260                 265                 270

Pro Ala Ser Gly Asp Asn Gly Trp Gly Ser Trp Ala Pro Gln Leu Gly
        275                 280                 285

Ala Met Ser Gly Asp Ile Val Gly Ala Ile Arg
    290                 295
```

```
<210> SEQ ID NO 43
<211> LENGTH: 27
<212> TYPE: DNA
<213> ORGANISM: Mycobacterium tuberculosis

<400> SEQUENCE: 43
gcaacacccg ggatgtcgca aatcatg                                         27

<210> SEQ ID NO 44
<211> LENGTH: 27
<212> TYPE: DNA
<213> ORGANISM: Mycobacterium tuberculosis

<400> SEQUENCE: 44
gtaacacccg gggtggccgc cgacccg                                         27

<210> SEQ ID NO 45
<211> LENGTH: 37
<212> TYPE: DNA
<213> ORGANISM: Mycobacterium tuberculosis

<400> SEQUENCE: 45
ctactaagct tggatcccta gccgccccat ttggcgg                              37

<210> SEQ ID NO 46
<211> LENGTH: 38
<212> TYPE: DNA
<213> ORGANISM: Mycobacterium tuberculosis

<400> SEQUENCE: 46
ctactaagct tccatggtca ggtcttttcg atgcttac                             38

<210> SEQ ID NO 47
<211> LENGTH: 450
<212> TYPE: DNA
<213> ORGANISM: Mycobacterium tuberculosis

<400> SEQUENCE: 47
gtgccgcgct ccccagggtt cttatggttc gatatacctg agtttgatgg aagtccgatg     60
accagcagtc agcatacggc atggccgaaa agagtggggt gatgatggcc gaggatgttc    120
gcgccgagat cgtggccagc gttctcgaag tcgttgtcaa cgaaggcgat cagatcgaca    180
agggcgacgt cgtggtgctg ctggagtcga tgaagatgga gatccccgtc ctggccgaag    240
ctgccggaac ggtcagcaag gtggcggtat cggtgggcga tgtcattcag gccggcgacc    300
ttatcgcggt gatcagctag tcgttgatag tcactcatgt ccacactcgg tgatctgctc    360
gccgaacaca cggtgctgcc gggcagcgcg gtggaccacc tgcatgcggt ggtcggggag    420
tggcagctcc ttgccgactt gtcgtttgcc                                    450

<210> SEQ ID NO 48
<211> LENGTH: 71
<212> TYPE: PRT
<213> ORGANISM: Mycobacterium tuberculosis

<400> SEQUENCE: 48

Met Ala Glu Asp Val Arg Ala Glu Ile Val Ala Ser Val Leu Glu Val
 1               5                  10                  15

Val Val Asn Glu Gly Asp Gln Ile Asp Lys Gly Asp Val Val Val Leu
            20                  25                  30

Leu Glu Ser Met Lys Met Glu Ile Pro Val Leu Ala Glu Ala Ala Gly
        35                  40                  45
```

```
Thr Val Ser Lys Val Ala Val Ser Val Gly Asp Val Ile Gln Ala Gly
         50                  55                  60

Asp Leu Ile Ala Val Ile Ser
 65                  70
```

<210> SEQ ID NO 49
<211> LENGTH: 750
<212> TYPE: DNA
<213> ORGANISM: Mycobacterium tuberculosis

<400> SEQUENCE: 49

```
gggtacccat cgatgggttg cggttcggca ccgaggtgct aacgcacttg ctgacacact    60
gctagtcgaa aacgaggcta gtcgcaacgt cgatcacacg agaggactga ccatgacaac   120
ttcacccgac ccgtatgccg cgctgcccaa gctgccgtcc ttcagcctga cgtcaacctc   180
gatcaccgat gggcagccgc tggctacacc ccaggtcagc gggatcatgg gtgcgggcgg   240
ggcggatgcc agtccgcagc tgaggtggtc gggatttccc agcgagaccc gcagcttcgc   300
ggtaaccgtc tacgaccctg atgccccac cctgtccggg ttctggcact gggcggtggc   360
caacctgcct gccaacgtca ccgagttgcc cgagggtgtc ggcgatggcc gcgaactgcc   420
gggcggggca ctgacattgg tcaacgacgc cggtatgcgc cggtatgtgg gtgcggcgcc   480
gcctcccggt catggggtgc atcgctacta cgtcgcggta cacgcggtga aggtcgaaaa   540
gctcgacctc cccgaggacg cgagtcctgc atatctggga ttcaacctgt tccagcacgc   600
gattgcacga gcggtcatct cggcacctta cgagcagcgt tagcgcttta gctgggttgc   660
cgacgtcttg ccgagccgac cgcttcgtgc agcgagccga accgccgtc atgcagcctg   720
cgggcaatgc cttcatggat gtccttggcc                                    750
```

<210> SEQ ID NO 50
<211> LENGTH: 176
<212> TYPE: PRT
<213> ORGANISM: Mycobacterium tuberculosis

<400> SEQUENCE: 50

```
Met Thr Thr Ser Pro Asp Pro Tyr Ala Ala Leu Pro Lys Leu Pro Ser
  1               5                  10                  15

Phe Ser Leu Thr Ser Thr Ser Ile Thr Asp Gly Gln Pro Leu Ala Thr
                 20                  25                  30

Pro Gln Val Ser Gly Ile Met Gly Ala Gly Gly Ala Asp Ala Ser Pro
             35                  40                  45

Gln Leu Arg Trp Ser Gly Phe Pro Ser Glu Thr Arg Ser Phe Ala Val
     50                  55                  60

Thr Val Tyr Asp Pro Asp Ala Pro Thr Leu Ser Gly Phe Trp His Trp
 65                  70                  75                  80

Ala Val Ala Asn Leu Pro Ala Asn Val Thr Glu Leu Pro Glu Gly Val
                 85                  90                  95

Gly Asp Gly Arg Glu Leu Pro Gly Gly Ala Leu Thr Leu Val Asn Asp
            100                 105                 110

Ala Gly Met Arg Arg Tyr Val Gly Ala Ala Pro Pro Gly His Gly
            115                 120                 125

Val His Arg Tyr Tyr Val Ala Val His Ala Val Lys Val Glu Lys Leu
        130                 135                 140
```

Asp Leu Pro Glu Asp Ala Ser Pro Ala Tyr Leu Gly Phe Asn Leu Phe
145                 150                 155                 160

Gln His Ala Ile Ala Arg Ala Val Ile Phe Gly Thr Tyr Glu Gln Arg
                165                 170                 175

<210> SEQ ID NO 51
<211> LENGTH: 800
<212> TYPE: DNA
<213> ORGANISM: Mycobacterium tuberculosis

<400> SEQUENCE: 51

| | | | | | |
|---|---|---|---|---|---|
| tcatgaggtt | catcggggtg | atcccacgcc | cgcagccgca | ttcgggccgc | tggcgagccg | 60 |
| gtgccgcacg | ccgcctcacc | agcctggtgg | ccgccgcctt | tgcggcggcc | acactgttgc | 120 |
| ttaccccgc | gctggcacca | ccggcatcgg | cgggctgccc | ggatgccgag | gtggtgttcg | 180 |
| cccgcggaac | cggcgaacca | cctggcctcg | gtcgggtagg | ccaagctttc | gtcagttcat | 240 |
| tgcgccagca | gaccaacaag | agcatcggga | catacggagt | caactacccg | gccaacggtg | 300 |
| atttcttggc | cgccgctgac | ggcgcgaacg | acgccagcga | ccacattcag | cagatggcca | 360 |
| gcgcgtgccg | ggccacgagg | ttggtgctcg | gcggctactc | ccagggtgcg | gccgtgatcg | 420 |
| acatcgtcac | cgccgcacca | ctgcccggcc | tcgggttcac | gcagccgttg | ccgcccgcag | 480 |
| cggacgatca | catcgccgcg | atcgcccgt | tcgggaatcc | ctcgggccgc | gctggcgggc | 540 |
| tgatgagcgc | cctgaccect | caattcgggt | ccaagaccat | caacctctgc | aacaacggcg | 600 |
| acccgatttg | ttcggacggc | aaccggtggc | gagcgcacct | aggctacgtg | cccgggatga | 660 |
| ccaaccaggc | ggcgcgtttc | gtcgcgagca | ggatctaacg | cgagccgccc | catagattcc | 720 |
| ggctaagcaa | cggctgcgcc | gccgcccggc | cacgagtgac | cgccgccgac | tggcacaccg | 780 |
| cttaccacgg | ccttatgctg | | | | | 800 |

<210> SEQ ID NO 52
<211> LENGTH: 226
<212> TYPE: PRT
<213> ORGANISM: Mycobacterium tuberculosis

<400> SEQUENCE: 52

Met Ile Pro Arg Pro Gln Pro His Ser Gly Arg Trp Arg Ala Gly Ala
1               5                   10                  15

Ala Arg Arg Leu Thr Ser Leu Val Ala Ala Phe Ala Ala Ala Thr
                20                  25                  30

Leu Leu Leu Thr Pro Ala Leu Ala Pro Pro Ala Ser Ala Gly Cys Pro
            35                  40                  45

Asp Ala Glu Val Val Phe Ala Arg Gly Thr Gly Glu Pro Pro Gly Leu
        50                  55                  60

Gly Arg Val Gly Gln Ala Phe Val Ser Ser Leu Arg Gln Gln Thr Asn
65                  70                  75                  80

Lys Ser Ile Gly Thr Tyr Gly Val Asn Tyr Pro Ala Asn Gly Asp Phe
                85                  90                  95

Leu Ala Ala Ala Asp Gly Ala Asn Asp Ala Ser Asp His Ile Gln Gln
            100                 105                 110

Met Ala Ser Ala Cys Arg Ala Thr Arg Leu Val Leu Gly Gly Tyr Ser
        115                 120                 125

Gln Gly Ala Ala Val Ile Asp Ile Val Thr Ala Ala Pro Leu Pro Gly
    130                 135                 140

Leu Gly Phe Thr Gln Pro Leu Pro Pro Ala Ala Asp Asp His Ile Ala
145                 150                 155                 160

-continued

```
Ala Ile Ala Leu Phe Gly Asn Pro Ser Gly Arg Ala Gly Gly Leu Met
                165                 170                 175

Ser Ala Leu Thr Pro Gln Phe Gly Ser Lys Thr Ile Asn Leu Cys Asn
            180                 185                 190

Asn Gly Asp Pro Ile Cys Ser Asp Gly Asn Arg Trp Arg Ala His Leu
        195                 200                 205

Gly Tyr Val Pro Gly Met Thr Asn Gln Ala Ala Arg Phe Val Ala Ser
    210                 215                 220

Arg Ile
225

<210> SEQ ID NO 53
<211> LENGTH: 700
<212> TYPE: DNA
<213> ORGANISM: Mycobacterium tuberculosis

<400> SEQUENCE: 53
ctaggaaagc ctttcctgag taagtattgc cttcgttgca taccgccctt tacctgcgtt     60
aatctgcatt ttatgacaga atacgaaggg cctaagacaa aattccacgc gttaatgcag    120
gaacagattc ataacgaatt cacagcggca caacaatatg tcgcgatcgc ggtttatttc    180
gacagcgaag acctgccgca gttggcgaag catttttaca gccaagcggt cgaggaacga    240
aaccatgcaa tgatgctcgt gcaacacctg ctcgaccgcg accttcgtgt cgaaattccc    300
ggcgtagaca cggtgcgaaa ccagttcgac agaccccgcg aggcactggc gctggcgctc    360
gatcaggaac gcacagtcac cgaccaggtc ggtcggctga cagcggtggc ccgcgacgag    420
ggcgatttcc tcggcgagca gttcatgcag tggttcttgc aggaacagat cgaagaggtg    480
gccttgatgg caaccctggt gcgggttgcc gatcgggccg ggccaacct gttcgagcta    540 gagaacttcg tcgcacgtga agtggatgtg gcgccggccg catcaggcgc cccgcacgct    600
gccgggggcc gcctctagat ccctggcggg gatcagcgag tggtcccgtt cgcccgcccg    660
tcttccagcc aggccttggt gcggccgggg tggtgagtac                          700

<210> SEQ ID NO 54
<211> LENGTH: 181
<212> TYPE: PRT
<213> ORGANISM: Mycobacterium tuberculosis

<400> SEQUENCE: 54

Met Thr Glu Tyr Glu Gly Pro Lys Thr Lys Phe His Ala Leu Met Gln
  1               5                  10                  15

Glu Gln Ile His Asn Glu Phe Thr Ala Ala Gln Gln Tyr Val Ala Ile
             20                  25                  30

Ala Val Tyr Phe Asp Ser Glu Asp Leu Pro Gln Leu Ala Lys His Phe
         35                  40                  45

Tyr Ser Gln Ala Val Glu Glu Arg Asn His Ala Met Met Leu Val Gln
     50                  55                  60

His Leu Leu Asp Arg Asp Leu Arg Val Glu Ile Pro Gly Val Asp Thr
 65                  70                  75                  80

Val Arg Asn Gln Phe Asp Arg Pro Arg Glu Ala Leu Ala Leu Ala Leu
                 85                  90                  95

Asp Gln Glu Arg Thr Val Thr Asp Gln Val Gly Arg Leu Thr Ala Val
            100                 105                 110

Ala Arg Asp Glu Gly Asp Phe Leu Gly Glu Gln Phe Met Gln Trp Phe
        115                 120                 125
```

Leu Gln Glu Gln Ile Glu Val Ala Leu Met Ala Thr Leu Val Arg
    130                 135                 140

Val Ala Asp Arg Ala Gly Ala Asn Leu Phe Glu Leu Glu Asn Phe Val
145                 150                 155                 160

Ala Arg Glu Val Asp Val Ala Pro Ala Ala Ser Gly Ala Pro His Ala
                165                 170                 175

Ala Gly Gly Arg Leu
            180

<210> SEQ ID NO 55
<211> LENGTH: 950
<212> TYPE: DNA
<213> ORGANISM: Mycobacterium tuberculosis

<400> SEQUENCE: 55
tgggctcggc actggctctc ccacggtggc gcgctgattt ctccccacgg taggcgttgc      60
gacgcatgtt cttcaccgtc tatccacagc taccgacatt tgctccggct ggatcgcggg     120
taaaattccg tcgtgaacaa tcgacccatc cgcctgctga catccggcag gctggtttg     180 ggtgcgggcg cattgatcac cgccgtcgtc ctgctcatcg ccttgggcgc tgtttggacc     240
ccggttgcct cgccgatgg atgcccggac gccgaagtca cgttcgcccg cggcaccggc     300
gagccgcccg gaatcgggcg cgttggccag gcgttcgtcg actcgctgcg ccagcagact     360
ggcatggaga tcggagtata cccggtgaat tacgccgcca ccgcctaca gctgcacggg     420 ggagacggcg ccaacgacgc catatcgcac attaagtcca tggcctcgtc atgcccgaac     480
accaagctgg tcttgggcgg ctattcgcag gccgcaaccg tgatcgatat cgtggccggg     540
gttccgttgg gcagcatcag ctttggcagt ccgctacctg cggcatacgc agacaacgtc     600
gcagcggtcg cggtcttcgg caatccgtcc aaccgcgccg gcggatcgct gtcgagcctg     660
agcccgctat tcggttccaa ggcgattgac ctgtgcaatc ccaccgatcc gatctgccat     720
gtgggccccg gcaacgaatt cagcggacac atcgacggct acatacccac ctacaccacc     780
caggcggcta gtttcgtcgt gcagaggctc cgcgccgggt cggtgccaca tctgcctgga     840
tccgtcccgc agctgcccgg gtctgtcctt cagatgcccg gcactgccgc accggctccc     900
gaatcgctgc acggtcgctg acgctttgtc agtaagccca taaaatcgcg                 950

<210> SEQ ID NO 56
<211> LENGTH: 262
<212> TYPE: PRT
<213> ORGANISM: Mycobacterium tuberculosis

<400> SEQUENCE: 56

Met Asn Asn Arg Pro Ile Arg Leu Leu Thr Ser Gly Arg Ala Gly Leu
1               5                   10                  15

Gly Ala Gly Ala Leu Ile Thr Ala Val Val Leu Ile Ala Leu Gly
            20                  25                  30

Ala Val Trp Thr Pro Val Ala Phe Ala Asp Gly Cys Pro Asp Ala Glu
        35                  40                  45

Val Thr Phe Ala Arg Gly Thr Gly Glu Pro Gly Ile Gly Arg Val
    50                  55                  60

Gly Gln Ala Phe Val Asp Ser Leu Arg Gln Gln Thr Gly Met Glu Ile
65                  70                  75                  80

Gly Val Tyr Pro Val Asn Tyr Ala Ala Ser Arg Leu Gln Leu His Gly
                85                  90                  95

-continued

```
Gly Asp Gly Ala Asn Asp Ala Ile Ser His Ile Lys Ser Met Ala Ser
            100                 105                 110

Ser Cys Pro Asn Thr Lys Leu Val Leu Gly Gly Tyr Ser Gln Gly Ala
        115                 120                 125

Thr Val Ile Asp Ile Val Ala Gly Val Pro Leu Gly Ser Ile Ser Phe
    130                 135                 140

Gly Ser Pro Leu Pro Ala Ala Tyr Ala Asp Asn Val Ala Ala Val Ala
145                 150                 155                 160

Val Phe Gly Asn Pro Ser Asn Arg Ala Gly Gly Ser Leu Ser Ser Leu
                165                 170                 175

Ser Pro Leu Phe Gly Ser Lys Ala Ile Asp Leu Cys Asn Pro Thr Asp
            180                 185                 190

Pro Ile Cys His Val Gly Pro Gly Asn Glu Phe Ser Gly His Ile Asp
        195                 200                 205

Gly Tyr Ile Pro Thr Tyr Thr Thr Gln Ala Ala Ser Phe Val Val Gln
    210                 215                 220

Arg Leu Arg Ala Gly Ser Val Pro His Leu Pro Gly Ser Val Pro Gln
225                 230                 235                 240

Leu Pro Gly Ser Val Leu Gln Met Pro Gly Thr Ala Ala Pro Ala Pro
                245                 250                 255

Glu Ser Leu His Gly Arg
            260
```

```
<210> SEQ ID NO 57
<211> LENGTH: 1000
<212> TYPE: DNA
<213> ORGANISM: Mycobacterium tuberculosis

<400> SEQUENCE: 57
cgaggagacc gacgatctgc tcgacgaaat cgacgacgtc ctcgaggaga acgccgagga      60
cttcgtccgc gcatacgtcc aaaagggcgg acagtgacct ggccgttgcc cgatcgcctg     120
tccattaatt cactctctgg aacacccgct gtagacctat cttctttcac tgacttcctg     180
cgccgccagg cgccggagtt gctgccggca agcatcagcg gcggtgcgcc actcgcaggc     240
ggcgatgcgc aactgccgca cggcaccacc attgtcgcgc tgaaataccc cggcggtgtt     300
gtcatggcgg gtgaccggcg ttcgacgcag ggcaacatga tttctgggcg tgatgtgcgc     360
aaggtgtata tcaccgatga ctacaccgct accggcatcg ctggcacggc tgcggtcgcg     420
gttgagtttg cccggctgta tgccgtggaa cttgagcact acgagaagct cgagggtgtg     480
ccgctgacgt ttgccggcaa aatcaaccgg ctggcgatta tggtgcgtgg caatctggcg     540
gccgcgatgc agggtctgct ggcgttgccg ttgctggcgg gctacgacat tcatgcgtct     600
gacccgcaga gcgcgggtcg tatcgtttcg ttcgacgccg ccggcggttg gaacatcgag     660
gaagagggct atcaggcggt gggctcgggt tcgctgttcg cgaagtcgtc gatgaagaag     720
ttgtattcgc aggttaccga cggtgattcg gggctgcggg tggcggtcga ggcgctctac     780
gacgccgccg acgacgactc cgccaccggc ggtccggacc tggtgcgggg catctttccg     840
acggcggtga tcatcgacgc cgacggggcg gttgacgtgc cggagagccg gattgccgaa     900
ttggcccgcg cgatcatcga aagccgttcg ggtgcggata ctttcggctc cgatggcggt     960
gagaagtgag ttttccgtat ttcatctcgc ctgagcaggc                          1000
```

<210> SEQ ID NO 58
<211> LENGTH: 291
<212> TYPE: PRT
<213> ORGANISM: Mycobacterium tuberculosis

<400> SEQUENCE: 58

Met Thr Trp Pro Leu Pro Asp Arg Leu Ser Ile Asn Ser Leu Ser Gly
1               5                   10                  15

Thr Pro Ala Val Asp Leu Ser Ser Phe Thr Asp Phe Leu Arg Arg Gln
            20                  25                  30

Ala Pro Glu Leu Leu Pro Ala Ser Ile Ser Gly Gly Ala Pro Leu Ala
        35                  40                  45

Gly Gly Asp Ala Gln Leu Pro His Gly Thr Thr Ile Val Ala Leu Lys
    50                  55                  60

Tyr Pro Gly Gly Val Val Met Ala Gly Asp Arg Arg Ser Thr Gln Gly
65                  70                  75                  80

Asn Met Ile Ser Gly Arg Asp Val Arg Lys Val Tyr Ile Thr Asp Asp
                85                  90                  95

Tyr Thr Ala Thr Gly Ile Ala Gly Thr Ala Ala Val Ala Val Glu Phe
            100                 105                 110

Ala Arg Leu Tyr Ala Val Glu Leu Glu His Tyr Glu Lys Leu Glu Gly
        115                 120                 125

Val Pro Leu Thr Phe Ala Gly Lys Ile Asn Arg Leu Ala Ile Met Val
    130                 135                 140

Arg Gly Asn Leu Ala Ala Ala Met Gln Gly Leu Leu Ala Leu Pro Leu
145                 150                 155                 160

Leu Ala Gly Tyr Asp Ile His Ala Ser Asp Pro Gln Ser Ala Gly Arg
                165                 170                 175

Ile Val Ser Phe Asp Ala Ala Gly Gly Trp Asn Ile Glu Glu Gly
            180                 185                 190

Tyr Gln Ala Val Gly Ser Gly Ser Leu Phe Ala Lys Ser Ser Met Lys
        195                 200                 205

Lys Leu Tyr Ser Gln Val Thr Asp Gly Asp Ser Gly Leu Arg Val Ala
    210                 215                 220

Val Glu Ala Leu Tyr Asp Ala Ala Asp Asp Ser Ala Thr Gly Gly
225                 230                 235                 240

Pro Asp Leu Val Arg Gly Ile Phe Pro Thr Ala Val Ile Ile Asp Ala
                245                 250                 255

Asp Gly Ala Val Asp Val Pro Glu Ser Arg Ile Ala Glu Leu Ala Arg
            260                 265                 270

Ala Ile Ile Glu Ser Arg Ser Gly Ala Asp Thr Phe Gly Ser Asp Gly
        275                 280                 285

Gly Glu Lys
    290

<210> SEQ ID NO 59
<211> LENGTH: 900
<212> TYPE: DNA
<213> ORGANISM: Mycobacterium tuberculosis

<400> SEQUENCE: 59
ttggcccgcg cgatcatcga aagccgttcg ggtgcggata ctttcggctc cgatggcggt      60
gagaagtgag tttccgtat tcatctcgc ctgagcaggc gatgcgcgag cgcagcgagt     120
tggcgcgtaa gggcattgcg cggggccaaaa gcgtggtggc gctggcctat gccggtggtg     180
tgctgttcgt cgcggagaat ccgtcgcggt cgctgcagaa gatcagtgag ctctacgatc     240

-continued

```
gggtgggttt tgcggctgcg ggcaagttca acgagttcga caatttgcgc cgcggcggga      300
tccagttcgc cgacacccgc ggttacgcct atgaccgtcg tgacgtcacg ggtcggcagt      360
tggccaatgt ctacgcgcag actctaggca ccatcttcac cgaacaggcc aagccctacg      420
aggttgagtt gtgtgtggcc gaggtggcgc attacggcga gacgaaacgc cctgagttgt      480
atcgtattac ctacgacggg tcgatcgccg acgagccgca tttcgtggtg atgggcggca      540
ccacggagcc gatcgccaac gcgctcaaag agtcgtatgc cgagaacgcc agcctgaccg      600
acgccctgcg tatcgcggtc gctgcattgc gggccggcag tgccgacacc tcgggtggtg      660
atcaacccac ccttggcgtg gccagcttag aggtggccgt tctcgatgcc aaccggccac      720
ggcgcgcgtt ccggcgcatc accggctccg ccctgcaagc gttgctggta gaccaggaaa      780
gcccgcagtc tgacggcgaa tcgtcgggct gagtccgaaa gtccgacgcg tgtctgggac      840
cccgctgcga cgttaactgc gcctaacccc ggctcgacgc gtcgccggcc gtcctgactt      900
```

<210> SEQ ID NO 60
<211> LENGTH: 248
<212> TYPE: PRT
<213> ORGANISM: Mycobacterium tuberculosis

<400> SEQUENCE: 60

```
Met Ser Phe Pro Tyr Phe Ile Ser Pro Glu Gln Ala Met Arg Glu Arg
 1               5                  10                  15

Ser Glu Leu Ala Arg Lys Gly Ile Ala Arg Ala Lys Ser Val Val Ala
            20                  25                  30

Leu Ala Tyr Ala Gly Gly Val Leu Phe Val Ala Glu Asn Pro Ser Arg
        35                  40                  45

Ser Leu Gln Lys Ile Ser Glu Leu Tyr Asp Arg Val Gly Phe Ala Ala
    50                  55                  60

Ala Gly Lys Phe Asn Glu Phe Asp Asn Leu Arg Arg Gly Gly Ile Gln
65                  70                  75                  80

Phe Ala Asp Thr Arg Gly Tyr Ala Tyr Asp Arg Arg Asp Val Thr Gly
                85                  90                  95

Arg Gln Leu Ala Asn Val Tyr Ala Gln Thr Leu Gly Thr Ile Phe Thr
            100                 105                 110

Glu Gln Ala Lys Pro Tyr Glu Val Glu Leu Cys Val Ala Glu Val Ala
        115                 120                 125

His Tyr Gly Glu Thr Lys Arg Pro Glu Leu Tyr Arg Ile Thr Tyr Asp
    130                 135                 140

Gly Ser Ile Ala Asp Glu Pro His Phe Val Val Met Gly Gly Thr Thr
145                 150                 155                 160

Glu Pro Ile Ala Asn Ala Leu Lys Glu Ser Tyr Ala Glu Asn Ala Ser
                165                 170                 175

Leu Thr Asp Ala Leu Arg Ile Ala Val Ala Ala Leu Arg Ala Gly Ser
            180                 185                 190

Ala Asp Thr Ser Gly Gly Asp Gln Pro Thr Leu Gly Val Ala Ser Leu
        195                 200                 205

Glu Val Ala Val Leu Asp Ala Asn Arg Pro Arg Arg Ala Phe Arg Arg
    210                 215                 220

Ile Thr Gly Ser Ala Leu Gln Ala Leu Leu Val Asp Gln Glu Ser Pro
225                 230                 235                 240

Gln Ser Asp Gly Glu Ser Ser Gly
                245
```

<210> SEQ ID NO 61
<211> LENGTH: 1560
<212> TYPE: DNA
<213> ORGANISM: Mycobacterium tuberculosis

<400> SEQUENCE: 61

```
gagtcattgc ctggtcggcg tcattccgta ctagtcggtt gtcggacttg acctactggg      60
tcaggccgac gagcactcga ccattagggt aggggccgtg acccactatg acgtcgtcgt     120
tctcggagcc ggtcccggcg ggtatgtcgc ggcgattcgc gccgcacagc tcggcctgag     180
cactgcaatc gtcgaaccca agtactgggg cggagtatgc ctcaatgtcg gctgtatccc     240
atccaaggcg ctgttgcgca acgccgaact ggtccacatc ttccaaggac gccaaagc      300
atttggcatc agcggcgagg tgaccttcga ctacggcatc gcctatgacc gcagccgaaa     360
ggtagccgag ggcagggtgg ccggtgtgca cttcctgatg aagaagaaca agatcaccga     420
gatccacggg tacggcacat ttgccgacgc caacacgttg ttggttgatc tcaacgacgg     480
cggtacagaa tcggtcacgt tcgacaacgc catcatcgcg accggcagta gcacccggct     540
ggttcccggc acctcactgt cggccaacgt agtcacctac gaggaacaga tcctgtcccg     600
agagctgccg aaatcgatca ttattgccgg agctggtgcc attggcatgg agttcggcta     660
cgtgctgaag aactacggcg ttgacgtgac catcgtggaa ttccttccgc gggcgctgcc     720
caacgaggac gccgatgtgt ccaaggagat cgagaagcag ttcaaaaagc tgggtgtcac     780
gatcctgacc gccacgaagg tcgagtccat cgccgatggc gggtcgcagg tcaccgtgac     840
cgtcaccaag gacggcgtgg cgcaagagct taaggcggaa aaggtgttgc aggccatcgg     900
atttgcgccc aacgtcgaag ggtacgggct ggacaaggca ggcgtcgcgc tgaccgaccg     960
caaggctatc ggtgtcgacg actacatgcg taccaacgtg ggccacatct acgctatcgg    1020
cgatgtcaat ggattactgc agctggcgca cgtcgccgag gcacaaggcg tggtagccgc    1080
cgaaaccatt gccggtgcag agactttgac gctgggcgac catcggatgt gccgcgcgc    1140
gacgttctgt cagccaaacg ttgccagctt cgggctcacc gagcagcaag cccgcaacga    1200
aggttacgac gtggtggtgg ccaagttccc gttcacggcc aacgccaagg cgcacggcgt    1260
gggtgacccc agtgggttcg tcaagctggt ggccgacgcc aagcacggcg agctactggg    1320
tgggcacctg gtcggccacg acgtggccga gctgctgccg gagctcacgc tggcgcagag    1380
gtgggacctg accgccagcg agctggctcg caacgtccac acccacccaa cgatgtctga    1440
ggcgctgcag gagtgcttcc acggcctggt tgggcacatg atcaattctct gagcggctca    1500
tgacgaggcg cgcgagcact gaccccccc agatcatcat gggtgccatc ggtggtgtgg    1560
```

<210> SEQ ID NO 62
<211> LENGTH: 464
<212> TYPE: PRT
<213> ORGANISM: Mycobacterium tuberculosis

<400> SEQUENCE: 62

```
Met Thr His Tyr Asp Val Val Leu Gly Ala Gly Pro Gly Gly Tyr
  1               5                  10                  15

Val Ala Ala Ile Arg Ala Ala Gln Leu Gly Leu Ser Thr Ala Ile Val
                 20                  25                  30

Glu Pro Lys Tyr Trp Gly Gly Val Cys Leu Asn Val Gly Cys Ile Pro
             35                  40                  45

Ser Lys Ala Leu Leu Arg Asn Ala Glu Leu Val His Ile Phe Thr Lys
         50                  55                  60
```

-continued

```
Asp Ala Lys Ala Phe Gly Ile Ser Gly Glu Val Thr Phe Asp Tyr Gly
 65                  70                  75                  80

Ile Ala Tyr Asp Arg Ser Arg Lys Val Ala Glu Gly Arg Val Ala Gly
             85                  90                  95

Val His Phe Leu Met Lys Lys Asn Lys Ile Thr Glu Ile His Gly Tyr
            100                 105                 110

Gly Thr Phe Ala Asp Ala Asn Thr Leu Leu Val Asp Leu Asn Asp Gly
            115                 120                 125

Gly Thr Glu Ser Val Thr Phe Asp Asn Ala Ile Ile Ala Thr Gly Ser
        130                 135                 140

Ser Thr Arg Leu Val Pro Gly Thr Ser Leu Ser Ala Asn Val Val Thr
145                 150                 155                 160

Tyr Glu Glu Gln Ile Leu Ser Arg Glu Leu Pro Lys Ser Ile Ile Ile
                165                 170                 175

Ala Gly Ala Gly Ala Ile Gly Met Glu Phe Gly Tyr Val Leu Lys Asn
                180                 185                 190

Tyr Gly Val Asp Val Thr Ile Val Glu Phe Leu Pro Arg Ala Leu Pro
            195                 200                 205

Asn Glu Asp Ala Asp Val Ser Lys Glu Ile Glu Lys Gln Phe Lys Lys
        210                 215                 220

Leu Gly Val Thr Ile Leu Thr Ala Thr Lys Val Glu Ser Ile Ala Asp
225                 230                 235                 240

Gly Gly Ser Gln Val Thr Val Thr Val Thr Lys Asp Gly Val Ala Gln
                245                 250                 255

Glu Leu Lys Ala Glu Lys Val Leu Gln Ala Ile Gly Phe Ala Pro Asn
            260                 265                 270

Val Glu Gly Tyr Gly Leu Asp Lys Ala Gly Val Ala Leu Thr Asp Arg
        275                 280                 285

Lys Ala Ile Gly Val Asp Asp Tyr Met Arg Thr Asn Val Gly His Ile
290                 295                 300

Tyr Ala Ile Gly Asp Val Asn Gly Leu Leu Gln Leu Ala His Val Ala
305                 310                 315                 320

Glu Ala Gln Gly Val Val Ala Ala Glu Thr Ile Ala Gly Ala Glu Thr
                325                 330                 335

Leu Thr Leu Gly Asp His Arg Met Leu Pro Arg Ala Thr Phe Cys Gln
            340                 345                 350

Pro Asn Val Ala Ser Phe Gly Leu Thr Glu Gln Gln Ala Arg Asn Glu
        355                 360                 365

Gly Tyr Asp Val Val Ala Lys Phe Pro Phe Thr Ala Asn Ala Lys
370                 375                 380

Ala His Gly Val Gly Asp Pro Ser Gly Phe Val Lys Leu Val Ala Asp
385                 390                 395                 400

Ala Lys His Gly Glu Leu Leu Gly Gly His Leu Val Gly His Asp Val
            405                 410                 415

Ala Glu Leu Leu Pro Glu Leu Thr Leu Ala Gln Arg Trp Asp Leu Thr
        420                 425                 430

Ala Ser Glu Leu Ala Arg Asn Val His Thr His Pro Thr Met Ser Glu
    435                 440                 445

Ala Leu Gln Glu Cys Phe His Gly Leu Val Gly His Met Ile Asn Phe
450                 455                 460
```

<210> SEQ ID NO 63
<211> LENGTH: 550
<212> TYPE: DNA
<213> ORGANISM: Mycobacterium tuberculosis

<400> SEQUENCE: 63

```
ggcccggctc gcggccgccc tgcaggaaaa gaaggcctgc ccaggcccag actcagccga      60
gtagtcaccc agtaccccac accaggaagg accgcccatc atggcaaagc tctccaccga    120
cgaactgctg gacgcgttca aggaaatgac cctgttggag ctctccgact tcgtcaagaa    180
gttcgaggag accttcgagg tcaccgccgc cgctccagtc gccgtcgccg ccgcggtgc     240
cgccccggcc ggtgccgccg tcgaggctgc cgaggagcag tccgagttcg acgtgatcct    300
tgaggccgcc ggcgacaaga agatcggcgt catcaaggtg gtccgggaga tcgtttccgg    360
cctgggcctc aaggaggcca aggacctggt cgacggcgcg cccaagccgc tgctggagaa    420
ggtcgccaag gaggccgccg acgaggccaa ggccaagctg gaggccgccg gcgccaccgt    480
caccgtcaag tagctctgcc cagcgtgttc ttttgcgtct gctcggcccg tagcgaacac    540
tgcgcccgct                                                            550
```

<210> SEQ ID NO 64
<211> LENGTH: 130
<212> TYPE: PRT
<213> ORGANISM: Mycobacterium tuberculosis

<400> SEQUENCE: 64

Met Ala Lys Leu Ser Thr Asp Glu Leu Leu Asp Ala Phe Lys Glu Met
1               5                   10                  15

Thr Leu Leu Glu Leu Ser Asp Phe Val Lys Lys Phe Glu Glu Thr Phe
            20                  25                  30

Glu Val Thr Ala Ala Ala Pro Val Ala Val Ala Ala Ala Gly Ala Ala
        35                  40                  45

Pro Ala Gly Ala Ala Val Glu Ala Ala Glu Glu Gln Ser Glu Phe Asp
    50                  55                  60

Val Ile Leu Glu Ala Ala Gly Asp Lys Lys Ile Gly Val Ile Lys Val
65                  70                  75                  80

Val Arg Glu Ile Val Ser Gly Leu Gly Leu Lys Glu Ala Lys Asp Leu
                85                  90                  95

Val Asp Gly Ala Pro Lys Pro Leu Leu Glu Lys Val Ala Lys Glu Ala
            100                 105                 110

Ala Asp Glu Ala Lys Ala Lys Leu Glu Ala Ala Gly Ala Thr Val Thr
        115                 120                 125

Val Lys
    130

<210> SEQ ID NO 65
<211> LENGTH: 900
<212> TYPE: DNA
<213> ORGANISM: Mycobacterium tuberculosis

<400> SEQUENCE: 65

```
tgaacgccat cgggtccaac gaacgcagcg ctacctgatc accaccgggt ctgttagggc      60
tcttccccag gtcgtacagt cgggccatgg ccattgaggt ttcggtgttg cgggttttca    120
ccgattcaga cgggaatttc ggtaatccgc tgggggtgat caacgccagc aaggtcgaac    180
accgcgacag gcagcagctg gcagcccaat cgggctacag cgaaaccata ttcgtcgatc    240
ttcccagccc cggctcaacc accgcacacg ccaccatcca tactccccgc accgaaattc    300
```

```
cgttcgccgg acacccgacc gtgggagcgt cctggtggct gcgcgagagg gggacgccaa      360
ttaacacgct gcaggtgccg gccggcatcg tccaggtgag ctaccacggt gatctcaccg      420
ccatcagcgc ccgctcggaa tgggcacccg agttcgccat ccacgacctg gattcacttg      480
atgcgcttgc cgccgccgac cccgccgact tccggacga catcgcgcac tacctctgga       540
cctggaccga ccgctccgct ggctcgctgc gcgcccgcat gtttgccgcc aacttgggcg      600
tcaccgaaga cgaagcgacc ggtgccgcgg ccatccggga taccgattac ctcagccgtg      660
acctcaccat cacccagggc aaaggatcgt tgatccacac cacctggagt cccgagggct      720
gggttcgggt agccggccga gttgtcagcg acggtgtggc acaactcgac tgacgtagag      780
ctcagcgctg ccgatgcaac acggcggcaa ggtgatcctg caggggttgc ccgaccgcgc      840
gcatctgcaa cgagtacgaa agctcgtcgc cgtcgatgcg gtaggaacgg tcaagggcgg      900
```

<210> SEQ ID NO 66
<211> LENGTH: 228
<212> TYPE: PRT
<213> ORGANISM: Mycobacterium tuberculosis

<400> SEQUENCE: 66

```
Met Ala Ile Glu Val Ser Val Leu Arg Val Phe Thr Asp Ser Asp Gly
1               5                   10                  15

Asn Phe Gly Asn Pro Leu Gly Val Ile Asn Ala Ser Lys Val Glu His
                20                  25                  30

Arg Asp Arg Gln Gln Leu Ala Ala Gln Ser Gly Tyr Ser Glu Thr Ile
            35                  40                  45

Phe Val Asp Leu Pro Ser Pro Gly Ser Thr Thr Ala His Ala Thr Ile
        50                  55                  60

His Thr Pro Arg Thr Glu Ile Pro Phe Ala Gly His Pro Thr Val Gly
65                  70                  75                  80

Ala Ser Trp Trp Leu Arg Glu Arg Gly Thr Pro Ile Asn Thr Leu Gln
                85                  90                  95

Val Pro Ala Gly Ile Val Gln Val Ser Tyr His Gly Asp Leu Thr Ala
            100                 105                 110

Ile Ser Ala Arg Ser Glu Trp Ala Pro Glu Phe Ala Ile His Asp Leu
        115                 120                 125

Asp Ser Leu Asp Ala Leu Ala Ala Asp Pro Ala Asp Phe Pro Asp
    130                 135                 140

Asp Ile Ala His Tyr Leu Trp Thr Trp Thr Asp Arg Ser Ala Gly Ser
145                 150                 155                 160

Leu Arg Ala Arg Met Phe Ala Ala Asn Leu Gly Val Thr Glu Asp Glu
                165                 170                 175

Ala Thr Gly Ala Ala Ala Ile Arg Ile Thr Asp Tyr Leu Ser Arg Asp
            180                 185                 190

Leu Thr Ile Thr Gln Gly Lys Gly Ser Leu Ile His Thr Thr Trp Ser
        195                 200                 205

Pro Glu Gly Trp Val Arg Val Ala Gly Arg Val Val Ser Asp Gly Val
    210                 215                 220

Ala Gln Leu Asp
225
```

<210> SEQ ID NO 67
<211> LENGTH: 500
<212> TYPE: DNA
<213> ORGANISM: Mycobacterium tuberculosis -continued

```
<400> SEQUENCE: 67
gtttgtggtg tcggtggtct gggggggcgcc aactgggatt cggttggggt gggtgcaggt    60
ccggcgatgg gcatcggagg tgtgggtggt ttgggtgggg ccggttcggg tccggcgatg   120
ggcatggggg gtgtgggtgg tttggtgggg gccggttcgg gtccggcgat gggcatgggg   180
ggtgtgggtg gtttagatgc ggccggttcc ggcgagggcg gctctcctgc ggcgatcggc   240
atcggagttg gcggaggcgg aggtgggggt ggggtggcg gcgcgggc cgacacgaac     300 cgctccgaca ggtcgtcgga cgtcgggggc ggagtctggc cgttgggctt cggtaggttt   360
gccgatgcgg gcgccggcgg aaacgaagca ctggggtcga gaacggctg cgctgccata   420 tcgtccggag cttccatacc ttcgtgcggc cggaagagct tgtcgtagtc ggccgccatg   480
acaacctctc agagtgcgct                                               500

<210> SEQ ID NO 68
<211> LENGTH: 139
<212> TYPE: PRT
<213> ORGANISM: Mycobacterium tuberculosis

<400> SEQUENCE: 68

Met Gly Ala Gly Pro Ala Met Gly Ile Gly Val Gly Gly Leu Gly
 1               5                  10                  15

Gly Ala Gly Ser Gly Pro Ala Met Gly Met Gly Val Gly Gly Leu
                20                  25                  30

Gly Gly Ala Gly Ser Gly Pro Ala Met Gly Met Gly Val Gly Gly
             35                  40                  45

Leu Asp Ala Ala Gly Ser Gly Glu Gly Gly Ser Pro Ala Ala Ile Gly
     50                  55                  60

Ile Gly Val Gly Gly Gly Gly Gly Gly Gly Gly Gly Gly Gly Gly
 65                  70                  75                  80

Ala Asp Thr Asn Arg Ser Asp Arg Ser Ser Asp Val Gly Gly Gly Val
                 85                  90                  95

Trp Pro Leu Gly Phe Gly Arg Phe Ala Asp Ala Gly Ala Gly Gly Asn
            100                 105                 110

Glu Ala Leu Gly Ser Lys Asn Gly Cys Ala Ala Ile Ser Ser Gly Ala
        115                 120                 125

Ser Ile Pro Ser Cys Gly Arg Lys Ser Leu Ser
    130                 135

<210> SEQ ID NO 69
<211> LENGTH: 2050
<212> TYPE: DNA
<213> ORGANISM: Mycobacterium tuberculosis

<400> SEQUENCE: 69
agcgcactct gagaggttgt catggcggcc gactacgaca agctcttccg gccgcacgaa    60
ggtatggaag ctccggacga tatggcagcg cagccgttct tcgacccccag tgcttcgttt   120 ccgccggcgc ccgcatcggc aaacctaccg aagcccaacg ccagactcc gccccgacg   180 tccgacgacc tgtcggagcg gttcgtgtcg gccccgccgc cgccaccccc accccacct    240 ccgcctccgc caactccgat gccgatcgcc gcaggagagc cgccctcgcc ggaaccggcc   300
gcatctaaac cacccacacc cccatgccc atcgccggac ccgaaccggc cccacccaaa   360
ccacccacac ccccccatgcc catcgccgga cccgaaccgg ccccacccaa ccacccaca   420 cctccgatgc ccatcgccgg acctgcaccc accccaaccg aatcccagtt ggcgcccccc   480
```

```
agaccaccga caccacaaac gccaaccgga gcgccgcagc aaccggaatc accggcgccc    540
cacgtaccct cgcacgggcc acatcaaccc cggcgcaccg caccagcacc gccctgggca    600
aagatgccaa tcggcgaacc cccgcccgct ccgtccagac cgtctgcgtc cccggccgaa    660
ccaccgaccc ggcctgcccc ccaacactcc cgacgtgcgc gccggggtca ccgctatcgc    720
acagacaccg aacgaaacgt cgggaaggta gcaactggtc catccatcca ggcgcggctg    780
cgggcagagg aagcatccgg cgcgcagctc gcccccggaa cggagccctc gccagcgccg    840
ttgggccaac cgagatcgta tctggctccg cccaccccgcc ccgcgccgac agaacctccc    900
cccagccccct cgccgcagcg caactccggt cggcgtgccg agcgacgcgt ccaccccgat    960
ttagccgccc aacatgccgc ggcgcaacct gattcaatta cggccgcaac cactggcggt   1020
cgtcgccgca agcgtgcagc gccggatctc gacgcgcaca agaaatcctt aaggccggcg   1080
gccaaggggc cgaaggtgaa gaaggtgaag ccccagaaac cgaaggccac gaagccgccc   1140
aaagtggtgt cgcagcgcgg ctggcgacat tgggtgcatg cgttgacgcg aatcaacctg   1200
ggcctgtcac ccgacgagaa gtacgagctg gacctgcacg ctcgagtccg ccgcaatccc   1260
cgcgggtcgt atcagatcgc cgtcgtcggt ctcaaaggtg gggctggcaa accacgctg    1320
acagcagcgt tggggtcgac gttggctcag gtgcgggccg accggatcct ggctctagac   1380
gcggatccag cgccggaaa cctcgccgat cgggtagggc gacaatcggg cgcgaccatc    1440
gctgatgtgc ttgcagaaaa agagctgtcg cactacaacg acatccgcgc acacactagc   1500
gtcaatgcgg tcaatctgga agtgctgccg gcaccggaat acagctcggc gcagcgcgcg   1560
ctcagcgacg ccgactggca tttcatcgcc gatcctgcgt cgaggtttta caacctcgtc   1620
ttggctgatt gtggggccgg cttcttcgac ccgctgaccc gcggcgtgct gtccacggtg   1680
tccggtgtcg tggtcgtggc aagtgtctca atcgacggcg cacaacaggc gtcggtcgcg   1740
ttggactggt tgcgcaacaa cggttaccaa gatttggcga gccgcgcatg cgtggtcatc   1800
aatcacatca tgccgggaga acccaatgtc gcagttaaag acctggtgcg gcatttcgaa   1860
cagcaagttc aacccggccg ggtcgtggtc atgccgtggg acaggcacat tgcggccgga   1920
accgagattt cactcgactt gctcgaccct atctacaagc gcaaggtcct cgaattggcc   1980
gcagcgctat ccgacgattt cgagagggct ggacgtcgtt gagcgcacct gctgttgctg   2040
ctggtcctac                                                          2050
```

<210> SEQ ID NO 70
<211> LENGTH: 666
<212> TYPE: PRT
<213> ORGANISM: Mycobacterium tuberculosis

<400> SEQUENCE: 70

```
Met Ala Ala Asp Tyr Asp Lys Leu Phe Arg Pro His Glu Gly Met Glu
 1               5                  10                  15

Ala Pro Asp Asp Met Ala Ala Gln Pro Phe Phe Asp Pro Ser Ala Ser
                20                  25                  30

Phe Pro Pro Ala Pro Ala Ser Ala Asn Leu Pro Lys Pro Asn Gly Gln
            35                  40                  45

Thr Pro Pro Thr Ser Asp Asp Leu Ser Glu Arg Phe Val Ser Ala
        50                  55                  60

Pro Pro Pro Pro Pro Pro Pro Pro Pro Pro Thr Pro Met
 65                  70                  75                  80

Pro Ile Ala Ala Gly Glu Pro Pro Ser Pro Glu Pro Ala Ala Ser Lys
                85                  90                  95
```

```
Pro Pro Thr Pro Pro Met Pro Ile Ala Gly Pro Glu Pro Ala Pro Pro
            100                 105                 110

Lys Pro Pro Thr Pro Pro Met Pro Ile Ala Gly Pro Glu Pro Ala Pro
            115                 120                 125

Pro Lys Pro Pro Thr Pro Pro Met Pro Ile Ala Gly Pro Ala Pro Thr
            130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
            165                 170                 175

Ser His Gly Pro His Gln Pro Arg Arg Thr Ala Pro Ala Pro Pro Trp
            180                 185                 190

Ala Lys Met Pro Ile Gly Glu Pro Pro Ala Pro Ser Arg Pro Ser
            195                 200                 205

Ala Ser Pro Ala Glu Pro Pro Thr Arg Pro Ala Pro Gln His Ser Arg
    210                 215                 220

Arg Ala Arg Arg Gly His Arg Tyr Arg Thr Asp Thr Glu Arg Asn Val
225                 230                 235                 240

Gly Lys Val Ala Thr Gly Pro Ser Ile Gln Ala Arg Leu Arg Ala Glu
            245                 250                 255

Glu Ala Ser Gly Ala Gln Leu Ala Pro Gly Thr Glu Pro Ser Pro Ala
            260                 265                 270

Pro Leu Gly Gln Pro Arg Ser Tyr Leu Ala Pro Pro Thr Arg Pro Ala
            275                 280                 285

Pro Thr Glu Pro Pro Ser Pro Ser Pro Gln Arg Asn Ser Gly Arg
            290                 295                 300

Arg Ala Glu Arg Val His Pro Asp Leu Ala Ala Gln His Ala Ala
305                 310                 315                 320

Ala Gln Pro Asp Ser Ile Thr Ala Ala Thr Thr Gly Arg Arg Arg
            325                 330                 335

Lys Arg Ala Ala Pro Asp Leu Asp Ala Thr Gln Lys Ser Leu Arg Pro
            340                 345                 350

Ala Ala Lys Gly Pro Lys Val Lys Val Lys Pro Gln Lys Pro Lys
            355                 360                 365

Ala Thr Lys Pro Pro Lys Val Val Ser Gln Arg Gly Trp Arg His Trp
370                 375                 380

Val His Ala Leu Thr Arg Ile Asn Leu Gly Leu Ser Pro Asp Glu Lys
385                 390                 395                 400

Tyr Glu Leu Asp Leu His Ala Arg Val Arg Arg Asn Pro Arg Gly Ser
            405                 410                 415

Tyr Gln Ile Ala Val Val Gly Leu Lys Gly Gly Ala Gly Lys Thr Thr
            420                 425                 430

Leu Thr Ala Ala Leu Gly Ser Thr Leu Ala Gln Val Arg Ala Asp Arg
            435                 440                 445

Ile Leu Ala Leu Asp Ala Asp Pro Gly Ala Gly Asn Leu Ala Asp Arg
            450                 455                 460

Val Gly Arg Gln Ser Gly Ala Thr Ile Ala Asp Val Leu Ala Glu Lys
465                 470                 475                 480

Glu Leu Ser His Tyr Asn Asp Ile Arg Ala His Thr Ser Val Asn Ala
            485                 490                 495

Val Asn Leu Glu Val Leu Pro Ala Pro Glu Tyr Ser Ser Ala Gln Arg
            500                 505                 510
```

-continued

```
Ala Leu Ser Asp Ala Asp Trp His Phe Ile Ala Asp Pro Ala Ser Arg
        515                 520                 525

Phe Tyr Asn Leu Val Leu Ala Asp Cys Gly Ala Gly Phe Phe Asp Pro
        530                 535                 540

Leu Thr Arg Gly Val Leu Ser Thr Val Ser Gly Val Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
                580                 585                 590

Ile Asn His Ile Met Pro Gly Glu Pro Asn Val Ala Val Lys Asp Leu
                595                 600                 605

Val Arg His Phe Glu Gln Gln Val Gln Pro Arg Val Val Val Val Met
        610                 615                 620

Pro Trp Asp Arg His Ile Ala Ala Gly Thr Glu Ile Ser Leu Asp Leu
625                 630                 635                 640

Leu Asp Pro Ile Tyr Lys Arg Lys Val Leu Glu Leu Ala Ala Ala Leu
                645                 650                 655

Ser Asp Asp Phe Glu Arg Ala Gly Arg Arg
        660                 665

<210> SEQ ID NO 71
<211> LENGTH: 1890
<212> TYPE: DNA
<213> ORGANISM: Mycobacterium tuberculosis

<400> SEQUENCE: 71
gcagcgatga ggaggagcgg cgccaacggc ccgcgccggc gacgatgcaa agcgcagcga      60
tgaggaggag cggcgcgcat gactgctgaa ccggaagtac ggacgctgcg cgaggttgtg     120
ctggaccagc tcggcactgc tgaatcgcgt gcgtacaaga tgtggctgcc gccgttgacc     180
aatccggtcc cgctcaacga gctcatcgcc cgtgatcggc gacaacccct gcgatttgcc     240
ctggggatca tggatgaacc cgccgccat ctacaggatg tgtggggcgt agacgttccc     300
ggggccggcg gcaacatcgg tattggggc gcacctcaaa ccgggaagtc gacgctactg     360
cagacgatgg tgatgtcggc cgccgccaca cactcaccgc gcaacgttca gttctattgc     420
atcgacctag gtggcggcgg gctgatctat ctcgaaaacc ttccacacgt cggtggggta     480
gccaatcggt ccgagcccga caaggtcaac cgggtggtcg cagagatgca agccgtcatg     540
cggcaacggg aaaccacctt caaggaacac cgagtgggct cgatcgggat gtaccggcag     600
ctgcgtgacg atccaagtca acccgttgcg tccgatccat acggcgacgt ctttctgatc     660
atcgacggat ggcccggttt tgtcggcgag ttccccgacc ttgaggggca ggttcaagat     720
ctggccgccc aggggctggg gttcggcgtc cacgtcatca tctccacgcc acgctggaca     780
gagctgaagt cgcgtgttcg cgactacctc ggcaccaaga tcgagttccg gcttggtgac     840
gtcaatgaaa cccagatcga ccggattacc cgcgagatcc ggcgaatcg tccgggtcgg     900 gcagtgtcga tggaaaagca ccatctgatg atcggcgtgc caggttcga cggcgtgcac     960 agcgccgata acctggtgga ggcgatcacc gcggggtga cgcagatcgc ttcccagcac    1020
accgaacagg cacctccggt gcgggtcctg ccggagcgta tccacctgca cgaactcgac    1080
ccgaacccgc cgggaccaga gtccgactac cgcactcgct gggagattcc gatcggcttg    1140
cgcgagacgg acctgacgcc ggctcactgc cacatgcaca cgaacccgca cctactgatc    1200
ttcggtgcgg ccaaatcggg caagacgacc attgcccacg cgatcgcgcg cgccatttgt    1260
```

-continued

```
gcccgaaaca gtccccagca ggtgcggttc atgctcgcgg actaccgctc gggcctgctg    1320
gacgcggtgc cggacaccca tctgctgggc gccggcgcga tcaaccgcaa cagcgcgtcg    1380
ctagacgagg ccgctcaagc actggcggtc aacctgaaga agcggttgcc gccgaccgac    1440
ctgacgacgg cgcagctacg ctcgcgttcg tggtggagcg gatttgacgt cgtgcttctg    1500
gtcgacgatt ggcacatgat cgtgggtgcc gccgggggga tgccgccgat ggcaccgctg    1560
gccccgttat tgccggcggc ggcagatatc gggttgcaca tcattgtcac ctgtcagatg    1620
agccaggctt acaaggcaac catggacaag ttcgtcggcg ccgcattcgg gtcgggcgct    1680
ccgacaatgt tcctttcggg cgagaagcag gaattcccat ccagtgagtt caaggtcaag    1740
cggcgccccc ctggccaggc atttctcgtc tcgccagacg gcaaagaggt catccaggcc    1800
ccctacatcg agcctccaga agaagtgttc gcagcacccc caagcgccgg ttaagattat    1860
ttcattgccg gtgtagcagg acccgagctc                                     1890
```

<210> SEQ ID NO 72
<211> LENGTH: 591
<212> TYPE: PRT
<213> ORGANISM: Mycobacterium tuberculosis

<400> SEQUENCE: 72

```
Met Thr Ala Glu Pro Glu Val Arg Thr Leu Arg Glu Val Val Leu Asp
  1               5                  10                  15

Gln Leu Gly Thr Ala Glu Ser Arg Ala Tyr Lys Met Trp Leu Pro Pro
                 20                  25                  30

Leu Thr Asn Pro Val Pro Leu Asn Glu Leu Ile Ala Arg Asp Arg Arg
             35                  40                  45

Gln Pro Leu Arg Phe Ala Leu Gly Ile Met Asp Glu Pro Arg Arg His
         50                  55                  60

Leu Gln Asp Val Trp Gly Val Asp Val Ser Gly Ala Gly Asn Ile
 65                  70                  75                  80

Gly Ile Gly Gly Ala Pro Gln Thr Gly Lys Ser Thr Leu Leu Gln Thr
                 85                  90                  95

Met Val Met Ser Ala Ala Ala Thr His Ser Pro Arg Asn Val Gln Phe
            100                 105                 110

Tyr Cys Ile Asp Leu Gly Gly Gly Leu Ile Tyr Leu Glu Asn Leu
            115                 120                 125

Pro His Val Gly Val Ala Asn Arg Ser Glu Pro Asp Lys Val Asn
        130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                165                 170                 175

Asp Asp Pro Ser Gln Pro Val Ala Ser Asp Pro Tyr Gly Asp Val Phe
            180                 185                 190

Leu Ile Ile Asp Gly Trp Pro Gly Phe Val Gly Glu Phe Pro Asp Leu
        195                 200                 205

Glu Gly Gln Val Gln Asp Leu Ala Ala Gln Gly Leu Gly Phe Gly Val
    210                 215                 220

His Val Ile Ile Ser Thr Pro Arg Trp Thr Glu Leu Lys Ser Arg Val
225                 230                 235                 240

Arg Asp Tyr Leu Gly Thr Lys Ile Glu Phe Arg Leu Gly Asp Val Asn
                245                 250                 255
```

```
Glu Thr Gln Ile Asp Arg Ile Thr Arg Glu Ile Pro Ala Asn Arg Pro
            260                 265                 270

Gly Arg Ala Val Ser Met Glu Lys His His Leu Met Ile Gly Val Pro
        275                 280                 285

Arg Phe Asp Gly Val His Ser Ala Asp Asn Leu Val Glu Ala Ile Thr
    290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
                325                 330                 335

Pro Pro Gly Pro Glu Ser Asp Tyr Arg Thr Arg Trp Glu Ile Pro Ile
            340                 345                 350

Gly Leu Arg Glu Thr Asp Leu Thr Pro Ala His Cys His Met His Thr
        355                 360                 365

Asn Pro His Leu Leu Ile Phe Gly Ala Ala Lys Ser Gly Lys Thr Thr
    370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
                405                 410                 415

Val Pro Asp Thr His Leu Leu Gly Ala Gly Ala Ile Asn Arg Asn Ser
            420                 425                 430

Ala Ser Leu Asp Glu Ala Ala Gln Ala Leu Ala Val Asn Leu Lys Lys
        435                 440                 445

Arg Leu Pro Pro Thr Asp Leu Thr Thr Ala Gln Leu Arg Ser Arg Ser
    450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
                485                 490                 495

Leu Leu Pro Ala Ala Ala Asp Ile Gly Leu His Ile Ile Val Thr Cys
            500                 505                 510

Gln Met Ser Gln Ala Tyr Lys Ala Thr Met Asp Lys Phe Val Gly Ala
        515                 520                 525

Ala Phe Gly Ser Gly Ala Pro Thr Met Phe Leu Ser Gly Glu Lys Gln
    530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
                565                 570                 575

Ile Glu Pro Pro Glu Glu Val Phe Ala Ala Pro Pro Ser Ala Gly
            580                 585                 590

<210> SEQ ID NO 73
<211> LENGTH: 15
<212> TYPE: PRT
<213> ORGANISM: Mycobacterium tuberculosis

<400> SEQUENCE: 73

Asp Pro Val Asp Asp Ala Phe Ile Ala Lys Leu Asn Thr Ala Gly
  1               5                  10                  15

<210> SEQ ID NO 74
<211> LENGTH: 14
<212> TYPE: PRT
<213> ORGANISM: Mycobacterium tuberculosis
```

```
<220> FEATURE:
<221> NAME/KEY: UNSURE
<222> LOCATION: (14)
<223> OTHER INFORMATION: Xaa is unknown

<400> SEQUENCE: 74

Asp Pro Val Asp Ala Ile Ile Asn Leu Asp Asn Tyr Gly Xaa
 1               5                  10

<210> SEQ ID NO 75
<211> LENGTH: 15
<212> TYPE: PRT
<213> ORGANISM: Mycobacterium tuberculosis
<220> FEATURE:
<221> NAME/KEY: UNSURE
<222> LOCATION: (5)
<223> OTHER INFORMATION: Xaa is unknown

<400> SEQUENCE: 75

Ala Glu Met Lys Xaa Phe Lys Asn Ala Ile Val Gln Glu Ile Asp
 1               5                  10                  15

<210> SEQ ID NO 76
<211> LENGTH: 14
<212> TYPE: PRT
<213> ORGANISM: Mycobacterium tuberculosis
<220> FEATURE:
<221> NAME/KEY: VARIANT
<222> LOCATION: (3)
<223> OTHER INFORMATION: Ala is Ala or Gln
<221> NAME/KEY: VARIANT
<222> LOCATION: (7)
<223> OTHER INFORMATION: Thr is Gly or Thr
<221> NAME/KEY: UNSURE
<222> LOCATION: (11)
<223> OTHER INFORMATION: Xaa is unknown

<400> SEQUENCE: 76

Val Ile Ala Gly Met Val Thr His Ile His Xaa Val Ala Gly
 1               5                  10

<210> SEQ ID NO 77
<211> LENGTH: 15
<212> TYPE: PRT
<213> ORGANISM: Mycobacterium tuberculosis

<400> SEQUENCE: 77

Thr Asn Ile Val Val Leu Ile Lys Gln Val Pro Asp Thr Trp Ser
 1               5                  10                  15

<210> SEQ ID NO 78
<211> LENGTH: 15
<212> TYPE: PRT
<213> ORGANISM: Mycobacterium tuberculosis

<400> SEQUENCE: 78

Ala Ile Glu Val Ser Val Leu Arg Val Phe Thr Asp Ser Asp Gly
 1               5                  10                  15

<210> SEQ ID NO 79
<211> LENGTH: 15
<212> TYPE: PRT
<213> ORGANISM: Mycobacterium tuberculosis

<400> SEQUENCE: 79

Ala Lys Leu Ser Thr Asp Glu Leu Leu Asp Ala Phe Lys Glu Met
 1               5                  10                  15
```

```
<210> SEQ ID NO 80
<211> LENGTH: 15
<212> TYPE: PRT
<213> ORGANISM: Mycobacterium tuberculosis
<220> FEATURE:
<221> NAME/KEY: VARIANT
<222> LOCATION: (4)
<223> OTHER INFORMATION: Asp is Asp or Glu

<400> SEQUENCE: 80

Asp Pro Ala Asp Ala Pro Asp Val Pro Thr Ala Ala Gln Leu Thr
 1               5                  10                  15

<210> SEQ ID NO 81
<211> LENGTH: 50
<212> TYPE: PRT
<213> ORGANISM: Mycobacterium tuberculosis

<400> SEQUENCE: 81

Ala Glu Asp Val Arg Ala Glu Ile Val Ala Ser Val Leu Glu Val Val
 1               5                  10                  15

Val Asn Glu Gly Asp Gln Ile Asp Lys Gly Asp Val Val Leu Leu
            20                  25                  30

Glu Ser Met Tyr Met Glu Ile Pro Val Leu Ala Glu Ala Ala Gly Thr
        35                  40                  45

Val Ser
    50

<210> SEQ ID NO 82
<211> LENGTH: 15
<212> TYPE: PRT
<213> ORGANISM: Mycobacterium tuberculosis

<400> SEQUENCE: 82

Thr Thr Ser Pro Asp Pro Tyr Ala Ala Leu Pro Lys Leu Pro Ser
 1               5                  10                  15

<210> SEQ ID NO 83
<211> LENGTH: 15
<212> TYPE: PRT
<213> ORGANISM: Mycobacterium tuberculosis

<400> SEQUENCE: 83

Thr Glu Tyr Glu Gly Pro Lys Thr Lys Phe His Ala Leu Met Gln
 1               5                  10                  15

<210> SEQ ID NO 84
<211> LENGTH: 15
<212> TYPE: PRT
<213> ORGANISM: Mycobacterium tuberculosis

<400> SEQUENCE: 84

Thr Thr Ile Val Ala Leu Lys Tyr Pro Gly Gly Val Val Met Ala
 1               5                  10                  15

<210> SEQ ID NO 85
<211> LENGTH: 15
<212> TYPE: PRT
<213> ORGANISM: Mycobacterium tuberculosis
<220> FEATURE:
<221> NAME/KEY: UNSURE
<222> LOCATION: (10)
<223> OTHER INFORMATION: Xaa is unknown
<221> NAME/KEY: UNSURE
<222> LOCATION: (15)
<223> OTHER INFORMATION: Xaa is unknown
```

<400> SEQUENCE: 85

Ser Phe Pro Tyr Phe Ile Ser Pro Glu Xaa Ala Met Arg Glu Xaa
 1               5                  10                  15

<210> SEQ ID NO 86
<211> LENGTH: 15
<212> TYPE: PRT
<213> ORGANISM: Mycobacterium tuberculosis

<400> SEQUENCE: 86

Thr His Tyr Asp Val Val Leu Gly Ala Gly Pro Gly Gly Tyr
 1               5                  10                  15

<210> SEQ ID NO 87
<211> LENGTH: 450
<212> TYPE: DNA
<213> ORGANISM: Mycobacterium tuberculosis

<400> SEQUENCE: 87
agcccggtaa tcgagttcgg gcaatgctga ccatcgggtt tgtttccggc tataaccgaa      60
cggtttgtgt acgggataca aatacaggga gggaagaagt aggcaaatgg aaaaaatgtc    120
acatgatccg atcgctgccg acattggcac gcaagtgagc gacaacgctc tgcacggcgt    180
gacggccggc tcgacggcgc tgacgtcggt gaccgggctg gttcccgcgg gggccgatga    240
ggtctccgcc caagcggcga cggcgttcac atcggagggc atccaattgc tggcttccaa    300
tgcatcggcc caagaccagc tccaccgtgc gggcgaagcg gtccaggacg tcgcccgcac    360
ctattcgcaa atcgacgacg gcgccgccgg cgtcttcgcc taataggccc ccaacacatc    420
ggagggagtg atcaccatgc tgtggcacgc                                     450

<210> SEQ ID NO 88
<211> LENGTH: 98
<212> TYPE: PRT
<213> ORGANISM: Mycobacterium tuberculosis

<400> SEQUENCE: 88

Met Glu Lys Met Ser His Asp Pro Ile Ala Ala Asp Ile Gly Thr Gln
 1               5                  10                  15

Val Ser Asp Asn Ala Leu His Gly Val Thr Ala Gly Ser Thr Ala Leu
            20                  25                  30

Thr Ser Val Thr Gly Leu Val Pro Ala Gly Ala Asp Glu Val Ser Ala
        35                  40                  45

Gln Ala Ala Thr Ala Phe Thr Ser Glu Gly Ile Gln Leu Leu Ala Ser
    50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala

<210> SEQ ID NO 89
<211> LENGTH: 460
<212> TYPE: DNA
<213> ORGANISM: Mycobacterium tuberculosis

<400> SEQUENCE: 89
gcaaccggct tttcgatcag ctgagacatc agcggcgtgc gggtcaacga cccacctgcg      60
ccaggtagcg actccgcgcg cagcaggccc gcgcccgcgc tggggcctga tccaccagcc    120

| | |
|---|---|
| agcggatggt tcgacagcgg actggtgccg agcaggccca tctgcgcggc ttcctcgtcg | 180 |
| gctgggttgc cgccgccggt gccgcccacc tggctgaaca cgacgtcac ctgctgcagc | 240 |
| ggctgggtca gctgctgcat cgggccgctc atctcaccca gttggccgag ggtctgggta | 300 |
| gccgccggcg gcaactggcc aaccggtgtt gagctgccag gggagggcat tccgaagatc | 360 |
| gggttcgtcg tgctctggct cgcgccggga tcaaggatcg acgccatcgg ctcgagcttc | 420 |
| tcgaaaagcg tgttaaccgc ggtctcggcc tggtagacct | 460 |

<210> SEQ ID NO 90
<211> LENGTH: 139
<212> TYPE: PRT
<213> ORGANISM: Mycobacterium tuberculosis

<400> SEQUENCE: 90

Met Arg Val Asn Asp Pro Pro Ala Pro Gly Ser Asp Ser Ala Arg Ser
 1               5                  10                  15

Arg Pro Ala Pro Ala Leu Gly Pro Asp Pro Pro Ala Ser Gly Trp Phe
            20                  25                  30

Asp Ser Gly Leu Val Pro Ser Arg Pro Ile Cys Ala Ala Ser Ser Ser
        35                  40                  45

Ala Gly Leu Pro Pro Pro Val Pro Pro Thr Trp Leu Asn Asn Asp Val
    50                  55                  60

Thr Cys Cys Ser Gly Trp Val Ser Cys Cys Ile Gly Pro Leu Ile Ser
65                  70                  75                  80

Pro Ser Trp Pro Arg Val Trp Val Ala Gly Gly Asn Trp Pro Thr
                85                  90                  95

Gly Val Glu Leu Pro Gly Glu Gly Ile Pro Lys Ile Gly Phe Val Val
            100                 105                 110

Leu Trp Leu Ala Pro Gly Ser Arg Ile Asp Ala Ile Gly Ser Ser Phe
        115                 120                 125

Ser Lys Ser Val Leu Thr Ala Val Ser Ala Trp
    130                 135

<210> SEQ ID NO 91
<211> LENGTH: 1200
<212> TYPE: DNA
<213> ORGANISM: Mycobacterium tuberculosis

<400> SEQUENCE: 91

| | |
|---|---|
| taataggccc ccaacacatc ggagggagtg atcaccatgc tgtggcacgc aatgccaccg | 60 |
| gagctaaata ccgcacggct gatggccggc gcgggtccgg ctccaatgct tgcggcggcc | 120 |
| gcggatggc agacgctttc ggcggctctg acgctcagg ccgtcgagtt gaccgcgcgc | 180 |
| ctgaactctc tgggagaagc ctggactgga ggtggcagcg acaaggcgct tgcggctgca | 240 |
| acgccgatgg tggtctggct acaaaccgcg tcaacacagg ccaagaccg tgcgatgcag | 300 |
| gcgacggcgc aagccgcggc atacacccag gccatggcca cgacgccgtc gctgccggag | 360 |
| atcgccgcca accacatcac ccaggccgtc cttacggcca ccaacttctt cggtatcaac | 420 |
| acgatcccga tcgcgttgac cgagatggat tatttcatcc gtatgtggaa ccaggcagcc | 480 |
| ctggcaatgg aggtctacca ggccgagacc gcggttaaca cgcttttcga aagctcgag | 540 |
| ccgatggcgt cgatccttga tcccggcgcg agccagagca cgacgaaccc gatcttcgga | 600 |
| atgccctccc ctggcagctc aacaccggtt ggcagttgc cgccggcggc tacccagacc | 660 |
| ctcggccaac tgggtgagat gagcggcccg atgcagcagc tgacccagcc gctgcagcag | 720 |

```
gtgacgtcgt tgttcagcca ggtgggcggc accggcggcg gcaacccagc cgacgaggaa      780
gccgcgcaga tgggcctgct cggcaccagt ccgctgtcga accatccgct ggctggtgga      840
tcaggcccca gcgcgggcgc gggcctgctg cgcgcggagt cgctacctgg cgcaggtggg      900
tcgttgaccc gcacgccgct gatgtctcag ctgatcgaaa agccggttgc ccctcggtg       960
atgccggcgg ctgctgccgg atcgtcggcg acgggtggcg ccgctccggt gggtgcggga     1020
gcgatgggcc agggtgcgca atccggcggc tccaccaggc cgggtctggt cgcgccggca     1080
ccgctcgcgc aggagcgtga agaagacgac gaggacgact gggacgaaga ggacgactgg     1140
tgagctcccg taatgacaac agacttcccg gccacccggg ccggaagact tgccaacatt     1200
```

<210> SEQ ID NO 92
<211> LENGTH: 371
<212> TYPE: PRT
<213> ORGANISM: Mycobacterium tuberculosis

<400> SEQUENCE: 92

```
Met Ile Thr Met Leu Trp His Ala Met Pro Glu Leu Asn Thr Ala
 1               5                  10                  15

Arg Leu Met Ala Gly Ala Gly Pro Ala Pro Met Leu Ala Ala Ala
                20                  25                  30

Gly Trp Gln Thr Leu Ser Ala Ala Leu Asp Ala Gln Ala Val Glu Leu
                35                  40                  45

Thr Ala Arg Leu Asn Ser Leu Gly Glu Ala Trp Thr Gly Gly Ser
     50                  55                  60

Asp Lys Ala Leu Ala Ala Ala Thr Pro Met Val Val Trp Leu Gln Thr
 65                  70                  75                  80

Ala Ser Thr Gln Ala Lys Thr Arg Ala Met Gln Ala Thr Ala Gln Ala
                85                  90                  95

Ala Ala Tyr Thr Gln Ala Met Ala Thr Thr Pro Ser Leu Pro Glu Ile
                100                 105                 110

Ala Ala Asn His Ile Thr Gln Ala Val Leu Thr Ala Thr Asn Phe Phe
                115                 120                 125

Gly Ile Asn Thr Ile Pro Ile Ala Leu Thr Glu Met Asp Tyr Phe Ile
        130                 135                 140

Arg Met Trp Asn Gln Ala Ala Leu Ala Met Glu Val Tyr Gln Ala Glu
145                 150                 155                 160

Thr Ala Val Asn Thr Leu Phe Glu Lys Leu Glu Pro Met Ala Ser Ile
                165                 170                 175

Leu Asp Pro Gly Ala Ser Gln Ser Thr Thr Asn Pro Ile Phe Gly Met
                180                 185                 190

Pro Ser Pro Gly Ser Ser Thr Pro Val Gly Gln Leu Pro Pro Ala Ala
                195                 200                 205

Thr Gln Thr Leu Gly Gln Leu Gly Glu Met Ser Gly Pro Met Gln Gln
        210                 215                 220

Leu Thr Gln Pro Leu Gln Val Thr Ser Leu Phe Ser Gln Val Gly
225                 230                 235                 240

Gly Thr Gly Gly Gly Asn Pro Ala Asp Glu Glu Ala Ala Gln Met Gly
                245                 250                 255

Leu Leu Gly Thr Ser Pro Leu Ser Asn His Pro Leu Ala Gly Gly Ser
                260                 265                 270

Gly Pro Ser Ala Gly Ala Gly Leu Leu Arg Ala Glu Ser Leu Pro Gly
        275                 280                 285

Ala Gly Gly Ser Leu Thr Arg Thr Pro Leu Met Ser Gln Leu Ile Glu
        290                 295                 300
```

```
Lys Pro Val Ala Pro Ser Val Met Pro Ala Ala Ala Gly Ser Ser
305                 310                 315                 320

Ala Thr Gly Gly Ala Ala Pro Val Gly Ala Gly Ala Met Gly Gln Gly
            325                 330                 335

Ala Gln Ser Gly Gly Ser Thr Arg Pro Gly Leu Val Ala Pro Ala Pro
        340                 345                 350

Leu Ala Gln Glu Arg Glu Glu Asp Glu Asp Asp Trp Asp Glu Glu
    355                 360                 365

Asp Asp Trp
    370

<210> SEQ ID NO 93
<211> LENGTH: 1000
<212> TYPE: DNA
<213> ORGANISM: Mycobacterium tuberculosis

<400> SEQUENCE: 93
gacgcgacac agaaatcctt aaggccggcg gccaagggc  cgaaggtgaa gaaggtgaag      60
ccccagaaac cgaaggccac gaagccgccc aaagtggtgt cgcagcgcgg ctggcgacat     120
tgggtgcatg cgttgacgcg aatcaacctg gcctgtcac  ccgacgagaa gtacgagctg     180
gacctgcacg ctcgagtccg ccgcaatccc cgcgggtcgt atcagatcgc cgtcgtcggt     240
ctcaaaggtg gggctggcaa aaccacgctg acagcagcgt tggggtcgac gttggctcag     300
gtgcgggccg accggatcct ggctctagac gcggatccag gcgccggaaa cctcgccgat     360
cgggtagggc gacaatcggg cgcgaccatc gctgatgtgc ttgcagaaaa agagctgtcg     420
cactacaacg acatccgcgc acacactagc gtcaatgcgg tcaatctgga agtgctgccg     480
gcaccggaat acagctcggc gcagcgcgcg ctcagcgacg ccgactggca tttcatcgcc     540
gatcctgcgt cgaggtttta caacctcgtc ttggctgatt gtggggccgg cttcttcgac     600
ccgctgaccc gcggcgtgct gtccacggtg tccggtgtcg tggtcgtggc aagtgtctca     660
atcgacggcg cacaacaggc gtcggtcgcg ttggactggt tgcgcaacaa cggttaccaa     720
gatttggcga gccgcgcatg cgtggtcatc aatcacatca tgcccgggaga acccaatgtc     780 gcagttaaag acctggtgcg gcatttcgaa cagcaagttc aacccggccg ggtcgtggtc     840
atgccgtggg acaggcacat tgcggccgga accgagattt cactcgactt gctcgaccct     900
atctacaagc gcaaggtcct cgaattggcc gcagcgctat ccgacgattt cgagagggct     960
ggacgtcgtt gagcgcacct gctgttgctg ctggtcctac                          1000

<210> SEQ ID NO 94
<211> LENGTH: 308
<212> TYPE: PRT
<213> ORGANISM: Mycobacterium tuberculosis

<400> SEQUENCE: 94

Met Lys Lys Val Lys Pro Gln Lys Pro Lys Ala Thr Lys Pro Pro Lys
1               5                   10                  15

Val Val Ser Gln Arg Gly Trp Arg His Trp Val His Ala Leu Thr Arg
            20                  25                  30

Ile Asn Leu Gly Leu Ser Pro Asp Glu Lys Tyr Glu Leu Asp Leu His
        35                  40                  45

Ala Arg Val Arg Arg Asn Pro Arg Gly Ser Tyr Gln Ile Ala Val Val
    50                  55                  60

Gly Leu Lys Gly Gly Ala Gly Lys Thr Thr Leu Thr Ala Ala Leu Gly
65                  70                  75                  80
```

```
Ser Thr Leu Ala Gln Val Arg Ala Asp Arg Ile Leu Ala Leu Asp Ala
                85                  90                  95

Asp Pro Gly Ala Gly Asn Leu Ala Asp Arg Val Gly Arg Gln Ser Gly
            100                 105                 110

Ala Thr Ile Ala Asp Val Leu Ala Glu Lys Glu Leu Ser His Tyr Asn
        115                 120                 125

Asp Ile Arg Ala His Thr Ser Val Asn Ala Val Asn Leu Glu Val Leu
    130                 135                 140

Pro Ala Pro Glu Tyr Ser Ser Ala Gln Arg Ala Leu Ser Asp Ala Asp
145                 150                 155                 160

Trp His Phe Ile Ala Asp Pro Ala Ser Arg Phe Tyr Asn Leu Val Leu
                165                 170                 175

Ala Asp Cys Gly Ala Gly Phe Phe Asp Pro Leu Thr Arg Gly Val Leu
            180                 185                 190

Ser Thr Val Ser Gly Val Val Val Ala Ser Val Ser Ile Asp Gly
        195                 200                 205

Ala Gln Gln Ala Ser Val Ala Leu Asp Trp Leu Arg Asn Asn Gly Tyr
    210                 215                 220

Gln Asp Leu Ala Ser Arg Ala Cys Val Val Ile Asn His Ile Met Pro
225                 230                 235                 240

Gly Glu Pro Asn Val Ala Lys Asp Leu Val Arg His Phe Glu Gln
                245                 250                 255

Gln Val Gln Pro Gly Arg Val Val Met Pro Trp Asp Arg His Ile
            260                 265                 270

Ala Ala Gly Thr Glu Ile Ser Leu Asp Leu Leu Asp Pro Ile Tyr Lys
        275                 280                 285

Arg Lys Val Leu Glu Leu Ala Ala Ala Leu Ser Asp Asp Phe Glu Arg
    290                 295                 300

Ala Gly Arg Arg
305

<210> SEQ ID NO 95
<211> LENGTH: 34
<212> TYPE: DNA
<213> ORGANISM: Mycobacterium tuberculosis

<400> SEQUENCE: 95
aagagtagat ctatgatggc cgaggatgtt cgcg                                 34

<210> SEQ ID NO 96
<211> LENGTH: 27
<212> TYPE: DNA
<213> ORGANISM: Mycobacterium tuberculosis

<400> SEQUENCE: 96
cggcgacgac ggatcctacc gcgtcgg                                         27

<210> SEQ ID NO 97
<211> LENGTH: 28
<212> TYPE: DNA
<213> ORGANISM: Mycobacterium tuberculosis

<400> SEQUENCE: 97
ccttgggaga tctttggacc ccggttgc                                        28
```

```
<210> SEQ ID NO 98
<211> LENGTH: 25
<212> TYPE: DNA
<213> ORGANISM: Mycobacterium tuberculosis

<400> SEQUENCE: 98
gacgagatct tatgggctta ctgac                                          25

<210> SEQ ID NO 99
<211> LENGTH: 33
<212> TYPE: DNA
<213> ORGANISM: Mycobacterium tuberculosis

<400> SEQUENCE: 99 cccccagat ctgcaccacc ggcatcggcg ggc                                  33

<210> SEQ ID NO 100
<211> LENGTH: 24
<212> TYPE: DNA
<213> ORGANISM: Mycobacterium tuberculosis

<400> SEQUENCE: 100
gcggcggatc cgttgcttag ccgg                                           24

<210> SEQ ID NO 101
<211> LENGTH: 32
<212> TYPE: DNA
<213> ORGANISM: Mycobacterium tuberculosis

<400> SEQUENCE: 101
ccggctgaga tctatgacag aatacgaagg gc                                  32

<210> SEQ ID NO 102
<211> LENGTH: 24
<212> TYPE: DNA
<213> ORGANISM: Mycobacterium tuberculosis

<400> SEQUENCE: 102
ccccgccagg gaactagagg cggc                                           24

<210> SEQ ID NO 103
<211> LENGTH: 38
<212> TYPE: DNA
<213> ORGANISM: Mycobacterium tuberculosis

<400> SEQUENCE: 103
ctgccgagat ctaccaccat tgtcgcgctg aaataccc                            38

<210> SEQ ID NO 104
<211> LENGTH: 25
<212> TYPE: DNA
<213> ORGANISM: Mycobacterium tuberculosis

<400> SEQUENCE: 104
cgccatggcc ttacgcgcca actcg                                          25

<210> SEQ ID NO 105
<211> LENGTH: 32
<212> TYPE: DNA
<213> ORGANISM: Mycobacterium tuberculosis

<400> SEQUENCE: 105
ggcggagatc tgtgagtttt ccgtatttca tc                                  32
```

```
<210> SEQ ID NO 106
<211> LENGTH: 25
<212> TYPE: DNA
<213> ORGANISM: Mycobacterium tuberculosis

<400> SEQUENCE: 106
cgcgtcgagc catggttagg cgcag                                              25

<210> SEQ ID NO 107
<211> LENGTH: 32
<212> TYPE: DNA
<213> ORGANISM: Mycobacterium tuberculosis

<400> SEQUENCE: 107
gaggaagatc tatgacaact tcacccgacc cg                                      32

<210> SEQ ID NO 108
<211> LENGTH: 28
<212> TYPE: DNA
<213> ORGANISM: Mycobacterium tuberculosis

<400> SEQUENCE: 108
catgaagcca tggcccgcag gctgcatg                                           28

<210> SEQ ID NO 109
<211> LENGTH: 33
<212> TYPE: DNA
<213> ORGANISM: Mycobacterium tuberculosis

<400> SEQUENCE: 109
ggccgagatc tgtgacccac tatgacgtcg tcg                                     33

<210> SEQ ID NO 110
<211> LENGTH: 36
<212> TYPE: DNA
<213> ORGANISM: Mycobacterium tuberculosis

<400> SEQUENCE: 110
ggcgcccatg gtcagaaatt gatcatgtgg ccaacc                                  36

<210> SEQ ID NO 111
<211> LENGTH: 33
<212> TYPE: DNA
<213> ORGANISM: Mycobacterium tuberculosis

<400> SEQUENCE: 111
ccgggagatc tatggcaaag ctctccaccg acg                                     33

<210> SEQ ID NO 112
<211> LENGTH: 32
<212> TYPE: DNA
<213> ORGANISM: Mycobacterium tuberculosis

<400> SEQUENCE: 112
cgctgggcag agctacttga cggtgacggt gg                                      32

<210> SEQ ID NO 113
<211> LENGTH: 36
<212> TYPE: DNA
<213> ORGANISM: Mycobacterium tuberculosis

<400> SEQUENCE: 113
ggcccagatc tatggccatt gaggtttcgg tgttgc                                  36
```

```
<210> SEQ ID NO 114
<211> LENGTH: 26
<212> TYPE: DNA
<213> ORGANISM: Mycobacterium tuberculosis

<400> SEQUENCE: 114
cgccgtgttg catggcagcg ctgagc                                        26

<210> SEQ ID NO 115
<211> LENGTH: 24
<212> TYPE: DNA
<213> ORGANISM: Mycobacterium tuberculosis

<400> SEQUENCE: 115
ggacgttcaa gcgacacatc gccg                                          24

<210> SEQ ID NO 116
<211> LENGTH: 24
<212> TYPE: DNA
<213> ORGANISM: Mycobacterium tuberculosis

<400> SEQUENCE: 116
cagcacgaac gcgccgtcga tggc                                          24

<210> SEQ ID NO 117
<211> LENGTH: 26
<212> TYPE: DNA
<213> ORGANISM: Mycobacterium tuberculosis

<400> SEQUENCE: 117
acagatctgt gacggacatg aacccg                                        26

<210> SEQ ID NO 118
<211> LENGTH: 28
<212> TYPE: DNA
<213> ORGANISM: Mycobacterium tuberculosis

<400> SEQUENCE: 118
ttttccatgg tcacgggccc ccggtact                                      28

<210> SEQ ID NO 119
<211> LENGTH: 26
<212> TYPE: DNA
<213> ORGANISM: Mycobacterium tuberculosis

<400> SEQUENCE: 119
acagatctgt gcccatggca cagata                                        26

<210> SEQ ID NO 120
<211> LENGTH: 27
<212> TYPE: DNA
<213> ORGANISM: Mycobacterium tuberculosis

<400> SEQUENCE: 120
tttaagcttc taggcgccca gcgcggc                                       27

<210> SEQ ID NO 121
<211> LENGTH: 26
<212> TYPE: DNA
<213> ORGANISM: Mycobacterium tuberculosis

<400> SEQUENCE: 121
acagatctgc gcatgcggat ccgtgt                                        26
```

```
<210> SEQ ID NO 122
<211> LENGTH: 28
<212> TYPE: DNA
<213> ORGANISM: Mycobacterium tuberculosis

<400> SEQUENCE: 122
ttttccatgg tcatccggcg tgatcgag                                    28

<210> SEQ ID NO 123
<211> LENGTH: 26
<212> TYPE: DNA
<213> ORGANISM: Mycobacterium tuberculosis

<400> SEQUENCE: 123
acagatctgt aatggcagac tgtgat                                      26

<210> SEQ ID NO 124
<211> LENGTH: 28
<212> TYPE: DNA
<213> ORGANISM: Mycobacterium tuberculosis

<400> SEQUENCE: 124
ttttccatgg tcaggagatg gtgatcga                                    28

<210> SEQ ID NO 125
<211> LENGTH: 26
<212> TYPE: DNA
<213> ORGANISM: Mycobacterium tuberculosis

<400> SEQUENCE: 125
acagatctgc cggctacccc ggtgcc                                      26

<210> SEQ ID NO 126
<211> LENGTH: 28
<212> TYPE: DNA
<213> ORGANISM: Mycobacterium tuberculosis

<400> SEQUENCE: 126
ttttccatgg ctattgcagc tttccggc                                    28

<210> SEQ ID NO 127
<211> LENGTH: 50
<212> TYPE: PRT
<213> ORGANISM: Mycobacterium tuberculosis

<400> SEQUENCE: 127

Ala Glu Asp Val Arg Ala Glu Ile Val Ala Ser Val Leu Glu Val Val
 1               5                  10                  15

Val Asn Glu Gly Asp Gln Ile Asp Lys Gly Asp Val Val Leu Leu
            20                  25                  30

Glu Ser Met Tyr Met Glu Ile Pro Val Leu Ala Glu Ala Ala Gly Thr
        35                  40                  45

Val Ser
    50

<210> SEQ ID NO 128
<211> LENGTH: 49
<212> TYPE: PRT
<213> ORGANISM: Mycobacterium tuberculosis
```

<400> SEQUENCE: 128

Ala Glu Asp Val Arg Ala Glu Ile Val Ala Ser Val Leu Glu Val Val
1               5                   10                  15

Val Asn Glu Gly Asp Gln Ile Asp Lys Gly Asp Val Val Leu Leu
            20                  25                  30

Glu Ser Met Met Glu Ile Pro Val Leu Ala Glu Ala Ala Gly Thr Val
        35                  40                  45

Ser

<210> SEQ ID NO 129
<211> LENGTH: 50
<212> TYPE: PRT
<213> ORGANISM: Mycobacterium tuberculosis

<400> SEQUENCE: 129

Ala Glu Asp Val Arg Ala Glu Ile Val Ala Ser Val Leu Glu Val Val
1               5                   10                  15

Val Asn Glu Gly Asp Gln Ile Asp Lys Gly Asp Val Val Leu Leu
            20                  25                  30

Glu Ser Met Lys Met Glu Ile Pro Val Leu Ala Glu Ala Ala Gly Thr
        35                  40                  45

Val Ser
    50

<210> SEQ ID NO 130
<211> LENGTH: 33
<212> TYPE: DNA
<213> ORGANISM: Mycobacterium tuberculosis

<400> SEQUENCE: 130
ccgggagatc tatggcaaag ctctccaccg acg                             33

<210> SEQ ID NO 131
<211> LENGTH: 32
<212> TYPE: DNA
<213> ORGANISM: Mycobacterium tuberculosis

<400> SEQUENCE: 131
cgctgggcag agctacttga cggtgacggt gg                              32

<210> SEQ ID NO 132
<211> LENGTH: 36
<212> TYPE: DNA
<213> ORGANISM: Mycobacterium tuberculosis

<400> SEQUENCE: 132
ggcgccggca agcttgccat gacagagcag cagtgg                          36

<210> SEQ ID NO 133
<211> LENGTH: 26
<212> TYPE: DNA
<213> ORGANISM: Mycobacterium tuberculosis

<400> SEQUENCE: 133
cgaactcgcc ggatcccgtg tttcgc                                     26

<210> SEQ ID NO 134
<211> LENGTH: 32
<212> TYPE: DNA
<213> ORGANISM: Mycobacterium tuberculosis

<400> SEQUENCE: 134
ggcaaccgcg agatctttct cccggccggg gc                                    32

<210> SEQ ID NO 135
<211> LENGTH: 27
<212> TYPE: DNA
<213> ORGANISM: Mycobacterium tuberculosis

<400> SEQUENCE: 135
ggcaagcttg ccggcgccta acgaact                                          27

<210> SEQ ID NO 136
<211> LENGTH: 30
<212> TYPE: DNA
<213> ORGANISM: Mycobacterium tuberculosis

<400> SEQUENCE: 136
ggacccagat ctatgacaga gcagcagtgg                                       30

<210> SEQ ID NO 137
<211> LENGTH: 47
<212> TYPE: DNA
<213> ORGANISM: Mycobacterium tuberculosis

<400> SEQUENCE: 137
ccggcagccc cggccgggag aaaagctttg cgaacatccc agtgacg                    47

<210> SEQ ID NO 138
<211> LENGTH: 44
<212> TYPE: DNA
<213> ORGANISM: Mycobacterium tuberculosis

<400> SEQUENCE: 138
gttcgcaaag cttttctccc ggccggggct gccggtcgag tacc                       44

<210> SEQ ID NO 139
<211> LENGTH: 20
<212> TYPE: DNA
<213> ORGANISM: Mycobacterium tuberculosis

<400> SEQUENCE: 139
ccttcggtgg atcccgtcag                                                  20

<210> SEQ ID NO 140
<211> LENGTH: 450
<212> TYPE: DNA
<213> ORGANISM: Mycobacterium tuberculosis

<400> SEQUENCE: 140
tggcgctgtc accgaggaac ctgtcaatgt cgtcgagcag tactgaaccg ttccgagaaa      60
ggccagcatg aacgtcaccg tatccattcc gaccatcctg cggccccaca ccggcggcca     120
gaagagtgtc tcggccagcg gcgataccct gggtgccgtc atcagcgacc tggaggccaa     180
ctattcgggc atttccgagc gcctgatgga cccgtcttcc ccaggtaagt tgcaccgctt     240
cgtgaacatc tacgtcaacg acgaggacgt gcggttctcc ggcggcttgg ccaccgcgat     300
cgctgacggt gactcggtca ccatcctccc cgccgtggcc ggtgggtgag cggagcacat     360
gacacgatac gactcgctgt tgcaggcctt gggcaacacg ccgctggttg gcctgcagcg     420
attgtcgcca cgctgggatg acgggcgaga                                     450

```
<210> SEQ ID NO 141
<211> LENGTH: 93
<212> TYPE: PRT
<213> ORGANISM: Mycobacterium tuberculosis

<400> SEQUENCE: 141

Met Asn Val Thr Val Ser Ile Pro Thr Ile Leu Arg Pro His Thr Gly
  1               5                  10                  15

Gly Gln Lys Ser Val Ser Ala Ser Gly Asp Thr Leu Gly Ala Val Ile
             20                  25                  30

Ser Asp Leu Glu Ala Asn Tyr Ser Gly Ile Ser Glu Arg Leu Met Asp
         35                  40                  45

Pro Ser Pro Gly Lys Leu His Arg Phe Val Asn Ile Tyr Val Asn
     50                  55                  60

Asp Glu Asp Val Arg Phe Ser Gly Gly Leu Ala Thr Ala Ile Ala Asp
 65                  70                  75                  80

Gly Asp Ser Val Thr Ile Leu Pro Ala Val Ala Gly Gly
                 85                  90

<210> SEQ ID NO 142
<211> LENGTH: 480
<212> TYPE: DNA
<213> ORGANISM: Mycobacterium tuberculosis

<400> SEQUENCE: 142
ggtgttcccg cggccggcta tgacaacagt caatgtgcat gacaagttac aggtattagg     60
tccaggttca acaaggagac aggcaacatg gcaacacgtt ttatgacgga tccgcacgcg    120
atgcgggaca tggcgggccg ttttgaggtg cacgcccaga cggtggagga cgaggctcgc    180
cggatgtggg cgtccgcgca aaacatctcg ggcgcgggct ggagtggcat ggccgaggcg    240
acctcgctag acaccatggc ccagatgaat caggcgtttc gcaacatcgt gaacatgctg    300
cacggggtgc gtgacgggct ggttcgcgac gccaacaact acgagcagca agagcaggcc    360
tcccagcaga tcctcagcag ctaacgtcag ccgctgcagc acaatacttt tacaagcgaa    420
ggagaacagg ttcgatgacc atcaactatc agttcggtga tgtcgacgct catggcgcca    480

<210> SEQ ID NO 143
<211> LENGTH: 98
<212> TYPE: PRT
<213> ORGANISM: Mycobacterium tuberculosis

<400> SEQUENCE: 143

Met Ala Thr Arg Phe Met Thr Asp Pro His Ala Met Arg Asp Met Ala
  1               5                  10                  15

Gly Arg Phe Glu Val His Ala Gln Thr Val Glu Asp Glu Ala Arg Arg
             20                  25                  30

Met Trp Ala Ser Ala Gln Asn Ile Ser Gly Ala Gly Trp Ser Gly Met
         35                  40                  45

Ala Glu Ala Thr Ser Leu Asp Thr Met Ala Gln Met Asn Gln Ala Phe
     50                  55                  60

Arg Asn Ile Val Asn Met Leu His Gly Val Arg Asp Gly Leu Val Arg
 65                  70                  75                  80

Asp Ala Asn Asn Tyr Glu Gln Gln Glu Gln Ala Ser Gln Gln Ile Leu
                 85                  90                  95

Ser Ser
```

<210> SEQ ID NO 144
<211> LENGTH: 940
<212> TYPE: DNA
<213> ORGANISM: Mycobacterium tuberculosis

<400> SEQUENCE: 144

```
gccccagtcc tcgatcgcct catcgccttc accggccgcc agccgaccgc aggccacgtg      60
tccgccacct aacgaaagga tgatcatgcc aagagaagc gaatacaggc aaggcacgcc     120
gaactgggtc gaccttcaga ccaccgatca gtccgccgcc aaaaagttct acacatcgtt     180
gttcggctgg ggttacgacg acaacccggt ccccggaggc ggtggggtct attccatggc     240
cacgctgaac ggcgaagccg tggccgccat cgcaccgatg ccccggggtg caccggaggg     300
gatgccgccg atctggaaca cctatatcgc ggtggacgac gtcgatgcgg tggtggacaa     360
ggtggtgccc gggggcgggc aggtgatgat gccggccttc gacatcggcg atgccggccg     420
gatgtcgttc atcaccgatc cgaccggcgc tgccgtgggc ctatggcagg ccaatcggca     480
catcggagcg acgttggtca cgagacggg cacgctcatc tggaacgaac tgctcacgga     540
caagccggat ttggcgctag cgttctacga ggctgtggtt ggcctcaccc actcgagcat     600
ggagatagct gcgggccaga actatcgggt gctcaaggcc ggcgacgcgg aagtcggcgg     660
ctgtatggaa ccgccgatgc ccggcgtgcc gaatcattgg cacgtctact ttgcggtgga     720
tgacgccgac gccacggcgg ccaaagccgc cgcagcgggc ggccaggtca ttgcggaacc     780
ggctgacatt ccgtcggtgg gccggttcgc cgtgttgtcc gatccgcagg gcgcgatctt     840
cagtgtgttg aagcccgcac cgcagcaata gggagcatcc cgggcaggcc cgccggccgg     900
cagattcgga gaatgctaga agctgccgcc ggcgccgccg                           940
```

<210> SEQ ID NO 145
<211> LENGTH: 261
<212> TYPE: PRT
<213> ORGANISM: Mycobacterium tuberculosis

<400> SEQUENCE: 145

```
Met Pro Lys Arg Ser Glu Tyr Arg Gln Gly Thr Pro Asn Trp Val Asp
  1               5                  10                  15

Leu Gln Thr Thr Asp Gln Ser Ala Ala Lys Lys Phe Tyr Thr Ser Leu
             20                  25                  30

Phe Gly Trp Gly Tyr Asp Asp Asn Pro Val Pro Gly Gly Gly Gly Val
         35                  40                  45

Tyr Ser Met Ala Thr Leu Asn Gly Glu Ala Val Ala Ala Ile Ala Pro
     50                  55                  60

Met Pro Pro Gly Ala Pro Glu Gly Met Pro Pro Ile Trp Asn Thr Tyr
 65                  70                  75                  80

Ile Ala Val Asp Asp Val Asp Ala Val Val Asp Lys Val Val Pro Gly
                 85                  90                  95

Gly Gly Gln Val Met Met Pro Ala Phe Asp Ile Gly Asp Ala Gly Arg
            100                 105                 110

Met Ser Phe Ile Thr Asp Pro Thr Gly Ala Ala Val Gly Leu Trp Gln
        115                 120                 125

Ala Asn Arg His Ile Gly Ala Thr Leu Val Asn Glu Thr Gly Thr Leu
    130                 135                 140

Ile Trp Asn Glu Leu Leu Thr Asp Lys Pro Asp Leu Ala Leu Ala Phe
145                 150                 155                 160

Tyr Glu Ala Val Val Gly Leu Thr His Ser Ser Met Glu Ile Ala Ala
                165                 170                 175
```

```
Gly Gln Asn Tyr Arg Val Leu Lys Ala Gly Asp Ala Glu Val Gly Gly
            180                 185                 190

Cys Met Glu Pro Pro Met Pro Gly Val Pro Asn His Trp His Val Tyr
        195                 200                 205

Phe Ala Val Asp Asp Ala Asp Ala Thr Ala Ala Lys Ala Ala Ala Ala
            210                 215                 220

Gly Gly Gln Val Ile Ala Glu Pro Ala Asp Ile Pro Ser Val Gly Arg
225                 230                 235                 240

Phe Ala Val Leu Ser Asp Pro Gln Gly Ala Ile Phe Ser Val Leu Lys
                245                 250                 255

Pro Ala Pro Gln Gln
            260

<210> SEQ ID NO 146
<211> LENGTH: 280
<212> TYPE: DNA
<213> ORGANISM: Mycobacterium tuberculosis

<400> SEQUENCE: 146
ccgaaaggcg gtgcaccgca cccagaagaa aaggaaagat cgagaaatgc cacagggaac      60
tgtgaagtgg ttcaacgcgg agaaggggtt cggctttatc gccccgaag acggttccgc     120 ggatgtattt gtccactaca cggagatcca gggaacgggc ttccgcaccc ttgaagaaaa     180
ccagaaggtc gagttcgaga tcggccacag ccctaagggc cccaggcca ccggagtccg     240 ctcgctctga gttaccccccg cgagcagacg caaaaagccc                          280

<210> SEQ ID NO 147
<211> LENGTH: 67
<212> TYPE: PRT
<213> ORGANISM: Mycobacterium tuberculosis

<400> SEQUENCE: 147

Met Pro Gln Gly Thr Val Lys Trp Phe Asn Ala Glu Lys Gly Phe Gly
  1               5                  10                  15

Phe Ile Ala Pro Glu Asp Gly Ser Ala Asp Val Phe Val His Tyr Thr
             20                  25                  30

Glu Ile Gln Gly Thr Gly Phe Arg Thr Leu Glu Glu Asn Gln Lys Val
         35                  40                  45

Glu Phe Glu Ile Gly His Ser Pro Lys Gly Pro Gln Ala Thr Gly Val
     50                  55                  60

Arg Ser Leu
 65

<210> SEQ ID NO 148
<211> LENGTH: 540
<212> TYPE: DNA
<213> ORGANISM: Mycobacterium tuberculosis

<400> SEQUENCE: 148
atcgtgtcgt atcgagaacc ccggccggta tcagaacgcg ccagagcgca aacctttata      60
acttcgtgtc ccaaatgtga cgaccatgga ccaaggttcc tgagatgaac ctacggcgcc     120
atcagaccct gacgctgcga ctgctggcgg catccgcggg cattctcagc gccgcggcct     180
tcgccgcgcc agcacaggca aacccgtcg acgacgcgtt catcgccgcg ctgaacaatg     240
ccggcgtcaa ctacgcgat ccggtcgacg ccaaagcgct gggtcagtcc gtctgcccga     300
tcctggccga gcccggcggg tcgtttaaca ccgcggtagc cagcgttgtg gcgcgcgccc     360
```

-continued

```
aaggcatgtc ccaggacatg gcgcaaacct tcaccagtat cgcgatttcg atgtactgcc        420
cctcggtgat ggcagacgtc gccagcggca acctgccggc cctgccagac atgccggggc        480
tgcccgggtc ctaggcgtgc gcggctccta gccggtccct aacggatcga tcgtggatgc        540
```

<210> SEQ ID NO 149
<211> LENGTH: 129
<212> TYPE: PRT
<213> ORGANISM: Mycobacterium tuberculosis

<400> SEQUENCE: 149

Met Asn Leu Arg Arg His Gln Thr Leu Thr Leu Arg Leu Leu Ala Ala
1               5                   10                  15

Ser Ala Gly Ile Leu Ser Ala Ala Ala Phe Ala Ala Pro Ala Gln Ala
            20                  25                  30

Asn Pro Val Asp Asp Ala Phe Ile Ala Ala Leu Asn Asn Ala Gly Val
        35                  40                  45

Asn Tyr Gly Asp Pro Val Asp Ala Lys Ala Leu Gly Gln Ser Val Cys
    50                  55                  60

Pro Ile Leu Ala Glu Pro Gly Gly Ser Phe Asn Thr Ala Val Ala Ser
65                  70                  75                  80

Val Val Ala Arg Ala Gln Gly Met Ser Gln Asp Met Ala Gln Thr Phe
                85                  90                  95

Thr Ser Ile Ala Ile Ser Met Tyr Cys Pro Ser Val Met Ala Asp Val
            100                 105                 110

Ala Ser Gly Asn Leu Pro Ala Leu Pro Asp Met Pro Gly Leu Pro Gly
        115                 120                 125

Ser

<210> SEQ ID NO 150
<211> LENGTH: 400
<212> TYPE: DNA
<213> ORGANISM: Mycobacterium tuberculosis

<400> SEQUENCE: 150

```
atagtttggg gaaggtgtcc ataaatgagg ctgtcgttga ccgcattgag cgccggtgta        60
ggcgccgtgg caatgtcgtt gaccgtcggg gccggggtcg cctccgcaga tcccgtggac        120
gcggtcatta acaccacctg caattacggg caggtagtag ctgcgctcaa cgcgacggat        180 ccggggggctg ccgcacagtt caacgcctca ccggtggcgc agtcctattt gcgcaatttc        240
ctcgccgcac cgccacctca gcgcgctgcc atggccgcgc aattgcaagc tgtgccgggg        300
gcggcacagt acatcggcct tgtcgagtcg gttgccggct cctgcaacaa ctattaagcc        360
catgcgggcc ccatcccgcg acccggcatc gtcgccgggg                             400
```

<210> SEQ ID NO 151
<211> LENGTH: 110
<212> TYPE: PRT
<213> ORGANISM: Mycobacterium tuberculosis

<400> SEQUENCE: 151

Met Arg Leu Ser Leu Thr Ala Leu Ser Ala Gly Val Gly Ala Val Ala
1               5                   10                  15

Met Ser Leu Thr Val Gly Ala Gly Val Ala Ser Ala Asp Pro Val Asp
            20                  25                  30

Ala Val Ile Asn Thr Thr Cys Asn Tyr Gly Gln Val Val Ala Ala Leu
        35                  40                  45

```
Asn Ala Thr Asp Pro Gly Ala Ala Gln Phe Asn Ala Ser Pro Val
        50                  55                  60

Ala Gln Ser Tyr Leu Arg Asn Phe Leu Ala Ala Pro Pro Gln Arg
 65                  70                  75                  80

Ala Ala Met Ala Ala Gln Leu Gln Ala Val Pro Gly Ala Ala Gln Tyr
                 85                  90                  95

Ile Gly Leu Val Glu Ser Val Ala Gly Ser Cys Asn Asn Tyr
                100                 105                 110

<210> SEQ ID NO 152
<211> LENGTH: 990
<212> TYPE: DNA
<213> ORGANISM: Mycobacterium tuberculosis

<400> SEQUENCE: 152
aatagtaata tcgctgtgcg gttgcaaaac gtgtgaccga ggttccgcag tcgagcgctg        60
cgggccgcct tcgaggagga cgaaccacag tcatgacgaa catcgtggtc ctgatcaagc       120
aggtcccaga tacctggtcg gagcgcaagc tgaccgacgg cgatttcacg ctggaccgcg       180
aggccgccga cgcggtgctg gacgagatca acgagcgcgc cgtggaggaa gcgctacaga       240
ttcgggagaa agaggccgcc gacggcatcg aagggtcggt aaccgtgctg acggcgggcc       300
ccgagcgcgc caccgaggcg atccgcaagg cgctgtcgat gggtgccgac aaggccgtcc       360
acctaaagga cgacggcatg cacggctcgg acgtcatcca aaccgggtgg gctttggcgc       420
gcgcgttggg caccatcgag ggcaccgagc tggtgatcgc aggcaacgaa tcgaccgacg       480
gggtgggcgg tgcggtgccg gccatcatcg ccgagtacct gggcctgccg cagctcaccc       540
acctgcgcaa agtgtcgatc gagggcggca agatcaccgg cgagcgtgag accgatgagg       600
gcgtattcac cctcgaggcc acgctgcccg cggtgatcag cgtgaacgag aagatcaacg       660
agccgcgctt cccgtccttc aaaggcatca tggccgccaa gaagaaggaa gttaccgtgc       720
tgaccctggc cgagatcggt gtcgagagcg acgaggtggg gctggccaac gccggatcca       780
ccgtgctggc gtcgacgccc aaaccggcca agactgccgg ggagaaggtc accgacgagg       840
gtgaaggcgg caaccagatc gtgcagtacc tggttgccca gaaaatcatc taagacatac       900
gcacctccca aagacgagag cgatataacc catggctgaa gtactggtgc tcgttgagca       960
cgctgaaggc gcgttaaaga aggtcagcgc                                        990

<210> SEQ ID NO 153
<211> LENGTH: 266
<212> TYPE: PRT
<213> ORGANISM: Mycobacterium tuberculosis

<400> SEQUENCE: 153

Met Thr Asn Ile Val Val Leu Ile Lys Gln Val Pro Asp Thr Trp Ser
  1               5                  10                  15

Glu Arg Lys Leu Thr Asp Gly Asp Phe Thr Leu Asp Arg Glu Ala Ala
                 20                  25                  30

Asp Ala Val Leu Asp Glu Ile Asn Glu Arg Ala Val Glu Glu Ala Leu
             35                  40                  45

Gln Ile Arg Glu Lys Glu Ala Ala Asp Gly Ile Glu Gly Ser Val Thr
        50                  55                  60

Val Leu Thr Ala Gly Pro Glu Arg Ala Thr Glu Ala Ile Arg Lys Ala
 65                  70                  75                  80

Leu Ser Met Gly Ala Asp Lys Ala Val His Leu Lys Asp Asp Gly Met
                 85                  90                  95
```

-continued

His Gly Ser Asp Val Ile Gln Thr Gly Trp Ala Leu Ala Arg Ala Leu
            100                 105                 110

Gly Thr Ile Glu Gly Thr Glu Leu Val Ile Ala Gly Asn Glu Ser Thr
        115                 120                 125

Asp Gly Val Gly Gly Ala Val Pro Ala Ile Ile Ala Glu Tyr Leu Gly
    130                 135                 140

Leu Pro Gln Leu Thr His Leu Arg Lys Val Ser Ile Glu Gly Gly Lys
145                 150                 155                 160

Ile Thr Gly Glu Arg Glu Thr Asp Glu Gly Val Phe Thr Leu Glu Ala
                165                 170                 175

Thr Leu Pro Ala Val Ile Ser Val Asn Glu Lys Ile Asn Glu Pro Arg
            180                 185                 190

Phe Pro Ser Phe Lys Gly Ile Met Ala Ala Lys Lys Glu Val Thr
        195                 200                 205

Val Leu Thr Leu Ala Glu Ile Gly Val Glu Ser Asp Glu Val Gly Leu
    210                 215                 220

Ala Asn Ala Gly Ser Thr Val Leu Ala Ser Thr Pro Lys Pro Ala Lys
225                 230                 235                 240

Thr Ala Gly Glu Lys Val Thr Asp Glu Gly Glu Gly Gly Asn Gln Ile
                245                 250                 255

Val Gln Tyr Leu Val Ala Gln Lys Ile Ile
            260                 265

<210> SEQ ID NO 154
<211> LENGTH: 25
<212> TYPE: DNA
<213> ORGANISM: Mycobacterium tuberculosis

<400> SEQUENCE: 154
ctgagatcta tgaacctacg gcgcc                                          25

<210> SEQ ID NO 155
<211> LENGTH: 35
<212> TYPE: DNA
<213> ORGANISM: Mycobacterium tuberculosis

<400> SEQUENCE: 155
ctcccatggt accctaggac ccgggcagcc ccggc                               35

<210> SEQ ID NO 156
<211> LENGTH: 29
<212> TYPE: DNA
<213> ORGANISM: Mycobacterium tuberculosis

<400> SEQUENCE: 156
ctgagatcta tgaggctgtc gttgaccgc                                      29

<210> SEQ ID NO 157
<211> LENGTH: 30
<212> TYPE: DNA
<213> ORGANISM: Mycobacterium tuberculosis

<400> SEQUENCE: 157
ctccccgggc ttaatagttg ttgcaggagc                                     30

<210> SEQ ID NO 158
<211> LENGTH: 33
<212> TYPE: DNA
<213> ORGANISM: Mycobacterium tuberculosis

```
<400> SEQUENCE: 158
gcttagatct atgattttct gggcaaccag gta                              33

<210> SEQ ID NO 159
<211> LENGTH: 30
<212> TYPE: DNA
<213> ORGANISM: Mycobacterium tuberculosis

<400> SEQUENCE: 159
gcttccatgg gcgaggcaca ggcgtgggaa                                  30

<210> SEQ ID NO 160
<211> LENGTH: 30
<212> TYPE: DNA
<213> ORGANISM: Mycobacterium tuberculosis

<400> SEQUENCE: 160
ctgagatcta gaatgccaca gggaactgtg                                  30

<210> SEQ ID NO 161
<211> LENGTH: 30
<212> TYPE: DNA
<213> ORGANISM: Mycobacterium tuberculosis

<400> SEQUENCE: 161
tctcccgggg gtaactcaga gcgagcggac                                  30

<210> SEQ ID NO 162
<211> LENGTH: 27
<212> TYPE: DNA
<213> ORGANISM: Mycobacterium tuberculosis

<400> SEQUENCE: 162
ctgagatcta tgaacgtcac cgtatcc                                     27

<210> SEQ ID NO 163
<211> LENGTH: 27
<212> TYPE: DNA
<213> ORGANISM: Mycobacterium tuberculosis

<400> SEQUENCE: 163
tctcccgggg ctcacccacc ggccacg                                     27

<210> SEQ ID NO 164
<211> LENGTH: 30
<212> TYPE: DNA
<213> ORGANISM: Mycobacterium tuberculosis

<400> SEQUENCE: 164
ctgagatcta tggcaacacg ttttatgacg                                  30

<210> SEQ ID NO 165
<211> LENGTH: 30
<212> TYPE: DNA
<213> ORGANISM: Mycobacterium tuberculosis

<400> SEQUENCE: 165
ctccccgggt tagctgctga ggatctgcth                                  30

<210> SEQ ID NO 166
<211> LENGTH: 31
<212> TYPE: DNA
<213> ORGANISM: Mycobacterium tuberculosis
```

-continued

```
<400> SEQUENCE: 166
ctgaagatct atgcccaaga gaagcgaata c                                    31

<210> SEQ ID NO 167
<211> LENGTH: 31
<212> TYPE: DNA
<213> ORGANISM: Mycobacterium tuberculosis

<400> SEQUENCE: 167
cggcagctgc tagcattctc cgaatctgcc g                                    31

<210> SEQ ID NO 168
<211> LENGTH: 15
<212> TYPE: PRT
<213> ORGANISM: Mycobacterium tuberculosis

<400> SEQUENCE: 168

Pro Gln Gly Thr Val Lys Trp Phe Asn Ala Glu Lys Gly Phe Gly
  1               5                  10                  15

<210> SEQ ID NO 169
<211> LENGTH: 15
<212> TYPE: PRT
<213> ORGANISM: Mycobacterium tuberculosis
<220> FEATURE:
<221> NAME/KEY: UNSURE
<222> LOCATION: (15)
<223> OTHER INFORMATION: Xaa is unknown

<400> SEQUENCE: 169

Asn Val Thr Val Ser Ile Pro Thr Ile Leu Arg Pro Xaa Xaa Xaa
  1               5                  10                  15

<210> SEQ ID NO 170
<211> LENGTH: 15
<212> TYPE: PRT
<213> ORGANISM: Mycobacterium tuberculosis
<220> FEATURE:
<221> NAME/KEY: VARIANT
<222> LOCATION: (1)
<223> OTHER INFORMATION: Thr could also be Ala

<400> SEQUENCE: 170

Thr Arg Phe Met Thr Asp Pro His Ala Met Arg Asp Met Ala Gly
  1               5                  10                  15

<210> SEQ ID NO 171
<211> LENGTH: 15
<212> TYPE: PRT
<213> ORGANISM: Mycobacterium tuberculosis

<400> SEQUENCE: 171

Pro Lys Arg Ser Glu Tyr Arg Gln Gly Thr Pro Asn Trp Val Asp
  1               5                  10                  15

<210> SEQ ID NO 172
<211> LENGTH: 404
<212> TYPE: PRT
<213> ORGANISM: Mycobacterium tuberculosis

<400> SEQUENCE: 172

Met Ala Thr Val Asn Arg Ser Arg His His His His His His His
  1               5                  10                  15

Ile Glu Gly Arg Ser Phe Ser Arg Pro Gly Leu Pro Val Glu Tyr Leu
                 20                  25                  30
```

-continued

```
Gln Val Pro Ser Pro Ser Met Gly Arg Asp Ile Lys Val Gln Phe Gln
             35                  40                  45

Ser Gly Gly Asn Asn Ser Pro Ala Val Tyr Leu Leu Asp Gly Leu Arg
     50                  55                  60

Ala Gln Asp Asp Tyr Asn Gly Trp Asp Ile Asn Thr Pro Ala Phe Glu
 65                  70                  75                  80

Trp Tyr Tyr Gln Ser Gly Leu Ser Ile Val Met Pro Val Gly Gly Gln
             85                  90                  95

Ser Ser Phe Tyr Ser Asp Trp Tyr Ser Pro Ala Cys Gly Lys Ala Gly
            100                 105                 110

Cys Gln Thr Tyr Lys Trp Glu Thr Phe Leu Thr Ser Glu Leu Pro Gln
            115                 120                 125

Trp Leu Ser Ala Asn Arg Ala Val Lys Pro Thr Gly Ser Ala Ala Ile
    130                 135                 140

Gly Leu Ser Met Ala Gly Ser Ser Ala Met Ile Leu Ala Ala Tyr His
145                 150                 155                 160

Pro Gln Gln Phe Ile Tyr Ala Gly Ser Leu Ser Ala Leu Leu Asp Pro
                165                 170                 175

Ser Gln Gly Met Gly Pro Ser Leu Ile Gly Leu Ala Met Gly Asp Ala
            180                 185                 190

Gly Gly Tyr Lys Ala Ala Asp Met Trp Gly Pro Ser Ser Asp Pro Ala
            195                 200                 205

Trp Glu Arg Asn Asp Pro Thr Gln Gln Ile Pro Lys Leu Val Ala Asn
    210                 215                 220

Asn Thr Arg Leu Trp Val Tyr Cys Gly Asn Gly Thr Pro Asn Glu Leu
225                 230                 235                 240

Gly Gly Ala Asn Ile Pro Ala Glu Phe Leu Glu Asn Phe Val Arg Ser
                245                 250                 255

Ser Asn Leu Lys Phe Gln Asp Ala Tyr Asn Ala Ala Gly Gly His Asn
            260                 265                 270

Ala Val Phe Asn Phe Pro Pro Asn Gly Thr His Ser Trp Glu Tyr Trp
            275                 280                 285

Gly Ala Gln Leu Asn Ala Met Lys Gly Asp Leu Gln Ser Ser Leu Gly
    290                 295                 300

Ala Gly Lys Leu Ala Met Thr Glu Gln Gln Trp Asn Phe Ala Gly Ile
305                 310                 315                 320

Glu Ala Ala Ala Ser Ala Ile Gln Gly Asn Val Thr Ser Ile His Ser
                325                 330                 335

Leu Leu Asp Glu Gly Lys Gln Ser Leu Thr Lys Leu Ala Ala Ala Trp
            340                 345                 350

Gly Gly Ser Gly Ser Glu Ala Tyr Gln Gly Val Gln Gln Lys Trp Asp
    355                 360                 365

Ala Thr Ala Thr Glu Leu Asn Asn Ala Leu Gln Asn Leu Ala Arg Thr
370                 375                 380

Ile Ser Glu Ala Gly Gln Ala Met Ala Ser Thr Glu Gly Asn Val Thr
385                 390                 395                 400

Gly Met Phe Ala

<210> SEQ ID NO 173
<211> LENGTH: 403
<212> TYPE: PRT
<213> ORGANISM: M

-continued

```
<400> SEQUENCE: 173

Met Ala Thr Val Asn Arg Ser Arg His His His His His His His
  1               5                  10                  15

Ile Glu Gly Arg Ser Met Thr Glu Gln Gln Trp Asn Phe Ala Gly Ile
                 20                  25                  30

Glu Ala Ala Ala Ser Ala Ile Gln Gly Asn Val Thr Ser Ile His Ser
             35                  40                  45

Leu Leu Asp Glu Gly Lys Gln Ser Leu Thr Lys Leu Ala Ala Ala Trp
     50                  55                  60

Gly Gly Ser Gly Ser Glu Ala Tyr Gln Gly Val Gln Gln Lys Trp Asp
 65                  70                  75                  80

Ala Thr Ala Thr Glu Leu Asn Asn Ala Leu Gln Asn Leu Ala Arg Thr
                 85                  90                  95

Ile Ser Glu Ala Gly Gln Ala Met Ala Ser Thr Glu Gly Asn Val Thr
                100                 105                 110

Gly Met Phe Ala Lys Leu Phe Ser Arg Pro Gly Leu Pro Val Glu Tyr
            115                 120                 125

Leu Gln Val Pro Ser Pro Ser Met Gly Arg Asp Ile Lys Val Gln Phe
130                 135                 140

Gln Ser Gly Gly Asn Asn Ser Pro Ala Val Tyr Leu Leu Asp Gly Leu
145                 150                 155                 160

Arg Ala Gln Asp Asp Tyr Asn Gly Trp Asp Ile Asn Thr Pro Ala Phe
                165                 170                 175

Glu Trp Tyr Tyr Gln Ser Gly Leu Ser Ile Val Met Pro Val Gly Gly
            180                 185                 190

Gln Ser Ser Phe Tyr Ser Asp Trp Tyr Ser Pro Ala Cys Gly Lys Ala
        195                 200                 205

Gly Cys Gln Thr Tyr Lys Trp Glu Thr Phe Leu Thr Ser Glu Leu Pro
    210                 215                 220

Gln Trp Leu Ser Ala Asn Arg Ala Val Lys Pro Thr Gly Ser Ala Ala
225                 230                 235                 240

Ile Gly Leu Ser Met Ala Gly Ser Ser Ala Met Ile Leu Ala Ala Tyr
                245                 250                 255

His Pro Gln Gln Phe Ile Tyr Ala Gly Ser Leu Ser Ala Leu Leu Asp
            260                 265                 270

Pro Ser Gln Gly Met Gly Pro Ser Leu Ile Gly Leu Ala Met Gly Asp
        275                 280                 285

Ala Gly Gly Tyr Lys Ala Ala Asp Met Trp Gly Pro Ser Ser Asp Pro
    290                 295                 300

Ala Trp Glu Arg Asn Asp Pro Thr Gln Gln Ile Pro Lys Leu Val Ala
305                 310                 315                 320

Asn Asn Thr Arg Leu Trp Val Tyr Cys Gly Asn Gly Thr Pro Asn Glu
                325                 330                 335

Leu Gly Gly Ala Asn Ile Pro Ala Glu Phe Leu Glu Asn Phe Val Arg
            340                 345                 350

Ser Ser Asn Leu Lys Phe Gln Asp Ala Tyr Asn Ala Ala Gly Gly His
        355                 360                 365

Asn Ala Val Phe Asn Phe Pro Pro Asn Gly Thr His Ser Trp Glu Tyr
    370                 375                 380

Trp Gly Ala Gln Leu Asn Ala Met Lys Gly Asp Leu Gln Ser Ser Leu
385                 390                 395                 400

Gly Ala Gly
```